(12) United States Patent
Werner et al.

(10) Patent No.: US 10,117,909 B2
(45) Date of Patent: Nov. 6, 2018

(54) COMBINATION OF AN INSULIN AND A GLP-1 AGONIST

(71) Applicant: Sanofi-Aventis Deutschland GmbH, Frankfurt (DE)

(72) Inventors: Ulrich Werner, Frankfurt am Main (DE); Barbel Rotthauser, Frankfurt am Main (DE)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 0 days.

(21) Appl. No.: 15/340,969

(22) Filed: Nov. 1, 2016

(65) Prior Publication Data

US 2017/0281733 A1 Oct. 5, 2017

Related U.S. Application Data

(62) Division of application No. 13/123,835, filed as application No. PCT/EP2009/063195 on Oct. 9, 2009, now Pat. No. 9,526,764.

(30) Foreign Application Priority Data

Oct. 17, 2008 (DE) .................. 10 2008 051 834
Oct. 24, 2008 (DE) .................. 10 2008 053 048
Aug. 20, 2009 (DE) .................. 10 2009 038 210

(51) Int. Cl.
*A61K 38/28* (2006.01)
*A61K 38/26* (2006.01)
*A61K 38/00* (2006.01)

(52) U.S. Cl.
CPC .............. *A61K 38/28* (2013.01); *A61K 38/26* (2013.01)

(58) Field of Classification Search
CPC ..................................................... A61K 38/00
See application file for complete search history.

(56) References Cited

U.S. PATENT DOCUMENTS

| | | | |
|---|---|---|---|
| 3,758,683 A | 9/1973 | Jackson | |
| 3,868,358 A | 2/1975 | Jackson | |
| 4,153,689 A | 5/1979 | Hirai et al. | |
| 4,165,370 A | 8/1979 | Coval | |
| 4,258,134 A | 3/1981 | Yoshida et al. | |
| 4,367,737 A | 1/1983 | Kozam et al. | |
| 4,608,364 A | 8/1986 | Grau | |
| 4,614,730 A | 9/1986 | Hansen et al. | |
| 4,644,057 A | 2/1987 | Bicker et al. | |
| 4,689,042 A | 8/1987 | Sarnoff et al. | |
| 4,701,440 A | 10/1987 | Grau | |
| 4,731,405 A | 3/1988 | Kirsch et al. | |
| 4,783,441 A | 11/1988 | Thurow | |
| 4,839,341 A | 6/1989 | Massey et al. | |
| 4,863,902 A | 9/1989 | Amagase et al. | |
| 4,885,164 A | 12/1989 | Thurow | |
| 4,923,162 A | 5/1990 | Fleming et al. | |
| 4,959,351 A | 9/1990 | Grau | |
| 4,960,702 A | 10/1990 | Rice et al. | |
| 4,994,439 A | 2/1991 | Longenecker et al. | |
| 5,008,241 A | 4/1991 | Markussen et al. | |
| 5,034,415 A | 7/1991 | Rubin | |
| 5,070,186 A | 12/1991 | Joergensen | |
| 5,101,013 A | 3/1992 | Doerschug et al. | |
| 5,177,058 A | 1/1993 | Doerschug | |
| 5,187,177 A | 2/1993 | Garzaran | |
| 5,227,293 A | 7/1993 | Stengelin et al. | |
| 5,253,785 A | 10/1993 | Haber et al. | |
| 5,272,135 A | 12/1993 | Takruri | |
| 5,358,708 A | 10/1994 | Patel | |
| 5,358,857 A | 10/1994 | Stengelin et al. | |
| 5,370,629 A | 12/1994 | Michel et al. | |
| 5,397,771 A | 3/1995 | Bechgaard et al. | |
| 5,407,609 A | 4/1995 | Tice et al. | |
| 5,424,286 A | 6/1995 | Eng | |
| 5,428,006 A | 6/1995 | Bechgaard et al. | |
| 5,473,049 A | 12/1995 | Obermeier et al. | |
| 5,474,978 A | 12/1995 | Bakaysa et al. | |
| 5,478,323 A | 12/1995 | Westwood et al. | |
| 5,496,924 A | 3/1996 | Habermann et al. | |
| 5,506,203 A | 4/1996 | Baeckstroem et al. | |
| 5,509,905 A | 4/1996 | Michel | |
| 5,514,646 A | 5/1996 | Chance et al. | |
| 5,524,286 A | 6/1996 | Chiesa et al. | |
| 5,534,488 A | 7/1996 | Hoffmann | |
| 5,545,618 A | 8/1996 | Buckley et al. | |
| 5,547,929 A | 8/1996 | Anderson, Jr. et al. | |
| 5,559,094 A | 9/1996 | Brems et al. | |
| 5,595,756 A | 1/1997 | Bally et al. | |
| 5,597,796 A | 1/1997 | Brange | |

(Continued)

FOREIGN PATENT DOCUMENTS

AU 593274 B2 2/1990
AU 612324 B2 7/1991

(Continued)

OTHER PUBLICATIONS

Werner et al., "The GLP-1 Receptor Agonist AVE0010 Abolishes OGTT-Induced Blood Glucose Excursion in Healthy, Normoglycemic Dog Without Risk of Hypoglycemia" Diabetes 56(Supplement 1):A129 (Jun. 2007). Abstract submitted.

(Continued)

*Primary Examiner* — Shulamith H Shafer
(74) *Attorney, Agent, or Firm* — McDonnell Boehnen Hulbert and Bergoff LLP

(57) ABSTRACT

The invention relates to a drug comprising at least one insulin and at least one GLP-1 receptor agonist.

8 Claims, 12 Drawing Sheets

(56) References Cited

U.S. PATENT DOCUMENTS

Figure 1:
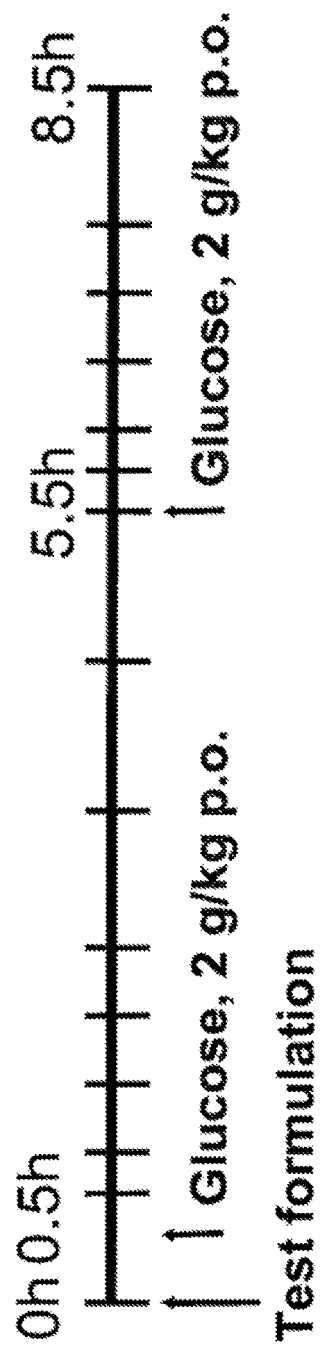

| | | |
|---|---|---|
| 5,614,219 A | 3/1997 | Wunderlich et al. |
| 5,614,492 A | 3/1997 | Habener |
| 5,631,224 A | 5/1997 | Efendic et al. |
| 5,654,008 A | 8/1997 | Herbert et al. |
| 5,656,722 A | 8/1997 | Doerschug |
| 5,663,291 A | 9/1997 | Obermeier et al. |
| 5,670,360 A | 9/1997 | Thorens |
| 5,693,608 A | 12/1997 | Bechgaard et al. |
| 5,700,662 A | 12/1997 | Chance et al. |
| 5,707,641 A | 1/1998 | Gertner et al. |
| 5,783,556 A | 7/1998 | Clark et al. |
| 5,824,638 A | 10/1998 | Burnside et al. |
| 5,846,747 A | 12/1998 | Thorens et al. |
| 5,846,937 A | 12/1998 | Drucker |
| 5,879,584 A | 3/1999 | Bianchetti et al. |
| 5,935,566 A | 8/1999 | Yuen et al. |
| 5,948,751 A | 9/1999 | Kimer et al. |
| 5,952,297 A | 9/1999 | De et al. |
| 5,985,309 A | 11/1999 | Edwards et al. |
| 5,986,048 A | 11/1999 | Rubroder et al. |
| 6,006,753 A | 12/1999 | Efendic |
| 6,034,054 A | 3/2000 | Defelippis et al. |
| 6,043,214 A | 3/2000 | Jensen et al. |
| 6,051,551 A | 4/2000 | Hughes et al. |
| 6,051,689 A | 4/2000 | Thorens |
| 6,100,376 A | 8/2000 | Doerschug |
| 6,110,703 A | 8/2000 | Egel-Mitani et al. |
| 6,174,856 B1 | 1/2001 | Langballe et al. |
| 6,191,102 B1 | 2/2001 | Dimarchi et al. |
| 6,197,926 B1 | 3/2001 | Gaur et al. |
| 6,211,144 B1 | 4/2001 | Havelund |
| 6,227,819 B1 | 5/2001 | Gettel et al. |
| 6,248,363 B1 | 6/2001 | Patel et al. |
| 6,267,981 B1 | 7/2001 | Okamoto et al. |
| 6,268,335 B1 | 7/2001 | Brader |
| 6,268,343 B1 | 7/2001 | Knudsen et al. |
| 6,271,241 B1 | 8/2001 | Desimone et al. |
| 6,284,725 B1 | 9/2001 | Coolidge et al. |
| 6,309,663 B1 | 10/2001 | Patel et al. |
| 6,310,038 B1 | 10/2001 | Havelund |
| 6,329,336 B1 | 12/2001 | Bridon et al. |
| 6,335,316 B1 | 1/2002 | Hughes et al. |
| 6,344,180 B1 | 2/2002 | Holst et al. |
| 6,358,924 B1 | 3/2002 | Hoffmann |
| 6,384,016 B1 | 5/2002 | Kaarsholm |
| 6,388,053 B1 | 5/2002 | Galloway et al. |
| 6,395,767 B2 | 5/2002 | Robl et al. |
| 6,410,508 B1 | 6/2002 | Isales et al. |
| 6,410,511 B2 | 6/2002 | L'Italien et al. |
| 6,417,164 B1 | 7/2002 | Kolterman et al. |
| 6,444,641 B1 | 9/2002 | Flora |
| 6,468,959 B1 | 10/2002 | Wunderlich et al. |
| 6,489,292 B1 | 12/2002 | Havelund et al. |
| 6,528,486 B1 | 3/2003 | Larsen et al. |
| 6,734,162 B2 | 5/2004 | Van et al. |
| 6,737,401 B2 | 5/2004 | Kim et al. |
| 6,767,887 B1 | 7/2004 | Hoffmann et al. |
| 6,818,738 B2 | 11/2004 | Havelund |
| 6,852,694 B2 | 2/2005 | Van et al. |
| 6,875,589 B1 | 4/2005 | Doerschug et al. |
| 6,902,744 B1 | 6/2005 | Kolterman et al. |
| 6,908,610 B1 | 6/2005 | Sato |
| 6,908,897 B2 | 6/2005 | Brandenburg et al. |
| 6,960,561 B2 | 11/2005 | Boderke |
| 6,969,702 B2 | 11/2005 | Bertilsson et al. |
| 7,022,674 B2 | 4/2006 | Defelippis et al. |
| 7,115,563 B2 | 10/2006 | Younis et al. |
| 7,119,086 B2 | 10/2006 | Di et al. |
| 7,192,919 B2 | 3/2007 | Tzannis et al. |
| 7,205,276 B2 | 4/2007 | Boderke |
| 7,205,277 B2 | 4/2007 | Boderke |
| 7,238,663 B2 | 7/2007 | Defelippis et al. |
| 7,405,196 B2 | 7/2008 | Rosskamp et al. |
| 7,476,652 B2 | 1/2009 | Brunner-Schwarz et al. |
| 7,544,656 B2 | 6/2009 | Sabetsky |
| 7,544,657 B2 | 6/2009 | Ebbehoj et al. |
| 7,576,050 B2 | 8/2009 | Greig et al. |
| 7,713,930 B2 | 5/2010 | Brunner-Schwarz et al. |
| 7,803,763 B2 | 9/2010 | Thurow et al. |
| 7,807,242 B2 | 10/2010 | Soerensen et al. |
| 7,918,833 B2 | 4/2011 | Veasey et al. |
| 7,939,293 B2 | 5/2011 | Habermann et al. |
| 7,977,310 B2 | 7/2011 | Rosskamp et al. |
| 8,048,854 B2 | 11/2011 | Habermann et al. |
| 8,084,420 B2 | 12/2011 | Steiner et al. |
| 8,092,421 B2 | 1/2012 | Seiferlein et al. |
| 8,092,422 B2 | 1/2012 | Seiferlein et al. |
| 8,178,495 B2 | 5/2012 | Chilkoti |
| 8,574,214 B2 | 11/2013 | Kuehn et al. |
| 8,633,156 B2 | 1/2014 | Habermann et al. |
| 8,735,349 B2 | 5/2014 | Silvestre et al. |
| 2001/0012829 A1 | 8/2001 | Anderson et al. |
| 2001/0033868 A1 | 10/2001 | Rossling et al. |
| 2001/0039260 A1 | 11/2001 | Havelund |
| 2001/0047084 A1 | 11/2001 | Knudsen et al. |
| 2002/0107265 A1 | 8/2002 | Chen et al. |
| 2002/0132760 A1 | 9/2002 | Van et al. |
| 2002/0177151 A1 | 11/2002 | Gimeno |
| 2002/0198140 A1 | 12/2002 | Havelund |
| 2003/0004096 A1 | 1/2003 | Boderke |
| 2003/0026872 A1 | 2/2003 | Dake et al. |
| 2003/0104983 A1 | 6/2003 | DeFelippis et al. |
| 2003/0170691 A1 | 9/2003 | Gimeno et al. |
| 2003/0212248 A1 | 11/2003 | Furman |
| 2004/0022792 A1 | 2/2004 | Klinke |
| 2004/0037893 A1 | 2/2004 | Hansen et al. |
| 2004/0048783 A1 | 3/2004 | Brunner-Schwarz et al. |
| 2004/0092590 A1 | 5/2004 | Arterburn et al. |
| 2004/0097410 A1 | 5/2004 | Zheng et al. |
| 2004/0106547 A1 | 6/2004 | Larsen et al. |
| 2004/0186046 A1 | 9/2004 | Burgess et al. |
| 2004/0229774 A1 | 11/2004 | Rosskamp et al. |
| 2004/0235710 A1 | 11/2004 | Defelippis et al. |
| 2004/0242853 A1 | 12/2004 | Greig et al. |
| 2005/0014679 A1 | 1/2005 | Beals et al. |
| 2005/0079996 A1 | 4/2005 | Horiguchi et al. |
| 2005/0106147 A1 | 5/2005 | Jordan et al. |
| 2005/0171009 A1 | 8/2005 | Brunner-Schwarz et al. |
| 2005/0209142 A1 | 9/2005 | Bertilsson et al. |
| 2006/0004049 A1 | 1/2006 | Yao et al. |
| 2006/0014678 A1 | 1/2006 | Cowley et al. |
| 2006/0019347 A1 | 1/2006 | Cho et al. |
| 2006/0057137 A1 | 3/2006 | Steiness |
| 2006/0073213 A1 | 4/2006 | Hotamisligil et al. |
| 2006/0093576 A1 | 5/2006 | Chen et al. |
| 2006/0194719 A1 | 8/2006 | Ebbehoj et al. |
| 2006/0239933 A1 | 10/2006 | Nilsson et al. |
| 2006/0287221 A1 | 12/2006 | Knudsen et al. |
| 2007/0027063 A1 | 2/2007 | Boss et al. |
| 2007/0111940 A1 | 5/2007 | Larsen et al. |
| 2007/0128193 A1 | 6/2007 | O'Neil et al. |
| 2007/0135338 A1 | 6/2007 | O'Neil et al. |
| 2007/0155653 A1 | 7/2007 | Boderke |
| 2007/0191271 A1 | 8/2007 | Mayhew et al. |
| 2007/0237827 A1 | 10/2007 | Sung et al. |
| 2008/0064856 A1 | 3/2008 | Warne et al. |
| 2008/0146490 A1 | 6/2008 | Joabsson et al. |
| 2008/0234200 A1 | 9/2008 | Quay et al. |
| 2008/0248999 A1 | 10/2008 | Steiner |
| 2008/0260840 A1 | 10/2008 | Alessi et al. |
| 2008/0267907 A1 | 10/2008 | Poulsen |
| 2009/0082255 A1 | 3/2009 | Brunner-Schwarz et al. |
| 2009/0088369 A1 | 4/2009 | Steiness |
| 2009/0099064 A1 | 4/2009 | Lougheed |
| 2009/0104210 A1 | 4/2009 | Tota et al. |
| 2009/0142338 A1 | 6/2009 | Levetan |
| 2009/0175840 A1 | 7/2009 | Kashyap et al. |
| 2009/0176692 A1 | 7/2009 | Habermann et al. |
| 2009/0180953 A1 | 7/2009 | Gotthardt et al. |
| 2009/0186819 A1 | 7/2009 | Carrier et al. |
| 2009/0208565 A1 | 8/2009 | Ebbehoj et al. |
| 2009/0214468 A1 | 8/2009 | Lin et al. |
| 2009/0214657 A1 | 8/2009 | Qazi et al. |
| 2009/0304665 A1 | 12/2009 | Frost et al. |

(56) References Cited

U.S. PATENT DOCUMENTS

| | | |
|---|---|---|
| 2009/0312236 A1 | 12/2009 | Beals et al. |
| 2009/0324701 A1 | 12/2009 | Williams |
| 2010/0029558 A1 | 2/2010 | Bristow |
| 2010/0055049 A1 | 3/2010 | Kuo et al. |
| 2010/0057194 A1 | 3/2010 | Ryan |
| 2010/0069292 A1 | 3/2010 | Pohl et al. |
| 2010/0069293 A1 | 3/2010 | Bolotin et al. |
| 2010/0227816 A1 | 9/2010 | Flatt et al. |
| 2010/0279931 A1 | 11/2010 | Garibay et al. |
| 2010/0311112 A1 | 12/2010 | Rissom et al. |
| 2011/0020294 A1 | 1/2011 | Hammerman |
| 2011/0021423 A1 | 1/2011 | Olsen et al. |
| 2011/0077197 A1 | 3/2011 | Habermann et al. |
| 2011/0118178 A1 | 5/2011 | Silvestre et al. |
| 2011/0118180 A1 | 5/2011 | Silvestre et al. |
| 2011/0144008 A1 | 6/2011 | Larsen et al. |
| 2011/0152185 A1 | 6/2011 | Plum et al. |
| 2011/0173722 A1 | 7/2011 | Habermann et al. |
| 2011/0230402 A1 | 9/2011 | Johansen et al. |
| 2011/0236925 A1 | 9/2011 | Hazra et al. |
| 2011/0245165 A1 | 10/2011 | Larsen et al. |
| 2011/0281790 A1 | 11/2011 | Pohl et al. |
| 2011/0301081 A1 | 12/2011 | Becker et al. |
| 2012/0021978 A1 | 1/2012 | Werner et al. |
| 2012/0121611 A1 | 5/2012 | Lodie et al. |
| 2012/0122774 A1 | 5/2012 | Becker et al. |
| 2012/0183616 A1 | 7/2012 | Sprogoe et al. |
| 2012/0232002 A1 | 9/2012 | Schoettle et al. |
| 2012/0241356 A1 | 9/2012 | Pfenninger et al. |
| 2012/0252724 A1 | 10/2012 | Schoettle et al. |
| 2012/0277147 A1 | 11/2012 | Boka et al. |
| 2012/0283179 A1 | 11/2012 | Brunner-Schwarz et al. |
| 2012/0295846 A1 | 11/2012 | Hagendorf et al. |
| 2012/0316108 A1 | 12/2012 | Chen et al. |
| 2013/0005649 A1 | 1/2013 | Niemoeller et al. |
| 2013/0012433 A1 | 1/2013 | Rosskamp et al. |
| 2013/0023467 A1 | 1/2013 | Silvestre et al. |
| 2013/0040878 A1 | 2/2013 | Silvestre et al. |
| 2013/0065828 A1 | 3/2013 | Ruus et al. |
| 2013/0079279 A1 | 3/2013 | Becker et al. |
| 2013/0085102 A1 | 4/2013 | Silvestre et al. |
| 2013/0096059 A1 | 4/2013 | Stechl et al. |
| 2013/0096060 A1 | 4/2013 | Stechl et al. |
| 2013/0116179 A1 | 5/2013 | Hess et al. |
| 2013/0203666 A1 | 8/2013 | Niemoeller et al. |
| 2013/0284912 A1 | 10/2013 | Vogel et al. |
| 2013/0296236 A1 | 11/2013 | Silvestre et al. |
| 2013/0317477 A1 | 11/2013 | Edwards et al. |
| 2014/0148384 A1 | 5/2014 | Boka et al. |
| 2014/0206611 A1 | 7/2014 | Becker et al. |
| 2014/0221285 A1 | 8/2014 | Bley et al. |
| 2014/0248365 A1 | 9/2014 | Rademacher et al. |
| 2014/0371141 A1 | 12/2014 | Souhami et al. |
| 2016/0199452 A1 | 7/2016 | Souhami et al. |
| 2016/0235818 A1 | 8/2016 | Bergmann et al. |
| 2016/0287674 A1 | 10/2016 | Roy et al. |
| 2016/0296601 A1 | 10/2016 | Belder et al. |

FOREIGN PATENT DOCUMENTS

| | | |
|---|---|---|
| AU | 2000-72263 | 2/2001 |
| CA | 1173388 A | 8/1984 |
| CA | 1258427 A | 8/1989 |
| CA | 1336329 C | 7/1995 |
| CA | 1341203 C | 3/2001 |
| CA | 2662084 A1 | 3/2008 |
| CA | 2 685 638 | 5/2011 |
| CN | 1276731 A | 12/2000 |
| CN | 1413582 A | 4/2003 |
| CN | 1662252 A | 8/2005 |
| CN | 101366692 A | 2/2009 |
| CN | 101444618 A | 6/2009 |
| CN | 101454019 A | 6/2009 |
| CN | 101670096 A | 3/2010 |
| DE | 2219635 A1 | 11/1972 |
| DE | 3240177 A1 | 5/1983 |
| DE | 19637230 A1 | 3/1998 |
| DE | 10 2008 003 566 | 7/2009 |
| DE | 10 2008 003 568 | 7/2009 |
| DE | 102008053048 A1 | 4/2010 |
| EA | 006019 B1 | 8/2005 |
| EP | 0018609 B1 | 9/1983 |
| EP | 0046979 B1 | 9/1983 |
| EP | 0132769 A1 | 2/1985 |
| EP | 0140084 A1 | 5/1985 |
| EP | 0166529 A1 | 1/1986 |
| EP | 0180920 A2 | 5/1986 |
| EP | 0200383 A2 | 11/1986 |
| EP | 0211299 A2 | 2/1987 |
| EP | 0 214 826 | 3/1987 |
| EP | 0224885 A1 | 6/1987 |
| EP | 0227938 A2 | 7/1987 |
| EP | 0229956 A1 | 7/1987 |
| EP | 0229998 A2 | 7/1987 |
| EP | 0254516 A2 | 1/1988 |
| EP | 0305760 A2 | 3/1989 |
| EP | 0 368 187 | 5/1990 |
| EP | 0 375 437 | 6/1990 |
| EP | 0 383 472 | 8/1990 |
| EP | 0194864 B1 | 6/1992 |
| EP | 0 419 504 | 1/1994 |
| EP | 0600372 A1 | 6/1994 |
| EP | 0668282 A1 | 8/1995 |
| EP | 0668292 A2 | 8/1995 |
| EP | 0 678 522 | 10/1995 |
| EP | 0837072 A2 | 4/1998 |
| EP | 0845265 A1 | 6/1998 |
| EP | 0 885 961 | 12/1998 |
| EP | 1 076 066 | 2/2001 |
| EP | 1172114 A2 | 1/2002 |
| EP | 1196444 A1 | 4/2002 |
| EP | 1222207 A1 | 7/2002 |
| EP | 1 523 993 | 4/2005 |
| EP | 1364029 B1 | 12/2005 |
| EP | 1 906 991 | 4/2008 |
| EP | 2112161 A2 | 10/2009 |
| EP | 2 187 950 | 5/2010 |
| EP | 2324853 A1 | 5/2011 |
| EP | 2329848 A1 | 6/2011 |
| EP | 2389945 A1 | 11/2011 |
| EP | 0921812 B2 | 12/2011 |
| EP | 2387989 B1 | 7/2014 |
| FR | 2456522 A1 | 12/1980 |
| GB | 835638 A | 5/1960 |
| GB | 840870 A | 7/1960 |
| GB | 1527605 A | 10/1978 |
| GB | 1554157 A | 10/1979 |
| JP | S61212598 A | 9/1986 |
| JP | S6399096 A | 4/1988 |
| JP | H02218696 A | 8/1990 |
| JP | 2-264798 | 10/1990 |
| JP | H03504240 A | 9/1991 |
| JP | H06506444 A | 7/1994 |
| JP | 2001521004 A | 11/2001 |
| JP | 2002516880 A | 6/2002 |
| JP | 2003505347 A | 2/2003 |
| JP | 2005508895 A | 4/2005 |
| JP | 2005532365 A | 10/2005 |
| JP | 2006-515267 | 5/2006 |
| JP | 2006137678 A | 6/2006 |
| JP | 2007204498 A | 8/2007 |
| JP | 2009091363 A | 4/2009 |
| JP | 2009519961 A | 5/2009 |
| JP | 2012-505852 | 3/2012 |
| JP | 2012-255040 | 12/2012 |
| RU | 2008116057 A | 10/2009 |
| RU | 2386631 C2 | 4/2010 |
| TW | 157005 B | 5/1991 |
| TW | 562806 B | 11/2003 |
| WO | WO-8300288 A1 | 2/1983 |
| WO | WO-8806599 A1 | 9/1988 |
| WO | WO-8910937 A1 | 11/1989 |
| WO | WO-9007522 A1 | 7/1990 |
| WO | WO-9011299 A1 | 10/1990 |

(56) References Cited

FOREIGN PATENT DOCUMENTS

| | | |
|---|---|---|
| WO | WO-9103550 A1 | 3/1991 |
| WO | WO-9116929 A1 | 11/1991 |
| WO | WO 92/00321 | 1/1992 |
| WO | WO-9212999 A1 | 8/1992 |
| WO | WO-9318786 A1 | 9/1993 |
| WO | WO-9414461 A1 | 7/1994 |
| WO | WO-9500550 A1 | 1/1995 |
| WO | WO-9524183 A1 | 9/1995 |
| WO | WO-9604307 A1 | 2/1996 |
| WO | WO-9607399 A1 | 3/1996 |
| WO | WO-9611705 A1 | 4/1996 |
| WO | WO 96/32414 | 10/1996 |
| WO | WO-9634882 A1 | 11/1996 |
| WO | WO-9641606 A2 | 12/1996 |
| WO | WO-9701331 A2 | 1/1997 |
| WO | WO-9748413 A1 | 12/1997 |
| WO | WO 98/05351 | 2/1998 |
| WO | WO 98/08871 | 3/1998 |
| WO | WO-9808531 A1 | 3/1998 |
| WO | WO-9808873 A1 | 3/1998 |
| WO | WO-9819698 A1 | 5/1998 |
| WO | WO 98/30231 | 7/1998 |
| WO | WO-9835033 A1 | 8/1998 |
| WO | WO-9839022 A1 | 9/1998 |
| WO | WO-9842749 A1 | 10/1998 |
| WO | WO-9856406 A1 | 12/1998 |
| WO | WO-9856418 A1 | 12/1998 |
| WO | WO 99/07404 | 2/1999 |
| WO | WO 99/25727 | 5/1999 |
| WO | WO 99/25728 | 5/1999 |
| WO | WO-9921573 A1 | 5/1999 |
| WO | WO-9921578 A1 | 5/1999 |
| WO | WO-9924071 A1 | 5/1999 |
| WO | WO-9940788 A1 | 8/1999 |
| WO | WO 99/43708 | 9/1999 |
| WO | WO-9946283 A1 | 9/1999 |
| WO | WO-9962558 A1 | 12/1999 |
| WO | WO-0023098 A1 | 4/2000 |
| WO | WO-0023099 A1 | 4/2000 |
| WO | WO-0029013 A1 | 5/2000 |
| WO | WO-0041546 A2 | 7/2000 |
| WO | WO-0066629 A1 | 11/2000 |
| WO | WO-0074736 A1 | 12/2000 |
| WO | WO 01/02039 | 1/2001 |
| WO | WO 01/04156 | 1/2001 |
| WO | WO-0100223 A2 | 1/2001 |
| WO | WO-0112155 A1 | 2/2001 |
| WO | WO-0121154 A2 | 3/2001 |
| WO | WO 01/24814 | 4/2001 |
| WO | WO-0125278 A1 | 4/2001 |
| WO | WO-0128555 A1 | 4/2001 |
| WO | WO 01/32157 | 5/2001 |
| WO | WO-0137808 A1 | 5/2001 |
| WO | WO-0143762 A2 | 6/2001 |
| WO | WO-0151071 A2 | 7/2001 |
| WO | WO-0152937 A1 | 7/2001 |
| WO | WO-0193837 A2 | 12/2001 |
| WO | WO-0200243 A2 | 1/2002 |
| WO | WO-0224214 A2 | 3/2002 |
| WO | WO-02064115 A1 | 8/2002 |
| WO | WO-02065985 A2 | 8/2002 |
| WO | WO-02066628 A2 | 8/2002 |
| WO | WO-02068660 A1 | 9/2002 |
| WO | WO-02070722 A1 | 9/2002 |
| WO | WO-02076495 A1 | 10/2002 |
| WO | WO-02079250 A1 | 10/2002 |
| WO | WO-03002021 A2 | 1/2003 |
| WO | WO 03/020201 | 3/2003 |
| WO | WO-03035028 A1 | 5/2003 |
| WO | WO-03035051 A2 | 5/2003 |
| WO | WO-03044210 A2 | 5/2003 |
| WO | WO-03053339 A2 | 7/2003 |
| WO | WO-03066084 A1 | 8/2003 |
| WO | WO-03094951 A1 | 11/2003 |
| WO | WO-03094956 A1 | 11/2003 |
| WO | WO-03101395 A2 | 12/2003 |
| WO | WO-03105888 A1 | 12/2003 |
| WO | WO 2004/005342 | 1/2004 |
| WO | WO 2004/035623 | 4/2004 |
| WO | WO-2004045592 A2 | 6/2004 |
| WO | WO-2004064862 A1 | 8/2004 |
| WO | WO-2004078196 A1 | 9/2004 |
| WO | WO-2004078197 A1 | 9/2004 |
| WO | WO-2004078198 A1 | 9/2004 |
| WO | WO-2004080480 A1 | 9/2004 |
| WO | WO-2004096854 A2 | 11/2004 |
| WO | WO-2004105781 A2 | 12/2004 |
| WO | WO-2004107979 A1 | 12/2004 |
| WO | WO 2005/023291 | 3/2005 |
| WO | WO-2005021022 A2 | 3/2005 |
| WO | WO-2005028516 A2 | 3/2005 |
| WO | WO 2005/046716 | 5/2005 |
| WO | WO 2004/050115 | 6/2005 |
| WO | WO-2005048950 A2 | 6/2005 |
| WO | WO-2005112949 A1 | 12/2005 |
| WO | WO-2005117948 A1 | 12/2005 |
| WO | WO 2006/000567 | 1/2006 |
| WO | WO-2006015879 A1 | 2/2006 |
| WO | WO 2006/029634 | 3/2006 |
| WO | WO 2006/051103 | 5/2006 |
| WO | WO-2006051110 A2 | 5/2006 |
| WO | WO-2006058620 A2 | 6/2006 |
| WO | WO-2006110551 A2 | 10/2006 |
| WO | WO 2007/006307 | 1/2007 |
| WO | WO-2007001150 A2 | 1/2007 |
| WO | WO-2007024700 A2 | 3/2007 |
| WO | WO-2007028394 A2 | 3/2007 |
| WO | WO-2007031187 A1 | 3/2007 |
| WO | WO-2007035665 A1 | 3/2007 |
| WO | WO-2007036299 A2 | 4/2007 |
| WO | WO-2007037607 A1 | 4/2007 |
| WO | WO-2007044867 A2 | 4/2007 |
| WO | WO-2007050656 A2 | 5/2007 |
| WO | WO 2007/081792 | 7/2007 |
| WO | WO-2007075534 A2 | 7/2007 |
| WO | WO-2007081824 A2 | 7/2007 |
| WO | WO-2007082381 A1 | 7/2007 |
| WO | WO-2007095288 A2 | 8/2007 |
| WO | WO-2007104786 A1 | 9/2007 |
| WO | WO-2007109221 A2 | 9/2007 |
| WO | WO-2007113205 A1 | 10/2007 |
| WO | WO-2007120899 A2 | 10/2007 |
| WO | WO-2008006496 A1 | 1/2008 |
| WO | WO-2008013938 A2 | 1/2008 |
| WO | WO 2008/021560 | 2/2008 |
| WO | WO-2008023050 A1 | 2/2008 |
| WO | WO-2008028914 A1 | 3/2008 |
| WO | WO-2008034881 A1 | 3/2008 |
| WO | WO-2008124522 A2 | 10/2008 |
| WO | WO-2008133908 A2 | 11/2008 |
| WO | WO-2008145323 A1 | 12/2008 |
| WO | WO-2009004627 A2 | 1/2009 |
| WO | WO-2009030498 A2 | 3/2009 |
| WO | WO-2009030499 A1 | 3/2009 |
| WO | WO 2009/039963 | 4/2009 |
| WO | WO-2009048959 A1 | 4/2009 |
| WO | WO 2009/063072 | 5/2009 |
| WO | WO-2009056569 A1 | 5/2009 |
| WO | WO 2009/087081 | 7/2009 |
| WO | WO 2009/087082 | 7/2009 |
| WO | WO-2009089181 A1 | 7/2009 |
| WO | WO-2009098318 A1 | 8/2009 |
| WO | WO-2009102467 A2 | 8/2009 |
| WO | WO 2009/143014 | 11/2009 |
| WO | WO-2009134380 A2 | 11/2009 |
| WO | WO-2010030670 A2 | 3/2010 |
| WO | WO-2010043566 A2 | 4/2010 |
| WO | WO-2010044867 A1 | 4/2010 |
| WO | WO 2010/089304 | 8/2010 |
| WO | WO-2010092163 A2 | 8/2010 |
| WO | WO 2010/138671 | 12/2010 |
| WO | WO-2011012719 A1 | 2/2011 |
| WO | WO-2011017554 A2 | 2/2011 |
| WO | WO-2011029892 A2 | 3/2011 |

(56) References Cited

FOREIGN PATENT DOCUMENTS

| WO | WO-2011058082 A1 | 5/2011 |
|---|---|---|
| WO | WO-2011058083 A1 | 5/2011 |
| WO | WO 2011/089203 | 7/2011 |
| WO | WO-2011103575 A1 | 8/2011 |
| WO | WO-2011122921 A2 | 10/2011 |
| WO | WO-2011128374 A1 | 10/2011 |
| WO | WO-2011144673 A2 | 11/2011 |
| WO | WO-2011144674 A2 | 11/2011 |
| WO | WO-2011147980 A1 | 12/2011 |
| WO | WO-2011157402 A1 | 12/2011 |
| WO | WO-2011160066 A1 | 12/2011 |
| WO | WO-2012012352 A2 | 1/2012 |
| WO | WO-2012028172 A1 | 3/2012 |
| WO | WO-2012055967 A2 | 5/2012 |
| WO | WO-2012065996 A1 | 5/2012 |
| WO | WO-2012066086 A1 | 5/2012 |
| WO | WO-2012080320 A1 | 6/2012 |
| WO | WO-2012104342 A1 | 8/2012 |
| WO | WO-2012125569 A2 | 9/2012 |
| WO | WO-2012156296 A1 | 11/2012 |
| WO | WO-2012156299 A1 | 11/2012 |
| WO | WO-2012177929 A2 | 12/2012 |
| WO | WO-2013060850 A1 | 5/2013 |
| WO | WO-2014017849 A1 | 1/2014 |
| WO | WO-2014118355 A1 | 8/2014 |
| WO | WO 2014/202483 | 12/2014 |
| WO | WO 2015/059302 | 4/2015 |

OTHER PUBLICATIONS

Werner, "Preclinical pharmacology of the new GLP-1 receptor agonist AVE0010", Ann. Endocrinol. (Paris), 69(2):164-65 (Apr. 2008).
WHO, World Health Organization Media Center. Obesity and overweight, Fact Sheet No. 311. Updated Jan. 2015, pp. 1-5.
WHO, World Health Organization Media Center. Diabetes Fact Sheet. Available from: http://www.who.int/mediacentre/factsheets/fs312/en/index.html. Accessed Jun. 13, 2016, pp. 1-6.
Wikipedia® entry for "Lixisenatide" Retrieved from the Internet: https://en.wikipedia.org/wiki/Lixisenatide pp. 1-2, last updated Dec. 2015.
Wikipedia® entry for "Pioglitazone" Retrieved from the Internet: https://en.wikipedia.org/wiki/Pioglitazone pp. 1-3, retrieved Apr. 11, 2016.
Wikipedia® entry for "Metformin" Retrieved from the Internet: https://en.wikipedia.org/wiki/Metformin pp. 1-21, retrieved Apr. 11, 2016.
Wikipedia® entry for "Body mass index" Retrieved from the Internet: https://en.wikipedia.org/wiki/Body mass_index pp. 1-14, retrieved Feb. 26, 2016.
Wikipedia® entry for "Stratified sampling" Retrieved on Mar. 28, 2017, pp. 1-4.
Wild et al., "Global prevalence of diabetes: estimates for the year 2000 and projections for 2030." Diabetes Care 27 (5):1047-53 (May 2004).
Williams et al., "Macrovascular disease in Diabetes." In handbook of Diabetes. 2nd ed. Williams G, Pickup JC, Eds. Oxford, UK, Blackwell Science pp. 151-158 (1999).
Williams & Pickup, "Macrovascular disease in Diabetes." In handbook of Diabetes. 2nd ed. Williams G, Pickup JC, Eds. Oxford, UK, Blackwell Science pp. 151-158 (1999).
Wiviott et al., "Greater Clinical Benefit of More Intensive Oral Antiplatelet Therapy With Prasugrel in Patients With Diabetes Mellitus in the Trial to Assess Improvement in Therapeutic Outcomes by Optimizing Platelet Inhibition With Prasugrel-Thrombolysis in Myocardial Infarction 38." Circulation 118(16):1626-36 (Oct. 2008; Epub Aug. 31, 2008).
Wohlfart et al., "Cardioprotective effects of lixisenatide in rat myocardial ischemia-reperfusion injury studies" Journal of Translational Medicine, 11(1):84, 12 pages (Mar. 2013).

Wolever et al., "Second-meal effect: low-glycemic-index foods eaten at dinner improve subsequent breakfast glycemic response." Am J Clin Nutr 48(4):1041-47 (Oct. 1988).
World Health Organization, "Definition, Diagnosis and Classification of Diabetes Mellitus and its Complications. Part 1: Diagnosis and Classification of Diabetes Mellitus." WHO/NCD/NCS/99.2. Geneva; pp. 1-66, (1999).
World Health Organisation report on "Definition and diagnosis of diabetes mellitus and intermediate hyperglycemia: report of a WHO/IDF consultation" pp. 1-50 (2006).
Wright et al., U.K. Prospective Diabetes Study Group. "Sulfonylurea inadequacy: efficacy of addition of insulin over 6 years in patients with type 2 diabetes in the UK. Prospective Diabetes Study (UKPDS 57)." Diabetes Care 25 (2):330-36 (Feb. 2002).
Yki-Järvinen, "Combination Therapies with insulin in type 2 diabetes." Diabetes Care 24(4):758-67 (Apr. 2001).
Yki-Järvinen et al., "Comparison of Bedtime insulin regimes in patients with type 2 diabetes mellitus." Annals of Internal Medicine 130(5):389-96 (Mar. 1999).
Yusuf et al., "Effects of clopidogrel in addition to aspirin in patients with acute coronary syndromes without ST-segment elevation." N Engl J Med 345(7):494-502 (Aug. 2001).
Zeitler et al., "ISPAD Clinical Practice Consensus Guidelines 2014. Type 2 diabetes in the child and adolescent." Pediatr Diabetes 15(Suppl 20):26-46 (Sep. 2014).
Zimmet et al., "The metabolic syndrome in children and adolescents." Lancet 369(9579):2059-61 (Jun. 2007).
Zimmet et al., "Global and societal implications of the diabetes epidemic." Nature 414(6865):782-87 (Dec. 2001).
Zinman et al., "The Effect of Adding Exenatide to a Thiazolidinedione in Suboptimally Controlled Type 2 Diabetes" Annals of Internal Medicine, 146(7):477-85 (Apr. 2007).
Zoungas et al, "Combined Effects of Routine Blood Pressure Lowering and Intensive Glucose Control on Macrovascular and Microvascular Outcomes in Patients With Type 2 Diabetes. New results from the Advance trial." Diabetes Care 32(11)2068-74 (Nov. 2009; Epub Aug. 3, 2009).
Final Office Action issued in U.S. Appl. No. 13/123,835; dated Nov. 18, 2015, pp. 1-16.
Non-Final Office Action issued in U.S. Appl. No. 13/123,835; dated May 28, 2015, pp. 1-11.
Non-Final Office Action issued in U.S. Appl. No. 13/123,835; dated Dec. 22, 2014, pp. 1-13.
Final Office Action issued in U.S. Appl. No. 13/123,835; dated Feb. 12, 2013, pp. 1-13.
Non-Final Office Action issued in U.S. Appl. No. 13/123,835; dated Jul. 19, 2012, pp. 1-14.
Final Rejection issued in U.S. Appl. No. 13/382,442; dated Sep. 21, 2016, pp. 1-32.
Final Rejection issued in U.S. Appl. No. 13/382,772; dated Feb. 24, 2016, pp. 1-36.
Final Office Action from U.S. Appl. No. 12/617,805; dated May 25, 2016, pp. 1-9.
Final Rejection issued in U.S. Appl. No. 13/509,507; dated May 13, 2016, pp. 1-11.
Non-Final Rejection issued in U.S. Appl. No. 13/509,542; dated Nov. 23, 2016, pp. 1-34.
Non-Final Rejection issued in U.S. Appl. No. 13/467,707; dated Jun. 30, 2016, pp. 1-9.
Final Rejection in U.S. Appl. No. 13/633,563; dated Apr. 8, 2016, pp. 1-12.
Final Rejection in U.S. Appl. No. 13/633,496; dated Aug. 26, 2015, pp. 1-16.
Non-Final Rejection in U.S. Appl. No. 13/633,496; dated Apr. 21, 2016, pp. 1-12.
Final Rejection in U.S. Appl. No. 13/633,496; dated Oct. 13, 2016, pp. 1-10.
Final Rejection issued in U.S. Appl. No. 14/303,895; dated Apr. 27, 2015, pp. 1-10.
International Search Report by the ISA for International Application No. PCT/EP2009/000018; dated Jun. 30, 2009, pp. 1-8.
International Search Report by the ISA for International Application No. PCT/EP2016/050804; dated Mar. 4, 2016, pp. 1-4.

(56) References Cited

OTHER PUBLICATIONS

International Search Report by the ISA for International Application No. PCT/EP2016/055267; dated May 20, 2016, pp. 1-7.
International Search Report by the ISA for International Application No. PCT/EP2016/055267; dated Jun. 7, 2016, pp. 1-8.
Partial International Search Report by the ISA for International Application No. PCT/EP2016/055954; dated Jun. 21, 2016, pp. 1-6.
International Search Report by the ISA for International Application No. PCT/EP2016/055954; dated Sep. 9, 2016, pp. 1-12.
Extended European Search Report for European Application No. 14 19 7685; dated Aug. 10, 2015, pp. 1-4.
Extended European Search Report for European Application No. 14 19 7685; dated Oct. 6, 2015, pp. 1-4.
Extended European Search Report for European Application No. 15 15 1488.2; dated Jul. 7, 2015, pp. 1-8.
Extended European Search Report for European Application No. 15 15 9064.3; dated Oct. 19, 2015, pp. 1-4.
English translation of the TIPO Search Report for Roc Patent Application No. 101131466 dated Mar. 2, 2016, one page.
Non-Final Rejection issued in U.S. Appl. No. 13/509,507; dated Sep. 21, 2016, pp. 1-7.
Non-Final Rejection issued in U.S. Appl. No. 14/172,151; dated Jan. 19, 2017, pp. 1-20.
Final Rejection issued in U.S. Appl. No. 14/172,151; dated Jan. 4, 2016, pp. 1-20.
Non-Final Rejection issued in U.S. Appl. No. 13/467,707; dated Nov. 7, 2016, pp. 1-17.
Non-Final Rejection in U.S. Appl. No. 13/633,563; dated Oct. 5, 2016, pp. 1-12.
Non-Final Rejection issued in U.S. Appl. No. 14/303,895; dated Mar. 24, 2017, pp. 1-17.
Non-Final Rejection issued in U.S. Appl. No. 14/965,586; dated Mar. 22, 2017, pp. 1-17.
Non-Final Rejection issued in U.S. Appl. No. 15/068,286; dated Apr. 11, 2017, pp. 1-12.
U.S. Appl. No. 13/382,772, filed May 29, 2012, Schoettle.
U.S. Appl. No. 13/382,442, filed Feb. 21, 2012, Schoettle.
U.S. Appl. No. 13/509,507, filed Jul. 30, 2014, Brunner-Schwarz et al.
U.S. Appl. No. 13/509,542, filed Aug. 2, 2012, Hagendorf et al.
U.S. Appl. No. 14/172,151, filed Feb. 4, 2014, Bley et al.
U.S. Appl. No. 12/617,805, filed Nov. 13, 2009, Silvestre et al.
U.S. Appl. No. 12/617,811, filed Nov. 13, 2009, Silvestre et al.
U.S. Appl. No. 14/220,562, filed Mar. 20, 2014, Becker et al.
U.S. Appl. No. 13/700,631, filed Nov. 11, 2012, Becker et al.
U.S. Appl. No. 13/595,590, filed Aug. 27, 2012, Niemoller et al.
U.S. Appl. No. 13/602,913, filed Sep. 4, 2012, Hess et al.
U.S. Appl. No. 13/633,563, filed Oct. 2, 2012, Stechl et al.
U.S. Appl. No. 13/123,835, filed Sep. 30, 2011, Werner et al.
U.S. Appl. No. 13/633,496, filed Oct. 2, 2012, Stechl et al.
U.S. Appl. No. 14/303,895, filed Jun. 13, 2014, Souhami et al.
U.S. Appl. No. 14/965,586, filed Dec. 10, 2015, Souhami et ai.
U.S. Appl. No. 14/995,910, filed Jan. 14, 2016, Bergmann et al.
U.S. Appl. No. 15/073,364, filed Mar. 17, 2016, Belder et al.
U.S. Appl. No. 15/068,286, filed Mar. 11, 2016, Roy et al.
U.S. Appl. No. 13/819,114, filed Apr. 29, 2013, Boka et al.
U.S. Appl. No. 13/363,956, filed Feb. 1, 2012, Silvestre et al.
U.S. Appl. No. 13/432,811, filed Mar. 28, 2012, Boka et al.
U.S. Appl. No. 13/469,633, filed May 11, 2012, Ruus et al.
U.S. Appl. No. 13/467,707, filed May 9, 2012, Niernoller et al.
U.S. Appl. No. 13/468,422, filed May 10, 2012, Silvestre et al.
U.S. Appl. No. 13/467,757, filed May 9, 2012, Silvestre et al.
U.S. Appl. No. 13/661,476, filed Oct. 26, 2012, Silvestre et al.
Denker et al., "Exenatide (Exendin-4)-Induced Pancreatitis: A case report" Diabetes Care 29(2):471 (Feb. 2006).
Ganz et al., "The association of body mass index with the risk of type 2 diabetes: a case-control study nested in an electronic health records system in the United States." Diabetology & Metabolic Syndrome, 6:50, pp. 1-8 (Apr. 2014).
Mokdad et al., "The association of body mass index with the risk of type 2 diabetes: a case-control study nested in an electronic health records system in the United States." JAMA, 289(1):76-79 (Jan. 2003).
Russell-Jones, "Current developments in the treatment of diabetes: the incretin therapies" Br J Diabetes Vasc Dis. 10:21-30 (Feb. 2010).
Non-Final Office Action issued in U.S. Appl. No. 15/275,867; dated Jun. 1, 2017; pp. 1-11.
Non-Final Rejection in U.S. Appl. No. 13/633,496; dated May 25, 2017, pp. 1-10.
U.S. Appl. No. 13/382,772, filed May 29, 2012, Slow-Acting Insulin Preparations, US20120232002, abandoned.
U.S. Appl. No. 13/382,442, filed Feb. 21, 2012, Insulin Preparations Containing Methionine, US20120252724, pending.
U.S. Appl. No. 13/509,507, filed Jul. 30, 2012, Pharmaceutical Composition Comprising a GLP-1 Agonist and Methionine, US20120283179, pending.
U.S. Appl. No. 13/509,542, filed Aug. 2, 2012, Pharmaceutical Composition Comprising a GLP-1 Agonist, an Insulin and Methionine.
U.S. Appl. No. 14/172,151, filed Feb. 4, 2014, Stabilized Pharmaceutical Formulations of Insulin Analogues and/or Insulin Derivatives, US20140221285, pending.
U.S. Appl. No. 13/123,835, filed Sep. 30, 2011, Combination of an Insulin and a GLP-1-Agonist, US20120021978, patented.
U.S. Appl. No. 12/617,805, filed Nov. 13, 2009, Method of Treatment of Diabetes Type 2 Comprising Add-On Therapy to Insulin Glargine and Metformin, US20110118178, abandoned.
U.S. Appl. No. 12/617,811, filed Nov. 13, 2009, Method of Treatment of Diabetes Type 2 Comprising Add-On Therapy to Metformin, US20110118180, abandoned.
U.S. Appl. No. 14/220,562, filed Mar. 20, 2014, Long-Acting Formulations of Insulin, US20140206611, patented.
U.S. Appl. No. 13/700,631, filed Nov. 11, 2012, Pharmaceutical Composition Comprising AVE0010 and Insulin Glargine, US20130079279, abandoned.
U.S. Appl. No. 13/819,114, filed Apr. 29, 2013, Use of AVE0010 for the Treatment of Diabetes Mellitus Type 2, US20140148384, abandoned.
U.S. Appl. No. 13/363,956, filed Feb. 1, 2012, Prevention of Hypoglycemia in Diabetes Mellitus Type 2 Patients, US20130085102, abandoned.
U.S. Appl. No. 13/432,811, filed Mar. 28, 2012, Preventions of Hypoglycaemia in Diabetes Mellitus Type 2 Patients, US20120277147, abandoned.
U.S. Appl. No. 13/469,633, filed May 11, 2012, Pharmaceutical Combination for Use in Glycemic Control in Diabetes Type 2 Patients, US20130065828, abandoned.
U.S. Appl. No. 13/467,707, filed May 9, 2012, Pharmaceutical Combination for Improving Glycemic Control as Add-On Therapy to Basal Insulin, US20130005649, pending.
U.S. Appl. No. 13/468,422, filed May 10, 2012, Pharmaceutical Combination for Use in the Treatment of Diabetes Type 2 Patients, US20130040878, abandoned.
U.S. Appl. No. 13/467,757, filed May 9, 2012, A method for improving glucose tolerance in a diabetes type 2 patient of younger than 50 years and having postprandial plasma glucose concentration of at least 14 mmol/L, US20130023467, patented.
U.S. Appl. No. 13/595,590, filed Aug. 7, 2012, Pharmaceutical Combination for Use in Glycemic Control in Diabetes Type 2 Patients, US20130203666, patented.
U.S. Appl. No. 13/602,913, filed Sep. 4, 2012, Pharmaceutical Composition for Use in the Treatment of a Neurodegenerative Disease, US20130116179, patented.
U.S. Appl. No. 13/633,563, filed Oct. 2, 2012, GLP-1 Agonist for Use in the Treatment of Stenosis or/and Obstruction in the Pancreatic Duct System, US20130096060, pending.
U.S. Appl. No. 13/633,496, filed Oct. 2, 2012, GLP-1 Agonist for Use in the Treatment of Stenosis or/and Obstruction in the Biliary Tract.
U.S. Appl. No. 13/661,476, filed Oct. 26, 2012, Treatment Protocol of Diabetes Type 2, US20130296236, abandoned.

(56) References Cited

OTHER PUBLICATIONS

U.S. Appl. No. 14/303,895, filed Jun. 13, 2014, Insulin glargine/lixisenatide fixed ratio formulation, US20140371141, pending.
U.S. Appl. No. 14/965,586, filed Dec. 10, 2015, Insulin glargine/lixisenatide fixed ratio formulation, US20160199452, pending.
U.S. Appl. No. 14/995,910, filed Jan. 14, 2016, Treatment of Pediatric Type 2 Diabetes Mellitus Patients, US20160235818, pending.
U.S. Appl. No. 15/073,364, filed Mar. 17, 2016, Treatment of Type 2 Diabetes Mellitus Patients, US20160296601, pending.
U.S. Appl. No. 15/068,286, filed Mar. 11, 2016, Treatment Type 2 Diabetes Mellitus Patients, US20160287674, pending.
Schubert-Zsilavecz et al., "Better blood sugar control in diabetics. Insulin glargin—a long acting insulin analogue," Pharmazie in Unserer Zeit 30(2):125-30 (2001). With English translation.
Holst "Glucagon-like Peptide-1, A Gastrointestinal Hormone with a Pharmaceutical Potential," Current Medicinal Chemistry 6:1005-17 (1999).
Chi et al., "Excipients and their Effects on the Quality of Biologics" pp. 1-9, (May 2012).
Non-Final Rejection issued in U.S. Appl. No. 13/382,442; dated Mar. 31, 2016, pp. 1-29.
International Search Report by the ISA for International Application No. PCT/EP2015/079285; dated Mar. 9, 2016, pp. 1-7.
English translation of the TIPO Search Report for ROC Patent Application No. 104116749, dated Feb. 22, 2016, one page.
Heinrich et al., "Pre-proglucagon messenger ribonucleic acid: nucleotide and encoded amino acid sequences of the rat pancreatic complementary deoxyribonucleic acid." Endocrinology 115(6):2176-81 (1984).
Raufman, "Bioactive peptides from lizard venoms." Regulatory Peptides 61(1):1-18 (1996).
Uttenthal et al., "Molecular forms of glucagon-like peptide-1 in human pancreas and glucagonomas." J Clin Endocrinol Metabol 61(3):472-79 (1985).
The Diabetes Control and Complications Trial Research Group, "The Effect of Intensive Treatment of Diabetes on the Development and Progression of Long-Term Complications in Insulin-Dependent Diabetes Mellitus" 329(14):977-86 (1993).
Goke et al., "Exendin-4 is a high potency agonist and truncated exendin-(9-39)-amide an antagonist at the glucagon-like peptide 1-(7-36)-amide receptor of insulin-secreting beta-cells." J. Biol Chem 268(26):19650-55 (1993).
International Search Report by the ISA for International Application No. PCT/EP2009/063195; dated May 6, 2010, one page.
English Translation of TIPO Search Report for ROC Patent Application No. 101130936, dated Dec. 1, 2015, one page.
Final Rejection issued in U.S. Appl. No. 13/467,707; dated Feb. 12, 2016, pp. 1-12.
Final-Rejection issued in U.S. Appl. No. 13/432,811; dated Feb. 10, 2016, pp. 1-9.
Final Rejection issued in U.S. Appl. No. 13/509,542, dated Feb. 10, 2016, pp. 1-40.
NHSC—National Horizon Scanning Center, "AVE0010 (ZP10) for type 2 diabetes mellitus" University of Birmingham, England; pp. 1-6 (Dec. 2008).
Search Report of the Intellectual Property Office of Singapore for Patent Application No. 10201500871T, dated Nov. 2, 2015, pp. 1-3.
Eng et al., "Isolation and characterization of exendin-4, an exendin-3 analogue, from Heloderma suspectum venom. Further evidence for an exendin receptor on dispersed acini from guinea pig pancreas," J Biol Chem 267(11):7402-5 (1992).
Pi-Sunyer et al., "The effects of pharmacologic agents for type 2 diabetes mellitus on body weight". Postgrad Med. 120(2):5-17 (Jul. 2008).
Weyer et al., "Long-term changes in insulin action and insulin secretion associated with gain, loss, regain and maintenance of body weight", Diabetologia, (43)1:36-46 (Jan. 2000).
WHO Rational Use of Medicines,http://www.who.int/medicines/areas/rational_use/en/downloaded Dec. 18, 2014 10:02:48 AM (2012).

Tews et al., Abstract of Oral Presentation "Enhanced Protection Against Cytokine- and Fatty Acid-induced Apoptosis in Ins-1 Beta-Cells by Combined Treatment with Insulin Glargine and the Novel GLP-1 Receptor Agonist AVE0010" Diabetes, 56(Suppl. 1):A72-A73 (2007).
FDA Frequently Asked Questions about Combination Products;accessed from www.fda.gov/CombinationProducts/AboutCombinationProducts/usm101496.1/htm, 2009 downloaded Jul. 13, 2012, pp. 1-18.
Correa, "Pautas para el examen de patentes farmaceuticas. Una perspectiva desde la Salud Publica. Documento de Trabajo" Universidad de Buenos Aires, Mar. 2008, see English on pp. 19-20, pp. 1-66.
Nauck et al., "Glucagon-like peptide 1 (GLP-1) as a new therapeutic approach for type 2-diabetes," Exp Clin Endocrinol. Diabetes 105(4):187-95 (1997).
Lopez-Delgado et al., "Effects of Glucagon-Like Peptide I on the Kinetics of Glycogen Synthase a in Hepatocytes from Normal and Diabetic Rats," Endocrinology 139(6):2811-2817 (1998).
Tews et al., "Enhanced protection against cytokine- and fatty acid-induced apoptosis in pancreatic beta cells by combined treatment with glucagon-like peptide-1 receptor agonists and insulin analogues." Horm Metab Res. 40(3):172-80 (Mar. 2008).
Petersen & Christensen et al., "Clinical potential of lixisenatide once daily treatment for type 2 diabetes mellitus" Diabetes, Metabolic Syndrome and Obesity: Targets and Therapy, 6:217-31 (Jun. 2013).
Petrie, "The cardiovascular safety of incretin-based therapies: a review of the evidence" Cardiovascular Diabetology, 12(1):130, 12 pages (Sep. 2013).
Pinhas-Hamiel & Zeitler, "Clinical presentation and treatment of type 2 diabetes in children." Pediatric Diabetes 8(9)16-27 (Dec. 2007).
Pi-Sunyer, "The Impact of Weight Gain on Motivation, Compliance, and Metabolic Control in Patients with Type 2 Diabetes Mellitus." Postgrad Med. 121(5):94-107 (Sep. 2009).
Raman & Heptulla, "New potential adjuncts to treatment of children with type 1 diabetes mellitus" Pediatric Research, 65(4):370-74 (Apr. 2009).
Ratner et al., "Efficacy and safety of lixisenatide once-daily versus placebo in patients with type 2 diabetes mellitus nsufficiently controlled on sulfonylurea +/− metformin (GetGoal-S)" Presentation Abstract for Presentation No. 785. 47th EASD Annual Meeting, Lisbon, Sep. 12-16, 2011, pp. 1-3.
Ray et al., "Effect of intensive control of glucose on cardiovascular outcomes and death in patients with diabetes mellitus: a meta-analysis of randomized controlled trials." Lancet 373(9677):1765-72 (May 2009).
Register of medicaments (RM), 2003, issue 10, p. 517.
Remington: The Science and Practice of Pharmacy, Twentieth Edition, Lippincott Williams & Wilkins, USA, "Pancreatic Disorders" pp. 1081-1082 and "Metformin Hydrochloride" p. 1375; 2000.
Remington: The Science and Practice of Pharmacy, Twentieth Edition, Lippincott Williams & Wilkins, USA, "Oral Hypoglycemic and Hyperglycemic Drugs" pp. 1373 and 1375; 2000.
Riddle et al., "The treat-to-target trial: randomized addition of glargine or human NPH insulin to oral therapy of type 2 Diabetes patients." Diabetes Care 26(11):3080-86 (Nov. 2003).
Riddle, "Combined Therapy With Insulin Plus Oral Agents: Is There Any Advantage?" Diabetes Care 31(Supplement 2):S125-S130 (Feb. 2008).
Riddle, "Timely initiation of basal insulin." Am J Med 116(Suppl 3A):3S-9S (Feb. 2004).
Rothstein et al., "Anticandida activity is retained in P-113, a 12-amino-acid fragment of histatin 5." Antimicrob Agents Chemother. 45(5):1367-73 (May 2001).
Rosenstock J et al., Advancing Basal Insulin Glargine with Prandial Lixisenatide QD vs. Insulin Glulisine QD or TID in T2DM: The GetGoalDuo2 Evidence-Based Trial (NCT01768559). Poster 107 -LB, Presented on Sunday, Jun. 7, 2015, 75th Scientific Sessions of the American Diabetes Association, Boston, Massachusetts Jun. 5-9, 2015.

(56) References Cited

OTHER PUBLICATIONS

RPMI-1640 Media Formulation, Sigma Aldrich, accessed on Jul. 10, 2016, pp. 1-5.
Ruetten et al., "Protective effects of the GLP-1 receptor agonist lixisenatide on ischaemia-reperfusion-induced myocardial infarction in an isolated rat heart model" Diabetologia, Abstract 810, 54(Supplement 1):S329 (Sep. 2011).
Russell-Jones & Khan, Insulin-associated weight gain in diabetes: causes, effects and coping strategies. Diabetes Obes Metab.9(6):799-812 (Nov. 2007).
Sacks et al., "Guidelines and Recommendations for Laboratory Analysis in the Diagnosis and Management of Diabetes Mellitus." Clinical Chemistry 48(3):436-72 (Mar. 2002).
Sanofi, "A randomized, double-blind, placebo controlled trial to assess safety, tolerability, pharmacokinetics and pharmacodynamics of lixisentatide in pediatric (10-17 years old) and adult patients with type 2 diabetes", Sanofi, pp. 1-12 (2015). retrieved from the internet: http://en.sanofi.com/img/content/study/PKD11475_summary.pdf (retrieved on Jun. 16, 2015).
Sanofi Press Release entitled "Sanofi Announces Top-Line Results for Cardiovascular Outcomes Study of Lyxumia® (lixisenatide),", dated Mar. 19, 2015, Paris, France, pp. 1-2.
Sanofi-aventis Press Release, "A promising R&D portfolio, well positioned to deliver future growth" (dated Sep. 17, 2007) pp. 1-11.
Sanofi Presentation, "Natixis Conference on Diabetes" Pierre Chancel, pp. 1-23, Nov. 8, 2011.
Zealand Pharma Company Announcement "Zealand Pharma, Additional positive results from Global Phase III program with -3-lixisenatide for type 2 diabetes", Apr. 12, 2011, pp. 1-3, URL, http://files.shareholder.com/downloads/ABEA-58QR0J/0x0x458202/3ccd84a6-5199-451a-ada0-0a8282da3dad/ZEAL_News_2011_4_12Company_Releases.pdf.
Schernthaner et al., "Is the ADA/EASD algorithm for the management of type 2 diabetes (Jan. 2009) based on evidence or opinion? A critical analysis." Diabetologia.53(7):1258-69 (Jul. 2010; Epub Mar. 31, 2010).
Schwartz et al., "New Equations to Estimate GFR in Children with CKD." J Am Soc Nephrol. 20(3):629-37 (Mar. 2009; epub Jan. 21, 2009).
Seino et al., "Lixisenatide significantly improves glycemic control in Asian patients with T2DM insufficiently controlled on basal insulin ± SU." Diabetes, Abstract book for 71st Scientific Session. p. A76; Abstract 278-OR (2011).
Shaw et al., "US valuation of the EQ-5D health states: development and testing of the D1 valuation model." Med Care 43(3):203-20 (Mar. 2005).
Shehadeh et al., "Can GLP-1 preparations be used in children and adolescents with diabetes mellitus?" Pediatric Endocrinology Reviews, 11(3):324-27 (Mar. 2014).
Sillars et al., "Sulphonylurea-metformin combination therapy, cardiovascular disease and all-cause mortality: the Fremantle Diabetes Study." Diabetes Obes Metab. 12(9):757-65 (Sep. 2010).
Sloop et al., "Glucagon as a target for the treatment of Type 2 diabetes." Expert Opin Ther Targets. 9(3):593-600 (Jun. 2005).
Spasov & Chepurnova, "Scientific Approaches to Combination Therapy for Type 2 Diabetes Mellitus," Bulletin of Volgograd State Medical University,1(37):8-10 (2011). See English Absract.
Spertus et al., "Monitoring the quality of life in patients with coronary heart disease." Am J Cardiol. 74(12):1240-44 (Dec. 1994).
Spertus et al., "Development and evaluation of the Seattle Anginal Questionnaire: a new functional status measure for coronary artery disease." J Am Coli Cardiol. 25(2):333-41 (Feb. 1995).
Spertus et al., "Health status predicts long-term outcome in outpatients with coronary disease." Circulation. 106(1):43-49 (Jul. 2002).
Srinivasan & Ramarao, "Animal models in type 2 diabetes research: An overview." Indian J Med Res. 125:451-472 (Mar. 2007).
Standardized Definitions for Cardiovascular Outcomes Trials: Draft Recommendations. Division of Metabolism and Endocrinology Products. Center for Drug Evaluation and Research (CDER). pp. 1-34, Mar. 24, 2010.
Stumvoll et al., "Type 2 diabetes: Principles of pathogenesis and therapy." Lancet 365(9467):1333-46 (Apr. 2005).
Tanner et al., "Standards from birth to maturity for height, weight, height velocity, and weight velocity: British children, Part Ii" Arch Dis Child. 41(220):613-35 (1966).
Tanner & Davies, "Clinical longitudinal standards for height and height velocity for North American children." J Pediatr. 107(3):317-29 (Sep. 1985).
The Advance Collaborative Group, "Intensive blood glucose control and vascular outcomes in patients with type 2 diabetes." N Engl J Med 358(24):2560-72 (Jun. 2008).
The Criteria Committee of the New York Heart Association, "Nomenclature and Criteria for Diagnosis of Diseases of the Heart and Great Vessels." 9th edition. Boston, Mass: Little, Brown & Co; pp. 253-256 (1994).
Tirosh et al., "Normal Fasting Plasma Glucose Levels and Type 2 Diabetes in Young Men" New England Journal of Medicine, 353(14):1454-62 (Oct. 2005).
UK Prospective Diabetes Study (UKPDS) Group 28: A randomized trial of efficacy of early addition of metformin in sulfonylurea-treated type 2 diabetes. Diabetes Care 1998; 21(1):87-92 (Jan. 1998).
UK Prospective Diabetes Study (UKPDS) Group, "Tight blood pressure control and risk of macrovascular and microvascular complications in type 2 diabetes (UKPDS 38)." BMJ 317:703-13 (Sep. 1998).
van Gaal et al., "Exploiting the antidiabetic properties of incretins to treat type 2 diabetes mellitus: glucagon-like peptide 1 receptor agonists or insulin for patients with inadequate glycemic control," European Journal of Endocrinology 158(6):773-84 (Jun. 2008).
van Gaal & De Leeuw, "Rationale and options for combination treatment of type 2 diabetes." Diabletologia 46(Supplement 1):M44-M50 (Mar. 2003).
Vilsboll et al., "Liraglutide, a long-acting human glucagon-like peptide-1 analog, given as monotherapy significantly improves glycemic control and lowers body weight without risk of hypoglycemia in patients with type 2 diabetes." Diabetes Care 30(6):1608-10 (Jun. 2007; Epub Mar. 19, 2007).
wahlin-Boll et al., "Impaired effect of sulfonylurea following increased dosage." Eur J Clin Pharmacol 22(1):21-25 (1982).
Weir "Glucagon-like peptide-1 (7-37) actions on endocrine pancreas." Diabetes 38(3):338-42 (Mar. 1989).
Kelly et al., "Systematic review: glucose control and cardiovascular disease in type 2 diabetes." Ann Intern Med 151(6):394-403 (Sep. 2009; Epub Jul. 20, 2009).
Kendall et al., "Clinical Application of Incretin-Based Therapy: Therapeutic Potential, Patient Selection and Clinical Use." European Journal of Internal Medicine. 20(Suppl 2):S329-39 (Jul. 2009).
Khaw et al., "Glycated haemoglobin, diabetes, and mortality in men in Norfolk cohort of European Prospective Investigation of cancer and Nutrition (EPIC Norfolk)." BMJ 322(7277)15-18 (Jan. 2001).
Kim et al., "Retinopathy in Monkeys with Spontaneous Type 2 Diabetes" Investigative Opth & Visual Science, 45(12):4543-53 (Dec. 2004).
King et al., Global burden of diabetes, 1995-2025. Prevalence, numerical estimates and projections. Diabetes Care 21(9)1414-31 (Sep. 1998).
Kolotkin et al., "Assessing impact of weight on quality of life." Obes Res. 3(1):49-56 (Jan. 1995).
Kolotkin et al., "Development of a brief measure to assess quality of life in obesity." Obes Res. 9(2):102-11 (Feb. 2001).
Compa-rbeB B.A. Me-roipmeckme yka3amici, May 5, 2010,c. 5 (Kondrat'ev V.A. Methodical Guidelines, May 7, 2010, p. 5)], found on Mar. 24, 2016, found from Internet: StudFields.ru>preview/4510743) English translation submitted.
Korytkowski, "When oral agents fail: practical barriers to starting insulin." Int J Obes Relat Metab Disord. 26 Suppl 3:S18-24 (Sep. 2002).
Lantus® Drug Description, downloaded Nov. 12, 2015, one page.
Lepore et al., "Pharmacokinetics and pharmacodynamics of subcutaneous injection of long-acting human insulin analog glargine,

(56) References Cited

OTHER PUBLICATIONS

NPH insulin, and ultralente human insulin and continuous subcutaneous infusion of insulin lispro." Diabetes 49(12):2142-48 (Dec. 2000).
Lovshin & Drucker, "Incretin-based therapy for type 2 diabetes mellitus." Nat. Rev. Endocrinol. 5(5):262-69 (May 2009).
MacConell et al., "Exenatide resulted in significantly greater improvements in posprandial glycaemic control compared to sitagliptin," Diabetologia 51(Supplement 1) p. S348, Abstract 872, one page (2008).
Mainous et al., "Impact of the population at risk of diabetes on projections of diabetes burden in the United States: an epidemic on the way." Diabetologia 50(5):934-40 (May 2007; Epub Nov. 21, 2006).
Madsbad, "Impact of postprandial glucose control on diabetes-related complications: How is the evidence evolving?" Journal of Diabetes and Its Complications, 30:374-85 (2016; available online Oct. 9, 2015).
Matthews et al., "Homeostasis model assessment: insulin resistance and β-cell function from fasting plasma glucose and insulin concentrations in man." Diabetologia 28(7):412-419 (Jul. 1985).
McFarlane, "Insulin therapy and type 2 diabetes: management of weight gain," J Clin Hypertens (Greenwich). 11(10):601-7 (Oct. 2009).
Meadows et al, "The diabetes health profile (DHP): a new instrument for assessing the psychosocial profile of insulin equiring patients: development and psychometric evaluation," Qual. Life Res. 5(2):242-54 (Apr. 1996).
Meadows et al., "Adaptation of the diabetes health profile (DHP-1) for use with patients with Type 2 diabetes mellitus: psychometric evaluation and cross-cultural comparison," Diabet. Med. 17(8):572-80 (Aug. 2000).
Meigs et al., "Body Mass Index, Metabolic Syndrome, and Risk of Type 2 Diabetes or Cardiovascular Disease" Journal of Clinical Endocrinology & Metabolism, 91(8):2906-12 (Aug. 2006).
Meier et al., "Effect of lixisenatide vs liraglutide on glycaemic control, gastric emptying and safety parameters in optimised insulin glargine type 2 diabetes mellitus +/- metformin" Poster and Abstract 926, 50th EASD Annual Meeting, Vienna, Austria Sep. 15-19, 2014, pp. 1-3.
Meier et al., "Contrasting Effects of Lixisenatide and Liraglutide on Postprandial Glycemic Control, Gastric Emptying, and Safety Parameters in Patients With Type 2 Diabetes on Optimized Insulin Glargine With or Without Metformin: A Randomized, Open-Label Trial" Diabetes Care 38(7):1263-73 (Jul. 2015).
Merck Index, "Metformin", The Merck Index, 15th Edition (2013), RSC Publishing, 4 pages submitted, p. 1102.
Miller et al., "Type 2 diabetes in the child and adolescent", In: Lifshitz F (ed) Pediatric Endocrinology: 5th edition, vol. 1, New York, Marcel Dekker, pp. 169-188 (2007).
Miyazaki et al., "Improved glycemic control and enhanced insulin sensitivity in type 2 diabetic subjects treated with pioglitazone", Diabetes Care, 24(4):710-19 (Apr. 2001).
Monnier & Colette, "Addition of rapid-acting insulin to basal insulin therapy in type 2 diabetes: indications and modalities." Diabetes Metab 32(1):7-13 (Feb. 2006).
Monnier et al., "Contribution of fasting and postprandial plasma glucose increments to the overall diurnal hyperglycemia of type 2 diabetic patients: variations with increasing levels of HbA1c." Diabetes Care 26(3):881-85 (Mar. 2003).
Monnier et al., "Postprandial and Basal Glucose in Type 2 Diabetes: Assessment and Respective Impacts" Diabetes Technology & Therapeutics, 13(Supplement 1):S25-S32 (2011).
Mudaliar & Edelman, "Insulin therapy in type 2 diabetes." Endocrinol Metab Clin North Am. 30(4):935-82 (Dec. 2001).
Nathan et al., "Medical Management of Hyperglycemia in Type 2 Diabetes: A Consensus Algorithm for the Initiation and Adjustment of Therapy" Diabetes Care 32(1):193-203 (Jan. 2009).
Nathan et al., "Modern-day clinical course of type 1 diabetes mellitus after 30 years' duration: the diabetes control and complications trial/epidemiology of diabetes interventions and complications and Pittsburgh epidemiology of diabetes complications experience (1983-2005)." Arch Intern Med. 169(14):1307-16 (Jul. 2009).
Nathan et al., "Medical Management of Hyperglycemia in Type 2 Diabetes: A Consensus Algorithm for the Initiation and Adjustment of Therapy. A Consensus statement of the American Diabetes Association and the European Association for the Study of Diabetes." Diabetes Care 31(1):173-75 (Jan. 2008).
Nathan et al., "Translating the A1c Assay Into Estimated Average Glucose values." Diabetes Care 31(8):1473-78 (Aug. 2008; Epub Jun. 7, 2008).
Nauck et al., "Effects of Glucagon-Like Peptide 1 on Counterregulatory Hormone Responses, Cognitive Functions, and Insulin Secretion during Hyperinsulinemic, Stepped Hypoglycemic Clamp Experiments in Healthy Volunteers." Journal of Clin. Endocrinol.& Metab. 87(3):1239-46 (Mar. 2002).
Nauck et al., "Efficacy and safety of the dipeptidyl peptidase-4 inhibitor, sitagliptin, compared with the sulfonylurea, glipizide, in patients with type 2 diabetes inadequately controlled on metformin alone: a randomized, double-blind, non-inferiority trial," Diabetes, Obesity and Metabolism, 9(2):194-205 (Mar. 2007).
NCT00976937, ClinicalTrials.gov, "24-week Study Comparing Lixisenatide (AVE0010) to Sitagliptin as add-on to Metformin in Obese Type 2 Diabetic Patients Younger Than 50," last updated Mar. 10, 2014, Retrieved Aug. 31, 2016, pp. 1-5.
NCT00866658 ClinicalTrials.gov, "GLP-1 agonist AVE0010 in patients with type 2 diabetes for glycemic control and safety evaluation, on top of basil insulin +/- sulfonylurea" p. 1-3, accessed Mar. 16, 2016 (updated Jan. 19, 2010).
NCT01169779, Clinical Trials.gov, "Efficacy and Safety of Lixisenatide in Patients with Type 2 diabetes mellitus insufficiently controlled by metformin," pp. 1-3, accessed Mar. 16, 2016 (updated Mar. 28, 2011).
NCT00713830, Clinical Trials.gov "GLP-1 Agonist in Patients with Type 2 Diabetes for Glycemic Control and Safety Evaluation, on Top of Sulfonylurea" pp. 1-3, accessed Mar. 16, 2016 (updated Jul. 13, 2008).
NICE, National Institute for Health and Care Excellence, "Evidence summary: new medicine, ESNM26: Type 2 diabetes: lixisenatide; Key points from the evidence" pp. 1-26 (Sep. 24, 2013).
NIH, National Institute of Diabetes and Digestive and Kidney Disease, "Hypoglycimia" pp. 1-8, accessed Mar. 16, 2016.
Nihonn-Iyakuhin-shu Iryoyaku "Pioglitazone hydrochloride, Insulin sensitizing hypoglycemic agent" 2009 Edition, Jiho Inc. p. 1901 (2009).
Nilsson et al., "Effects of GI vs content of cereal fibre of the evening meal on glucose tolerance at a subsequent standardized breakfast." Eur. J Clin Nutr. 62:712-20 (2008; epub May 23, 2007).
Nowels et al., "Validation of the EQ-50 quality of life instrument in patients after myocardial infarction." Qual Life Res 14(1):95-105 (Feb. 2005).
Ohkubo et al., "Intensive insulin therapy prevents the progression of diabetic microvascular complications in Japanese patients with non-insulin-dependent diabetes mellitus: a randomized prospective 6-year study." Diabetes Res Clin Pract 28(2):103-17 (May 1995).
Olansky "Do incretin-based therapies cause acute pancreatitis?" J Diabetes Technol. 4(1):228-29 (Jan. 2010).
Osterbye et al., "Sulfatide promotes the folding of proinsulin, preserves insulin crystals, and mediates its nonomerization." Glycobiology 11(6):473-79 (Jun. 2001).
Paniker et al., "Beneficial effects of triple drug combination of pioglitazone with glibenclamide and metformin in type 2 diabetes mellitus patients on insulin therapy," J Assoc Physicians India, 51:1061-64 (Nov. 2003).
Park et al., "Long-term treatment of glucagon-like peptide-1 analog exendin-4 ameliorates diabetic nephropathy through improving metabolic anomalies in db/db mice." J Am Soc Nephrol, 18(4):1227-38 (Apr. 2007; Epub Mar. 14, 2007).
Patel et al., "Stability Considerations for Biopharmaceuticals: Overview of Protein and Peptide Degradation Pathways" Available online at: http://www.bioprocessint.com/manufacturing/formulation/biopharmaceutical-product-stability-considerations-part-1/, 23 pages (Jan. 2011).

(56) References Cited

OTHER PUBLICATIONS

18th World Health Congress (Helsinki). WMA Declaration of Helsinki—Ethical Principles for Medical Research Involving Human Subjects; WMA; Jun. 1964, pp. 1-8.
Abbas T., et al., "Impairment of Synaptic Plasticity and Memory formation in GLP-1 Receptor Ko Mice: Interaction Between Type 2 Diabetes and Alzheimer's Disease," Behavioural Brain Research, 2009, vol. 205 (1), pp. 265-271.
Action to Control Cardiovascular Risk in Diabetes Study Group, "Effects of Intensive Glucose Lowering in Type 2 Diabetes," The New England Journal of Medicine, 2008, vol. 358 (24), pp. 2545-2559.
Actrapid® prescribing information, Apr. 2011, pp. 1-4.
Actrapid® summary of product characteristics, Apr. 2011, pp. 1-11.
Aderinwale O.G., et al., "Current Therapies and New Strategies for the Management of Alzheimer's Disease," American Journal of Alzheimer's Disease and Other Dementias, 2010, vol. 25 (5), pp. 414-424.
Agholme L., et al., "An in Vitro Model for Neuroscience: Differentiation of SH-SY5Y Cells into Cells with Morphological and Biochemical Characteristics of Mature Neurons," Journal of Alzheimer's Disease, 2010, vol. 20, pp. 1069-1082.
Ahren et al., Abstract "Efficacy and Safety of Lixisenatide QD Morning and Evening Injections vs Placebo in T2DM Inadequately Controlled on Metformin (GetGoal-M)" Oral presentation O-0591 presented at the World Diabetes Congress in Dubai, Dec. 5-8, 2011, one page.
Ahualli J., "The Double Duct Sign," Radiology, 2007, vol. 244 (1), pp. 314-315.
Abraira et al., "Glycaemic separation and risk factor control in the Veterans Affairs Diabetes Trial: an interim report." Diabetes Obes Metab 11(2):150-56. (2009; Epub Jul. 29, 2008).
Aguilar, "Heart failure and diabetes: Time to pay attention" American Heart Journal, 162(5):795-97 (Nov. 2011).
Ahmad & Swann, and Bloomgren "Exenatide and rare adverse events." N Engl J Med 358(18):1969-72 (May 2008).
Albert-Ludwigs University Freiburg, Institute fur Medizinische Biometrie and Statistik "Non-Inferiority Trials" dated Mar. 29, 2017, one page.
American Diabetes Association, "Type 2 diabetes in children and adolescents." Diabetes Care 23(3):381-89 (Mar. 2000).
American Diabetes Association, "Standards of Medical Care in Diabetes-2011", Diabetes Care, 34 (Supplement 1): S11-S61 (Jan. 2011).
American Diabetes Association, "Diagnosis and Classification of Diabetes Mellitus", Diabetes Care, 37 (Supplement 1):S81-S90 (Jan. 2014).
American Diabetes Association Annual Scientific Sessions, "New Diabetes Compound AVE0010 Showed Clear Dose Response Results With Once-A-Day Injection in Phase IIb Study", published Jun. 9 2008, two pages.
American Diabetes Association, "Standards of Medical Care in Diabetes." Diabetes Care 28(Supplement 1): S4-S36 (Jan. 2005).
American Diabetes Association, "Standards of Medical Care in Diabetes 2008." Diabetes Care 31(Supplement 1):S12-S54.
Ampudia-Blasco et al., "Basal Plus Basal-Bolus approach in type 2 diabetes." Diabetes Technol Ther. 13 Suppl 1: S75-83 (Jun. 2011).
Aquiliante, "Sulfonylurea pharmacogenomics in type 2 diabetes: the influence of drug target and diabetes risk polymorphisms" Expert Rev Cardiovasc Ther. 8(3):359-72 (Mar. 2010).
Atkinson et al., "Validation of a general measure of treatment satisfaction, the Treatment Satisfaction Questionnaire for Medication (TSQM), using a national panel study of chronic disease." Health Qual Life Outcomes. 2:12, pp. 1-13 (Feb. 2004).
Bastyr et al., "Therapy focused on lowering postprandial glucose, not fasting glucose, may be superior for lowering HbA1c. IOEZ Study Group." Diabetes Care 23(9):1236-41 (Sep. 2000).
Beckman et al., "Diabetes and atherosclerosis: epidemiology, pathophysiology, and management." JAMA 287(19):2570-81 (May 2002).
Bell et al., "Sequence of the human insulin gene." 284(5751):26-32 (Mar. 1980).
Bennett, "Impact of the new WHO classification and diagnostic criteria." Diabetes Obes Metab 1(Supplement 2):S1-S6 (1999).
Bentley-Lewis et al., "Rationale, design, and baseline characteristics in Evaluation of LIXisenatide in Acute Coronary Syndrome, a long-term cardiovascular end point trial of lixisenatide versus placebo" American Heart Journal, 169(5):631-38 (May 2015; Epub Feb. 11, 2015).
Brazier et al., "Testing the validity of the Euroqol and comparing it with the SF-36 health survey questionnaire." Qual Life Res 2(3):169-80 (Jun. 1993).
Buse et al., "Effects of exenatide (Exendin-4) on glycemic control over 30 weeks in sulfonylurea-treated patients with type 2 diabetes." Diabetes Care 27(11):2628-35 (Nov. 2004).
Byetta® Labeling Revision, pp. 1-24 (Jan. 11, 2008).
Byetta® European Public Assessment Report (EPAR), pp. 1-36 (Feb. 16, 2012).
Byetta® Prescribing Information, pp. 1-34 (Revised Oct. 2009).
Byetta® Summary of Product Characteristics. Annex I, pp. 1-71, (2011).
Byetta® Product information—EMA, pp. 1-2 (Jun. 10, 2016).
Canadian Cardiovascular Society Grading of Angina Pectoris. From http://www.sscts.org/pages/classificationanginaccs.aspx. Accessed May 27, 2016, one page.
Canadian Diabetes Association. Clinical Practice Guidelines Expert Committee. Canadian Diabetes Association 2008. Clinical Practice Guidelines for the Prevention and Management of Diabetes in Canada. Canadian Journal of Diabetes S162-S167 (2008).
Cannon et al. For the Pravastatin or Atorvastatin Evaluation and Infection Therapy-Thrombolysis in Myocardial Infarction Investigators. "Intensive versus Moderate Lipid Lowering with Statins after Acute Coronary Syndromes." N Engl J Med 350(15):1495-504 (Apr. 2004; Epub Mar. 8, 2004).
Centers for Disease Control and Prevention. National diabetes fact sheet: general information and national estimates on diabetes in the United States, 2001 Rev ed. Atlanta, GA: U.S. Department of Health and Human Services, Centers for Disease Control and Prevention, pp. 1-8, 2004.
Charbonnel et al., "Efficacy and safety of the dipeptidyl peptidase-4 inhibitor sitagliptin added to ongoing metformin therapy in patients with type 2 diabetes inadequately controlled with metformin alone." Diabetes Care 29(12):2638-43 (Dec. 2006).
Classification of Functional Capacity and Objective Assessment, My.AmericanHeart, 1994—last accessed Oct. 23, 2015, pp. 1-2.
Clinical Trials History for Trial No. NCT00688701 last updated Mar. 25, 2014. Accessed at https://clinicaltrials.gov/archive/NCT00688701 Accessed on Jun. 2, 2016, pp. 1-2 submitted.
Clinical Trials Archive for Trial No. NCT00688701 updated Sep. 30, 2012. Accessed at: https://clinicaltrials.gov/archive/NCT00688701/2012_09_30/changes Accessed on Jun. 2, 2016, pp. 1-5 submitted.
Coutinho et al., "The relationship between glucose and incident cardiovascular events. A metaregression analysis of published data from 20 studies of 95,783 individuals followed for 12.4 years." Diabetes Care 22(2):233-40 (Feb. 1999).
D'Alessio et al., "The role of dysregulated glucagon secretion in type 2 diabetes" Diabetes, Obesity and Metabolism, 13(Supppl. 1):126-132 (Oct. 2011).
Das et al., "The British Cardiac Society Working group definition of myocardial infarction: implications for practice." Heart 92(1):21-6 (Jan. 2006; Epub Apr. 14, 2005).
DCCT, Diabetes Control and Complications Trial/ Epidemiology of Diabetes Interventions and Complications Research Group: Intensive diabetes therapy and carotid intima-media thickness in type 1 diabetes. N Engl J Med 348(23):2294-303 (Jun. 2003).
DCCT, Diabetes Control and Complications Trial/ Epidemiology of Diabetes Interventions and Complications Research Group: Intensive diabetes treatment and cardiovascular disease in patients with type 1 diabetes. N Engl J Med. 353(25):2643-59 (Dec. 2005).
Definition of Phase, Clinical Trials.gov NIH, accessed Mar. 16, 2016, one page.

(56) References Cited

OTHER PUBLICATIONS

Definition of "Combination", Concise Oxford English Dictionary, edited by A. Stevenson and M. Waite, Oxford University press, 12th Edition, Aug. 2011, 4 pages submitted, see p. 285.
Definition of "prevent" Dictionary.com; last accessed Sep. 29, 2016, pp. 1-6.
Definition of "induce" Dictionary.com; last accessed Sep. 29, 2016, pp. 1-6.
Degn et al., "Effect of Intravenous Infusion of Exenatide (Synthetic Exendin-4) on Glucose-Dependent Insulin Secretion and Counter-regulation During Hypoglycemia." Diabetes 53(9):2397-2403 (Sep. 2004).
de la Loge et al., "Cross-cultural development and validation of a patient self-administered questionnaire to assess quality of life in upper gastrointestinal disorders: The PAGI-QOL." Quality of Life Research 13(10):1751-62 (Dec. 2004).
De Lemos et al., "Early intensive vs. a delayed conservative simvastatin strategy in patients with acute coronary syndromes: phase Z of the A to Z trial." JAMA 292(11):1307-16 (Sep. 2004; Epub Aug. 30, 2004).
Del Prato & Tiengo, "The importance of first-phase insulin secretion: implications for the therapy of type 2 diabetes mellitus." Diabetes Metab Res Rev. 17(3):164-74 (May-Jun. 2001).
Del Prato et al., "Global Partnership for Effective Diabetes Management. Tailoring treatment to the individual in type 2 diabetes practical guidance from the Global partnership for effective diabetes managment." Int J Clin Pract. 64(3):295-304 (Feb. 2010).
DeWitt & Hirsch, "Outpatient insulin therapy in type 1 and type 2 diabetes mellitus: scientific review." JAMA 289(17):2254-64 (May 2003).
De Venciana et al., "Postprandial versus preprandial blood glucose monitoring in women with gestational diabetes mellitus requiring insulin therapy." N Engl J Med 333(19):1237-41 (Nov. 1995).
Dinneen & Gerstein, "The association of microalbuminuria and mortality in non-insulin dependent diabetes mellitus. A systematic overview of the literature." Arch Intern Med 157(13):1413-8 (Jul. 1997).
Dolan, "Modeling valuations for EuroQol health states." Med Care 35(11):1095-1108 (Nov. 1997).
Dombrowsky & Barrett, "Type II diabetes mellitus in children: Analysis of prevalence based on the pediatric heath information system (PHIS) database" American College of Clinical Pharmacology Annual Meeting, Bethesda, Maryland (Sep. 22-24, 2013).
Donahue et al., "Postchallenge glucose concentration and coronary heart disease in men of Japanese ancestry. Honolulu Heart Program." Diabetes 36(6):689-92 (Jun. 1987).
Druet et al., "Characterization of insulin secretion and resistance in type 2 diabetes of adolescents." J Clin Endocrinol Metab 91(2):401-404 (Feb. 2006; epub Nov. 15, 2005).
Dunning & Gerich, "The Role of alpha-cell Dysregulation in Fasting and Postprandial Hyperglycemia in Type 2 Diabetes and Therapeutic Implications" Endocrine Reviews 28(3):253-83 (Apr. 2007).
Eckert et al., "Assessingthe progression of Parkinson's disease: A metabolic network approach," Lancet Neurol. 6(10):926-32 (Oct. 2007).
Encyclopedia of Drugs, "Metformin" Moscow, Drug Register of 2001, p. 549, English translation provided pp. 1-2.
European Medicines Agency, "Toujeo (previously Optisulin) insulin glargine," <http://www.ema.europa.eu/ema/index.jsp?curl=pages/medicines/human/medicines/000309/human_med_000955.jsp&mid=WC0b01ac058001d124>, last updated Jan. 25, 2016, visited Feb. 3, 2016, pp. 1-6—screenshot of "About" tab of webpage and printouts of "About" tab of webpage with listed items collapsed and expanded.
European Medicines Agency, Committee for Medicinal Products for Human Use (CHMP), "Assessment report-Lyxumia", pp. 1-81 (Nov. 28, 2012).
European Medicines Agency, "Note for guidance on non-clinical safety studies for the conduct of human clinical trials and marketing authorization for pharmaceuticals" pp. 1-22 (Jul. 2008).

European Medicines Agency, "Guideline on clinical investigation of medicinal products in the treatment of hypertension" (EMA/238/1995 Rev 3) pp. 1-18 (Nov. 18, 2010).
European Diabetes Policy Group, "A desktop guide to Type 2 diabetes mellitus." Diabetic Medicine 16(9):716-730 (1999).
EuroQol Group, "EuroQol—a new facility for the measurement of health-related quality of life." Health policy (Amsterdam, Netherlands) 16(3):199-208 (Dec. 1990).
Faichney, "Metformin in Type 1 diabetes: Is This a Good or Bad Idea?" Diabetes Care 26(5):1655 (May 2003).
FDA, Food and Drug Administration. Guidance for Industry—Diabetes Mellitus: Developing Drugs and Therapeutic Biologics for Treatment and Prevention. pp. 1-34 (Feb. 2008).
FDA—Food and Drug Administration, CFR—Code of Federal Regulations Title 21, Chapter 1, Subchapter D, Part 312.21, "Phases of an investigation" pp. 1-2, Apr. 1, 2015.
Forlenza et al., "Diagnosis and biomarkers of predementia in Alzheimer's disease," BMC Medicine 8:89 pp. 1-14 (Dec. 2010).
Forman et al., "Higher levels of albuminuria within the normal range predict incident hypertension." J Am Soc Nephrol 19(10):1983-88 (Oct. 2008).
Game "Novel hypoglycaemic agents: Considerations in patients with chronic kidney disease" Nephron Clin Pract. 126(1):14-18 (Jan. 11, 2014).
GenBank: AAP20099.1 "Interferon Alpha 2B [*Homo sapiens*]" dated Apr. 30, 2003; accessed Jan. 18, 2017, one page.
GenBank: AAA59149.1 "Interleukin 4 [*Homo sapiens*]" dated Jan. 6, 1995; accessed Jan. 18, 2017, one page.
GenBank: AAA52578.1 "GM-CSF [*Homo sapiens*]" dated Nov. 8, 1994; accessed Jan. 18, 2017, one page.
Gerich, "Insulin glargine: long-acting basal insulin analog for improved metabolic control." Curr Med Res Opin. 20(1):31-37 (Jan. 2004).
Gerstein et al., "Albuminuria and risk of cardiovascular events, death, and heart failure in diabetic and nondiabetic individuals." JAMA 286(4):421-6 (Jul. 2001).
Giacometti et al., "In vitro activity of the histatin derivative P-113 against multidrug-resistant pathogens responsible for pneumonia in immunocompromised patients." 49(3):1249-52 (Mar. 2005).
Giorda et al., "Pharmacokinetics, safety, and efficacy of DPP-4 inhibitors and GLP-1 receptor agonists in patients with type 2 diabetes mellitus and renal or hepatic impairment. A systematic review of the literature." Endocrine 46(3):406-19 (Aug. 2014; epub Feb. 8, 2014).
Glucophage XR, Product Information, Bristol-Meyers Squibb Company (Jan. 2009).
Groop et al., "Dose-dependent effects on glyburide on insulin secretion and glucose uptake in humans." Diabetes Care 14(8):724-27 (Aug. 1991).
Groop, "Sulfonylureas in NIDDM." Diabetes Care 15(6):737-54 (Jun. 1992).
Gromada et al., "Alpha-Cells of the Endocrine Pancreas: 35 Years of Research but the Enigma Remains" Endocrine Reviews 28(1):84-116 (Jan. 2007).
Halimi, "DPP-4 inhibitors and GLP-1 analogues: for whom? Which place for incretins in the management of type 2 Diabetic patients?", Diabetes & Metabolism 34(Supplement 2):S91-S95 (Feb. 2008).
Harkavyi & Whitton, "Glucagon-like peptide 1 receptor stimulation as a means of neuroprotection" British Journal of Pharmacology 159(3):495-501 (2010; Epub Jan. 29, 2010).
Hasslacher et al., "Diabetic kidney disease" Exp and Clin Endocrinol Diabetes 122(7):391-94 (Jul. 2014).
Heine & Dekker, "Beyond postprandial hyperglycemia: metabolic factors associated with cardiovascular disease." Diabetologia 45(4):461-75 (Apr. 2002).
Heine et al., "Exenatide versus insulin glargine in patients with suboptimally controlled type 2 diabetes." Ann Intern Med. 143(8):559-69 (Oct. 2005).
Hillier & Pedula, "Characteristics of an adult population with newly diagnosed Type 2 Diabetes. The relation of obesity and age of onset." Diabetes Care 24(9):1522-27 (Sep. 2001).

(56) References Cited

OTHER PUBLICATIONS

Hinnen, "Therapeutic Options for the Management of Postprandial Glucose in Patients With Type 2 Diabetes on Basal Insulin" Clinical Diabetes 33(4):175-80 (2015).
Hollander & Kushner, "Type 2 Diabetes Comorbidities and Treatment Challenges: Rationale for DPP4-Inhibitors" Postgraduate Medicine, 122(3):71-80 (May 2010).
Holman et al., "Three-year efficacy of complex insulin regimens in type 2 diabetes." N Engl J Med. 361(18):1736-47 (Oct. 2009; Epub Oct. 22, 2009).
Hubschle et al., "Anti-atherosclerotic activity of lixisenatide in ApoE knockout mice" Abstract 809, Diabetologia, 55(Supplement 1):S334 (Oct. 2012).
IDF Clinical Guidelines Task Force. Global guideline for Type 2 diabetes. Brussels: International Diabetes Federation, pp. 1-82 (Aug. 2005).
IDF, International Diabetes Federation Guideline Development Group, "Guideline for management of postmeal glucose in diabetes" Diabetes Res Clin Pract, pp. 1-13, (2012).
Inzucchi et al., "Management of hyperglycaemia in type 2 diabetes: a patient-centered approach. Position statement of the American Diabetes Association (ADA) and the European Association for the Study of Diabeters (EASD)." Diabetologia. 55(6):1577-96 (Jun. 2012; Epub Apr. 20, 2012).
Janka et al., "Comparison of basal insulin added to oral agents versus twice-daily premixed insulin as initial insulin therapy for type 2 diabetes." Diabetes Care 28(2):254-59 (Feb. 2005).
Januvia—EPAR Summary for the Public, pp. 1-3 (Aug. 2012).
Johnson et al., "Diabetes, Insulin Resistance, and Metabolic Syndrome in Horses" Journal of Diabetes Science and Technology, 6(3):534-40 (May 2012).
Jones et al., "Effect of metformin in pediatric patients with type 2 diabetes: a randomized controlled trial." Diabetes Care 25(1):89-94 (Jan. 2002).
Juniper et al., "Determining a minimal important change in a disease-specific quality of life questionnaire." J Clin Epidemiol 47(1):81-87 (Jan. 1994).
Karasik et al., "Sitagliptin, a DPP-4 inhibitor for the treatment of patients with type 2 diabetes: a review of recent clinical trials," Current Medical Research and Opinion 24(2):489-96 (Jan. 2008).
Katz et al., "The clinical burden of type 2 diabetes in patients with acute coronary syndromes: Prognosis and Implications for short- and long-term management" Diabetes and Vascular Disease Research, 11(6):395-409 (Nov. 2014).
U.S. Appl. No. 15/595,929, filed May 15, 2017, Pharmaceutical Composition Comprising a GLP-1-Agonist and Methionine, pending.
U.S. Appl. No. 15/275,867, filed Sep. 26, 2016, Method of Treatment of Diabetes Type 2 Comprising Add-On Therapy to Insulin Glargine and Metformin, US 20170136094, pending.
U.S. Appl. No. 15/237,285, filed Aug. 15, 2016, Use of AVE0010 for the Treatment of Diabetes Mellitus Type 2, US 2017/0119852, pending.
U.S. Appl. No. 15/197,378, filed Jun. 29, 2016, Pharmaceutical Combination for Use in Glucemic Control in Diabetes Type 2 Patients, US 2017/0143801, pending.
U.S. Appl. No. 15/657,683, filed Jul. 24, 2017, Insulin glargine/lixisenatide fixed ratio formulation, pending.
U.S. Appl. No. 15/646,760, filed Jul. 11, 2017, Treatment Type 2 Diabetes Mellitus Patients, pending.
U.S. Appl. No. 15/146,255, filed May 4, 2016, Pharmaceutical Composition for Use in the Treatment of a Neurodegenerative Disease, US 2016/0354445, pending.
U.S. Appl. No. 15/411,557, filed Jan. 20, 2017, Prevention of Hypoglycemia in Diabetes Mellitus Type 2 Patients, pending.
U.S. Appl. No. 15/144,270, filed May 2, 2016, Prevention of Hypoglycemia in Diabetes Mellitus Type 2 Patients, US 2017/0080057, pending.
Ahren, "GLP-1 for type 2 diabetes", Experimental Cell Research, 317(9):1239-45 (Jan. 2011).
American Diabetes Association, "Standards of Medical Care in Diabetes—2017" Diabetes Care 40(Supplement 1):S1-S142 (Jan. 2017).
Berard et al., "Canadian Diabetes Association 2008 Clinical Practice Guidelines for the Prevention and Management of Diabetes in Canada." Canadian Journal of Diabetes 32(Supplement 1):1-215 (Sep. 2008).
Bergenstal et al., "Type 2 Diabetes: Assessing the Relative Risks and Benefits of Glucose-lowering Medications" The American Journal of Medicine 123(4):e9-e18 (Apr. 2010).
Bucceri et al., "Gallbladder and gastric emptying: relationship to cholecystokininemia in diabetics." Eur. J. Intern. Med. 13(2):123-28 (Mar. 2002).
Byetta® Summary of Product Characteristics, updated Jul. 22, 2016, last accessed Jul. 31, 2017, pp. 1-13.
Definition of "reduce" Dictionary.com; last accessed Aug. 13, 2017, pp. 1-4.
Godoy-Matos, "The role of glucagon on type 2 diabetes at a glance," Diabetology & Metabolic Syndrome 6:91, pp. 1-5 (Aug. 2014).
Home et al., "Management of type 2 diabetes: updated NICE guidance" BMJ 336: 1306-1308 (Jun. 2008).
Ismail-Beigi et al., "Individulaizing Glycemic Targets in Type 2 Diabetes Mellitus: Implications of Recent Clinical Trials" Annals of Internal Medicine 154(8):554-559 (Apr. 2011).
Lawson et al., "Coordination of gastric and gallbladder emptying after ingestion of a regular meal." Gastroenterology. 85(4):866-70 (Oct. 1983).
Lee et al., "Goals of Glycemic Control in Frail Older Patients with Diabetes" JAMA 305(13):1350-51 (Apr. 2011).
Nathan et al., "Medical Management of Hyperglycemia in Type 2 Diabetes: A Consensus Algorithm for the Initiation and Adjustment of Therapy" Diabetologia 52:17-30 (2009: Epub Oct. 22, 2008).
NCT00866658 ClinicalTrials.gov, "GLP-1 agonist AVE0010 in patients with type 2 diabetes for glycemic control and safety evaluation, on top of basal insulin +/− sulfonylurea" p. 1-3, accessed Mar. 16, 2016 (updated Aug. 3, 2010).
NICE, National Institute for Health and Care Excellence, "Type 2 diabetes in adults: management" pp. 1-45 (Dec. 2, 2015).
Rodbard et al., "Statement by an American Association of Clinical Endocrinologists/American College of Endocrinology Consensus Panel on Type 2 Diabetes Mellitus: An Algorithm for Glycemic Contra" Endocrine Practice 15(6):540-59 (Sep./Oct. 2009).
Sanofi-aventis Press Release, "Once Daily Lixisenatide in Combination with Basal Insulin Demonstrates Significant Improvement in Glucose Control" Paris, France (Sep. 30, 2010) pp. 1-3.
Sutter Medical Foundation, "Type 2 Diabetes Adult Outpatient Insulin Guidelines" Feb. 2011, pp. 1-6.
Non-Final Rejection issued in U.S. Appl. No. 13/382,442; dated Sep. 20, 2017, pp. 1-28.
Non-Final Rejection issued in U.S. Appl. No. 15/197,378; dated Jun. 15, 2017, pp. 1-13.
U.S. Appl. No. 15/144,270, filed May 2, 2016, Silvestre et al.
U.S. Appl. No. 15/595,929, filed May 15, 2017, Brunner-Schwarz et al.
U.S. Appl. No. 15/275,867, filed Sep. 26, 2016, Silvestre et al.
U.S. Appl. No. 15/237,285, filed Aug. 15, 2016, Boka et al.
U.S. Appl. No. 15/411,557, filed Jan. 20, 2017, Boka et al.
U.S. Appl. No. 15/197,378, filed Jun. 29, 2016, Niemöller.
U.S. Appl. No. 15/657,683, filed Jul. 24, 2017, Souhami et al.
U.S. Appl. No. 15/646,760, filed Jul. 11, 2017, Roy et al.
U.S. Appl. No. 15/146,255, filed May 4, 2016, Hess et al.
Akbar D.H., "Sub-Optimal Postprandial Blood Glucose Level in Diabetics Attending the Outpatient Clinic of a University Hospital," Saudi Med Journal, 2003, vol. 24 (10), pp. 1109-1112.
American Diabetes Association (ADA) Committee Report—The Expert Committee on the Diagnosis and Classification of Diabetes Mellitus—Report of the Expert Committee on the Diagnosis and Classification of Diabetes Mellitus, Diabetes Care, 21(Supplement 1): S5-S19 (Jan. 1998).
Aoki K., et al., "Hydrolysis of Nonionic Surfactants," Annual Report Takeda Research Laboratory, 1968, vol. 27, pp. 172-176.
Apidra® prescribing information, Apr. 2012, pp. 1-6.

(56) References Cited

OTHER PUBLICATIONS

Arnolds et al., "Insulin Glargine (GLAR) plus Metformin (MET): An Efficacious and Safe Regimen that can be combined with Exenatide (EXE) or Sitagliptin (SITA)" Diabetes, 58(Suppl. 1): A141, Jun. 2009.
Arnolds S., et al., "Basal Insulin Glargine Vs Prandial Insulin Lispro in Type 2 Diabetes," Lancet, 2008, vol. 378 (9636), pp. 370-371.
Arnolds S., et al., "Further Improvement in Postprandial Glucose Control with Addition of Exenatide or Sitagliptin to Combination therapy with Insulin Glargine and Metformin—A Proof-of-Concept Study," Diabetes Care, 2010, vol. 33 (7), pp. 1509-1515.
Auerbach R., et al., "Angiogenesis Assays: Problems and Pitfalls," Cancer Metastasis Reviews, 2000, vol. 19 (1-2), pp. 167-172.
Bakaysa D.L., et al., "Physicochemical Basis for the Rapid Time-Action of Lysb28 Prob29-Insulin: Dissociation of a Protein-Ligand Complex," Protein science, 1996, vol. 5 (12), pp. 2521-2531.
Banks W.A., et al., "Brain Uptake of the Glucagon-Like Peptide-1 Antagonist Exendin(9-39) After intranasal Administration," The Journal of Pharmacology and Experimental Therapeutics, 2004, vol. 309 (2), pp. 469-475.
Barnett A., "Dosing of Insulin Glargine in the Treatment of Type 2 Diabetes," Clinical Therapeutics, 2007, vol. 29 (6), pp. 987-999.
Barnett A.H., et al., "Tolerability and Efficacy of Exenatide and Titrated Insulin Glargine in Adult Patients with Type 2 Diabetes Previously Uncontrolled with Metformin or a Sulfonylurea: A Multinational, Randomized, Open-Label, Two-Period, Crossover Noninferiority Trial," Clinical Therapeutics, 2007, vol. 29 (11), pp. 2333-2348.
Barnett A.H., "Insulin Glargine in the Treatment of Type 1 and Type 2 Diabetes," Vascular Health and Risk Management, 2006, vol. 2 (1), pp. 59-67.
Barnett A.H., "Lixisenatide: Evidence for its Potential Use in the Treatment of Type 2 Diabetes," Core Evidence, 2011, vol. 6, pp. 67-79.
Barnett R.O., et al., "Insulin Analogues," Lancet, 1997, vol. 349 (9044), pp. 47-51.
Behar J., et al., "Functional Gallbladder and Sphincter of Oddi Disorders," Gastroenterology, 2006, vol. 130 (5), pp. 1498-1509.
Beintema J.J., et al., "Molecular Evolution of Rodent Insulins," Molecular Biology and Evolution, 1987, vol. 4 (1), pp. 10-18.
Berger M., "Towards More Physiological Insulin Therapy in the 1990s a Comment," Diabetes Research and Clinical Practice, 1989, vol. 6 (4), pp. S25-S31.
Berlie H., et al., "Glucagon-Like Peptide-1 Receptor Agonists as Add-On therapy to Basal Insulin in Patients with Type 2 Diabetes: A Systematic Review," Diabetes, Metabolic Syndrome and Obesity: Targets and Therapy, 2012, vol. 5, pp. 165-174.
Berlinsulin® H prescribing information, Apr. 2012, pp. 1-4.
Berlinsulin® H summary of product characteristics, Apr. 2012, pp. 1-11.
Bertram L., et al., "The Genetics of Alzheimer Disease: Back to the Future," Neuron, 2010, vol. 68 (2), pp. 270-281.
Best, Mathmatics and Statistics pp. 1-39, 1988.
Bethel M.A., et al., "Basal Insulin Therapy in Type 2 Diabetes," The Journal of the American Board of the Family Practice, 2005, vol. 18 (3), pp. 199-204.
Bhatt N.P., et al., "Chemical Pathways of Peptide Degradation. I. Deamidation of Adrenocorticotropic Hormone," Pharmaceutical Research, 1990, vol. 7 (6), pp. 593-599.
Blanchard V., et al., "Time Sequence of Maturation of Dystrophic Neurites Associated with Abeta Deposits in APP/PS1 Transgenic Mice," Experimental Neurology, 2003, vol. 184, pp. 247-263.
Bland J.M., et al., "Measurement Error," British Medical Journal, 1996, vol. 312 (7047), pp. 1654.
Bolen S., et al., "Systematic Review: Comparative Effectiveness and Safety of oral Medications for Type 2 Diabetes Mellitus," Annals of Internal Medicine, 2007, vol. 147 (6), pp. 386-399.
Bolli et al., "Efficacy and safety of lixisenatide once-daily versus placebo in patients with type 2 diabetes mellitus insufficiently controlled on metformin (GetGoal-F1)." Presentation Abstract No. 784, EASD Meeting Sep. 12-16, 2014.
Bolli G.B., et al., "Efficacy and Safety of Lixisenatide once Daily Vs Placebo in People with Type 2 Diabetes Insufficiently Controlled on Metformin (Getgoal-F1)," Diabetic Medicine, 2014, vol. 31 ( 2), pp. 176-184.
Bolli G.B., "The Pharmacokinetic Basis of Insulin Therapy in Diabetes Mellitus," Diabetes Research and Clinical Practice, 1989, vol. 6 (4), pp. S3-15.
Boutajangout A., et al., "Characterisation of Cytoskeletal Abnormalities in Mice Transgenic for Wild-Type Human Tau and Familial Alzheimer's Disease Mutants of App and Presenilin-1," Neurobiology of Disease, 2004, vol. 15 (1), pp. 47-60.
Boutajangout A., et al., "Increased Tau Phosphorylation But Absence of formation of Neurofibrillary Tangles in Mice Double Transgenic for Human Tau and Alzheimer Mutant (M146L) Presenilin-1," Neuroscience Letters, 2002, vol. 318 (1), pp. 29-33.
Brange "Galenics of Insulin" 1987, p. 35-36.
Brange J., et al., "Chemical Stability of Insulin 3. Influence of Excipients, formulation, and Ph," Acta Pharmaceutics Nordica, 1992, vol. 4 (3), pp. 149-158.
Brange J., et al., "Design of Insulin Analogues for Meal-Related therapy," Journal of Diabetes and Its Complications, 1993, vol. 7 (2), pp. 106-112.
Brange J., et al., "Insulin Structure and Stability," Pharmaceutical Biotechnology, 1993, vol. 5, pp. 315-350.
Brange J., et al., "Monomeric Insulins and their Experimental and Clinical Implications," Diabetes Care, 1990, vol. 13 (9), pp. 923-954.
Brange J., et al., "Neutral Insulin Solutions Physically Stabilized by Addition of Zn2+," Diabetic Medicine, 1986, vol. 3, pp. 532-536.
Brange J., et al., "Toward Understanding Insulin Fibrillation," Journal of Pharmaceutical Sciences, 1997, vol. 86 (5), pp. 517-525.
Brod M., et al., "Adherence Patterns in Patients with Type 2 Diabetes on Basal Insulin Analogues: Missed, Mistimed and Reduced Doses," Current Medical Research and Opinion, 2012, vol. 28 (12), pp. 1933-1946.
Brod M., et al., "Examining Correlates of Treatment Satisfaction for injectable Insulin in Type 2 Diabetes: Lessons Learned from a Clinical Trial Comparing Biphasic and Basal Analogues," Health Quality of Life Outcomes, 2007, vol. 5, pp. 1-10.
Broderick J., et al., "Guidelines for the Management of Spontaneous intracerebral Hemorrhage in Adults," Circulation, 2007, vol. 116 (16), pp. e391-e413.
Brown J.B., et al., "Slow Response to Loss of Glycemic Control in Type 2 Diabetes Mellitus," American Journal of Managed Care, 2003, vol. 9 (3), pp. 213-217.
"Buffer" Oxford Dictionary of Biochemistry and Molecular Biology, Oxford University Press, 2001, p. 83.
Burgermeister W., et al., "The Isolation of Insuin from the Pancreas," Insulin, 1975, vol. Part 2, pp. 715-727.
Burke G.T., et al., "Nature of the B10 Amino Acid Residue Requirements for High Biological Activity of Insulin," International Journal of Peptide and Protein Research, 1984, vol. 23 (4), pp. 394-401.
Buse J.B., et al., "Use of Twice-Daily Exenatide in Basal Insulin-Treated Patients with Type 2 Diabetes: A Randomized, Controlled Trial," Annals of Internal Medicine, 2011, vol. 154 (2), pp. 103-112.
Byetta—Summary of Product Characteristics, updated Jan. 27, 2015, last accessed Apr. 18, 2015, pp. 1-12.
Byrne M.M., et al., "Inhibitory Effects of Hyperglycaemia on Fed Jejunal Motility: Potential Role of Hyperinsulinaemia," European Journal of Clinical Investigation, 1998, vol. 28 (1), pp. 72-78.
Cadario B., "Sitagliptin," Drug Information Perspectives, 2010, vol. 30 (4), pp. 1-8.
Campas C., et al., "Ave-0010 GLP-1 Receptor Agonist Treatment of Diabetes," Drugs of the Future, 2008, vol. 33 (10), pp. 838-840.
Campbell R.K., et al., "Insulin Glargine," Clinical Therapeutics, 2001, vol. 23 (12), pp. 1938-1957.
Casas C., et al., "Massive CA1/2 Neuronal Loss with Intraneuronal and N-Terminal Truncated Abeta42 Accumulation in a Novel Alzheimer Transgenic Model," American Journal of Pathology, 2004, vol. 165 (4), pp. 1289-1300.

(56) References Cited

OTHER PUBLICATIONS

Chancel, "Natixis Conference on Diabetes." Sanofi, Paris, pp. 1-23 (Nov. 8, 2011).
Charles M.A., et al., "Prevention of Type 2 Diabetes: Role of Metformin," Drugs, 1999, vol. 58 (Suppl 1), pp. 71-73.
Chatterjee S., et al., "Insulin Glargine and its Place in the Treatment of Types 1 and 2 Diabetes Mellitus," Expert Opinion on Pharmacotherapy, 2006, vol. 7 (10), pp. 1357-1371.
Chen Y.E., et al., "Tissue-Specific Expression of Unique mRNAs That Encode Proglucagon-Derived Peptides or Exendin 4 in the Lizard," The Journal of Biological Chemistry, 1997, vol. 272 (7), pp. 4108-4115.
Cheung Y.T., et al., "Effects of All-Trans-Retinoic Acid on Human SH-SY5Y Neuroblastoma as in Vitro Model in Neurotoxicity Research," Neurotoxicology, 2009, vol. 30 (1), pp. 127-135.
Childs B.P., et al., "Defining and Reporting Hypoglycemia in Diabetes: A Report from the American Diabetes Association Workgroup on Hypoglycemia," Diabetes Care, 2005, vol. 28 (5), pp. 1245-1249.
Cholangiocarcinoma, Johns Hopkins Medicine Webstite, https://gi.jhsps.org/GDLDisease.aspx?CurrentUDV=31&GDLCat_ID=AF793A59-B736-42CB-9E1FE79D2B9FC358&GDL_Disease_ID=A6D1OE80-887D-49A7-B3BB-0517D38CE757, accessed on May 14, 2014, pp. 1-12.
Christensen M., et al., "Lixisenatide, A Novel GLP-1 Receptor Agonist for the Treatment of Type 2 Diabetes Mellitus," IDrugs: The Investigational Drugs Journal, 2009, vol. 12 (8), pp. 503-513.
Christensen M., et al., "Lixisenatide for Type 2 Diabetes Mellitus," Expert Opinion on Investigational Drugs, 2011, vol. 20 (4), pp. 549-557.
Cochran E., et al., "The Use of U-500 in Patients with Extreme Insulin Resistance," Diabetes Care, 2005, vol. 28 (5), pp. 1240-1244.
Colclough et al., Abstract "Levels of FPG and HbA1c Control and the Relationship to BMI in T2D Patients Treated with Basal Insulin and OAD Therapy." Abstract 2416-PO; Presented at the 72nd Scientific Session at the American Diabetes Association Meeting, 2012, A609, one page.
Colino E., et al., "Therapy with Insulin Glargine (Lantus) in toddlers, Children and Adolescents with Type 1 Diabetes," Diabetes Research and Clinical Practice, 2005, vol. 70 (1), pp. 1-7.
Community register of medicinal products for human use, Chemical Subgroup A10BX, "Lyxumia" European Commision—Public Health, p. 1-2 (May 2, 2013).
Craig et al., "ISPAD Clinical Practice Consensus Guidelines 2014 Compendium—Definition, epidemiology, and classification of diabetes in children and adolescents." Pediatric Diabetes, 15(Suppl. 20):4-17 (2014).
Crapo P.A., et al., "Postprandial Plasma-Glucose and -Insulin Responses to Different Complex Carbohydrates," Diabetes, 1977, vol. 26 (12), pp. 1178-1183.
Croom K.F., et al., "Liraglutide a Review of its Use in Type 2 Diabetes Mellitus," Drugs, 2009, vol. 69 (14), pp. 1985-2004.
Cryer P.E., "Hypoglycemia Is the Limiting Factor in the Management of Diabetes," Diabetes/Metabolism Research and Reviews, 1999, vol. 15 (1), pp. 42-46.
Cvetkovic R.S., et al., "Exenatide a Review of its Use in Patients with Type 2 Diabetes Mellitus (As an Adjunct to Metformin and/or a Sulfonylurea)," Drugs, 2007, vol. 67 (6), pp. 935-954.
Czech C., et al., "Proteolytic Processing of Mutated Human Amyloid Precursor Protein in Transgenic Mice," Brain Research Molecular Brain Research, 1997, vol. 47 (1-2), pp. 108-116.
D'Alessio D., "GLP-1 Receptor Agonists: Strategies for PPG Control," Medical Nursing Education, 2011, vol. 3, pp. 1-26.
D'Alessio D.A., et al., "Glucagon-Like Peptide 1 Enhances Glucose tolerance both by Stimulation of Insulin Release and by increasing Insulin-Independent Glucose Disposal," Journal of Clinical Investigation, 1994, vol. 93 (5), pp. 2263-2266.
Database, ADISCTI, "A randomized, 4-sequence, cross-over, double bind, dose response study of 0.4, 0.6 and 0.09 U/kg insluin glarine U300 compared to 0.4 U/kg Lantus U100 in patients with diabetes mellitus type I using euglycemic clamp technique" last updated Dec. 16, 2010, pp. 1-4.
Davis How to Convert mg to mmol/L, available online at http://www.ehow.com/how_8498850_convert mg-mmoll.html (accessed on Nov. 11, 2015).
De Arriba S.G., et al., "Carbonyl Stress and Nmda Receptor Activation Contribute to Methylglyoxal Neurotoxicity," Free Radical Biology and Medicine, 2006, vol. 40 (5), pp. 779-790.
De La Pena A., et al., "Pharmacokinetics and Pharmacodynamics of High-Dose Human Regular U-500 Insulin Versus Human Regular U-100 Insulin in Healthy Obese Subjects," Diabetes Care, 2011, vol. 34 (12), pp. 2496-2501.
De Rosa R., et al., "Intranasal Administration of Nerve Growth Factor (Ngf) Rescues Recognition Memory Deficits in Ad11 Anti-Ngf Transgenic Mice," Proceedings of the National Academy of Sciences of the United States of America, 2005, vol. 102 (10), pp. 3811-3816.
Deacon C.F., et al., "Dipeptidyl Peptidase IV inhibition Potentiates the Insulinotropic Effect of Glucagon-Like Peptide 1 in the Anesthetized Pig," Diabetes, 1998, vol. 47 (5), pp. 764-769.
Deacon C.F., et al., "Dipeptidyl Peptidase IV Resistant Analogues of Glucagon-Like Peptide-1 Which have Extended Metabolic Stability and Improved Biological Activity," Diabetologia, 1998, vol. 41 (3), pp. 271-278.
Definition of indication, Merriam-Webster online, accessed Oct. 22, 2015, 2 pages.
Definition of palliative, http://medicaldictionary.thefreedictionary.com/, accessed on Nov. 6, 2014, pp. 1-2.
Definition of sphincter of pancreatic duct in the Medical Dictionary, http://medicaldictionary.thefreedictionary.com/, accessed on May 22, 2014, pp. 1-2.
Defronzo R.A., et al., "Effects of Exenatide (Exendin-4) on Glycemic Control and Weight Over 30 Weeks in Metformin-Treated Patients with Type 2 Diabetes," Diabetes care, 2005, vol. 28 (5), pp. 1092-1100.
Defronzo R.A., "Pathogenesis of Type 2 Diabetes: Implications for Metformin," Drugs, 1999, vol. 58 (Suppl 1), pp. 29-30.
Defronzo R.A., "Pharmacologic therapy for Type 2 Diabetes Mellitus," Annals of Internal Medicine, 1999, vol. 131 (4), pp. 281-303.
Delatour B., et al., "Alzheimer Pathology Disorganizes Cortico-Cortical Circuitry: Direct Evidence from a Transgenic Animal Model," Neurobiology of Disease, 2004, vol. 18 (1), pp. 41-47.
Devries J.H., et al., "Sequential intensification of Metformin Treatment in Type 2 Diabetes with Liraglutide Followed by Randomized Addition of Basal Insulin Prompted by A1C Targets," Diabetes Care, 2012, vol. 35 (7), pp. 1446-1454.
Dewitt D.E., "Case Study: Treating New on-Set Catabolic Type 2 Diabetes with Glamine and Lispro," Clinical Diabetes, 2006, vol. 24 (4), pp. 180-181.
Diabetes Prevention Program Research Group, "Reduction in the incidence of Type 2 Diabetes with Lifestyle intervention or Metformin," The New England Journal of Medicine, 2002, vol. 346 (6), pp. 393-403.
Distiller et al., Poster: "Pharmacokinetics and Pharmacodynamics of a New GLP-1 Agonist AVE0010 in Type 2 Diabetes Patients" Meeting: 68th Scientific Sessions (Jun. 2008) Poster No. 520-P.
Dixon G.H., et al., "Regeneration of Insulin Activity from the Separated and inactive A and B Chains," Nature, 1960, vol. 188 (4752), pp. 721-724.
Donelli G., et al., "Plastic Biliary Stent Occlusion: Factors Involved and Possible Preventive Approaches," Clinical Medicine & Research, 2007, vol. 5 (1), pp. 53-60.
Dormandy J.A., et al., "Secondary Prevention of Macrovascular Events in Patients with Type 2 Diabetes in the Proactive Study (Prospective Pioglitazone Clinical Trial in Macrovascular Events): A Randomised Controlled Trial," Lancet, 2005, vol. 366 (9493), pp. 1279-1289.
Doyle M.E. et al., "Mechanisms of Action of Glucagon-Like Peptide 1 in the Pancreas," Pharmacology & Therapeutics, 2007, vol. 113 (3), pp. 546-593.

(56) References Cited

OTHER PUBLICATIONS

Drucker D.J. et al., "The incretin System: Glucagon-Like Peptide-1 Receptor Agonists and Dipeptidyl Peptidase-4 inhibitors in Type 2 Diabetes," Lancet, 2006, vol. 368 (9548), pp. 1696-1705.
Drucker D.J., "Glucagon-Like Peptides," Diabetes, 1998, vol. 47 (2), pp. 159-169.
Drucker D.J., "Mini Review: The Glucagon-Like Peptides," Endocrinology, 2001, vol. 142 (2), pp. 521-527.
Drucker D.J., "The Biology of Incretin Hormones," Cell Metabolism, 2006, vol. 3 (3), pp. 153-165.
DrugBank, "Insulin glargine," available online at http://www.drugbank.ca/drugs/DB00047, 16 pages (accessed online Sep. 25, 2014).
Drury P.L., et al., "Diabetic Nephropathy," British Medical Bulletin, 1989, vol. 45 (1), pp. 127-147.
Dubois B., et al., "Revising the Definition of Alzheimer's Disease: A New Lexicon," Lancet Neurology, 2010, vol. 9 (11), pp. 1118-1127.
Dunn C.J., et al., "Insulin Glargine: An Updated Review of its Use in the Management of Diabetes Mellitus," Drugs, 2003, vol. 63 (16), pp. 1743-1778.
During M.J., et al., "Glucagon-Like Peptide-1 Receptor is involved in Learning and Neuroprotection," Nature Medicine, 2003, vol. 9 (9), pp. 1173-1179.
Eckert A., et al., "Alzheimer's Disease-Like Alterations in Peripheral Cells from Presenilin-1 Transgenic Mice," Neurobiology of Disease, 2001, vol. 8 (2), pp. 331-342.
EFC10780 (Sanofi study), "A randomized, double-blind, double-dummy, 2-arm parallel-group, multicenter 24-week study comparing the efficacy and safety of AVE0010 to sitagliptin as add-on to metformin in obese type 2 diabetic patients younger than 50 and not adequately controlled with metformin (EFC10780)" p. 1-4 (Jan. 29, 2014).
EFC10781 Clinical Trials, "24-week Treatment With Lixisenatide in Type 2 Diabetes Insufficiently Controlled With Metformin and Insulin Glargine" ClinicalTrials.gov; EFC10781 pp. 1-5 (Sep. 2009).
EFC6017; Clinical Trial Eudra CT No. 2007-005884-92, accessed Apr. 24, 2015, one page.
EFC6018; Clinical trial EudraCT 2007-005887-29, "Getgoal-Mono" accessed Jul. 27, 2014; pp. 1-16.
EMA—Science Medicines Health "Toujeo" EPAR Summary for the Public, first published Nov. 5, 2009, pp. 1-3.
EMA Press Release, "European Medicines Agency recommends suspension of Avandia, Avandamet and Avaglim" pp. 1-2 (Sep. 23, 2010).
English translation of Search Report for Chinese Patent Application No. 201280053404.6; dated Feb. 10, 2015, pp. 1-3.
English translation of Search Report for Chinese Patent Application No. 20140220537.9; dated Feb. 13, 2015, pp. 1-2.
European Medicines Agency—Science Medicines Health, "Guideline on clinical investigation of medicinal products in the treatment of diabetes mellitus" Committee for Medicinal Products for Human Use, Jan. 20, 2010, pp. 1-19.
Ex Parte Herrmann, Appeal No. 2009-001777 U.S. Appl. No. 10/616,457 (B. Pai. Nov. 13, 2009).
Executive Summary, "Standards of Medical Care in Diabetes-2009" Diabetes Care,32(Suppl. 1):S6-S12 (Jan. 2009).
Extended European Search Report for Euorpean Application No. 98 11 0889.7; dated Oct. 14, 1998, pp. 1-4.
Extended European Search Report for European Application No. 09 17 5878.3; dated Mar. 24, 2010, pp. 1-4.
Extended European Search Report for European Application No. 09 17 5877.1; dated Apr. 29, 2010, pp. 1-5.
Extended European Search Report for European Application No. 10 16 4368.2; dated Oct. 14, 2010, pp. 1-6.
Extended European Search Report for European Application No. 10 30 5780; dated Nov. 16, 2010, pp. 1-3.
Extended European Search Report for European Application No. 11 15 3106; dated Jul. 6, 2011, pp. 1-12.
Extended European Search Report for European Application No. 11 16 0270.2; dated Sep. 19, 2011, pp. 1-8.
Extended European Search Report for European Application No. 11 16 6415; dated Mar. 12, 2012, pp. 1-12.
Extended European Search Report for European Application No. 11 17 9149.7; dated Feb. 9, 2012, pp. 1-8.
Extended European Search Report for European Application No. 13 305 126; dated Apr. 11, 2013, pp. 1-7.
Extended European Search Report for European Application No. 13 305 432.0; dated Sep. 13, 2013, pp. 1-5.
Extended European Search Report for European Application No. 14 16 6877.2; dated Aug. 18, 2014, pp. 1-6.
Extended European Search Report for European Application No. 14 19 7154.9: dated Apr. 8, 2015, pp. 1-7.
Fabunmi R., et al., "Patient Characteristics, Drug Adherence Patterns, and Hypoglycemia Costs for Patients with Type 2 Diabetes Mellitus Newly initiated on Exenatide or Insulin Glargine," Current Medical Research and Opinion, 2009, vol. 25 (3), pp. 777-786.
Faivre E., et al., "Effects of Gip Analogues in Neuronal Signalling, Cell Proliferation and Learning and Memory," Regulatory Peptides, 2010, vol. 164 (1), pp. 40-41.
FDA Guidance for Industry, US Department of Health and Human Services, Food and Drug Administration, Center for Drug Evaluation and Research (COER), pp. 1-11, Feb. 2014.
FDA label of ApidraC, May 2014, pp. 1-35.
FDA label of Humalog®, Mar. 2013, pp. 1-27.
FDA label of Lantus®, Oct. 2013, pp. 1-44.
Feinglos M.N., et al., "Effects of Liragiutide (Nn2211), A Long-Acting GLP-1 Analogue, on Glycaemic Control and Bodyweight in Subjects with Type 2 Diabetes," Diabetic Medicine, 2005, vol. 22 (8), pp. 1016-1023.
Fieller E.C., "Symposium on Interval Estimation; Some Problems with Interval Estimation," Journal of the Royal Statistical Society, 1954, vol. 16 (2), pp. 175-185.
Final Office Action from U.S. Appl. No. 12/617,805; dated Feb. 11, 2013, pp. 1-13.
Final Office Action from U.S. Appl. No. 12/617,805; dated Jan. 12, 2012, pp. 1-14.
Final Office Action from U.S. Appl. No. 12/617,805; dated Jan. 13, 2015, pp. 1-11.
Final Office Action issued in U.S. Appl. No. 13/602,913; dated Apr. 2, 2015, pp. 1-7.
Final Office Action issued in U.S. Appl. No. 13/602,913; dated Jun. 20, 2014, pp. 1-27.
Final Office Action issued in U.S. Appl. No. 13/602,913; dated Sep. 13, 2013, pp. 1-11.
Final Rejection in U.S. Appl. No. 13/633,496; dated Nov. 18, 2014, pp. 1-11.
Final Rejection in U.S. Appl. No. 13/633,496; dated Nov. 4, 2013, pp. 1-7.
Final Rejection in U.S. Appl. No. 13/633,563; dated Apr. 22, 2015, pp. 1-12.
Final Rejection in U.S. Appl. No. 13/633,563; dated Dec. 16, 2013, pp. 1-58.
Final Rejection issued in U.S. Appl. 14/172,151; dated Jul. 20, 2015, pp. 1-18.
Final Rejection issued in U.S. Appl. No. 12/617,811; dated Jan. 4, 2013, pp. 1-6.
Final Rejection issued in U.S. Appl. No. 12/617,811; dated Jul. 31, 2015, pp. 1-15.
Final Rejection issued in U.S. Appl. No. 13/110,568; dated Feb. 21, 2013, pp. 1-20.
Final Rejection issued in U.S. Appl. No. 13/310,118; dated Aug. 2, 2012, pp. 1-20.
Final Rejection issued in U.S. Appl. No. 13/363,956; dated May 20, 2014, pp. 1-16.
Final Rejection issued in U.S. Appl. No. 13/382,442; dated Jul. 17, 2013, pp. 1-30.
Final Rejection issued in U.S. Appl. No. 13/382,442; dated Jun. 13, 2014, pp. 1-29.
Final Rejection issued in U.S. Appl. No. 13/382,772; dated Jun. 3, 2014, pp. 1-34.

(56) References Cited

OTHER PUBLICATIONS

Final Rejection issued in U.S. Appl. No. 13/382,772; dated Feb. 10, 2015, pp. 1-36.
Final Rejection issued in U.S. Appl. No. 13/467,707; dated Feb. 25, 2014, pp. 1-18.
Final Rejection issued in U.S. Appl. No. 13/467,707; dated Jan. 7, 2015, pp. 1-8.
Final Rejection issued in U.S. Appl. No. 13/468,422; dated Jan. 6, 2014, pp. 1-21.
Final Rejection issued in U.S. Appl. No. 13/468,422; dated Jan. 23, 2015, pp. 1-27.
Final Rejection issued in U.S. Appl. No. 13/469,633; dated Dec. 4, 2013, pp. 1-17.
Final Rejection issued in U.S. Appl. No. 13/469,633; dated Jan. 23, 2015, pp. 1-12.
Final Rejection issued in U.S. Appl. No. 13/509,507; dated Jul. 23, 2015, pp. 1-11.
Final Rejection issued in U.S. Appl. No. 13/509,542; dated Nov. 21, 2013, pp. 1-34.
Final Rejection issued in U.S. Appl. No. 13/509,542; dated Jan. 28, 2015, pp. 1-26.
Final Rejection issued in U.S. Appl. No. 13/595,590; dated Apr. 2, 2014, pp. 1-7.
Final Rejection issued in U.S. Appl. No. 13/595,590; dated Dec. 19, 2014, pp. 1-14.
Final Rejection issued in U.S. Appl. No. 13/661,476, dated Oct. 2, 2014, pp. 1-33.
Final Rejection issued in U.S. Appl. No. 13/692,640; dated Jan. 6, 2015, pp. 1-11.
Final Rejection issued in U.S. Appl. No. 13/692,640; dated Jun. 2, 2015, pp. 1-12.
Final Rejection issued in U.S. Appl. No. 13/700,631; dated Apr. 13, 2015, pp. 1-19.
Final Rejection issued in U.S. Appl. No. 13/700,631; dated Jun. 18, 2014, pp. 1-25.
Final Rejection issued in U.S. Appl. No. 13/819,114; dated Mar. 2, 2015, pp. 1-10.
Final-Rejection issued in U.S. Appl. No. 13/432,811; dated Dec. 12, 2014, pp. 1-8.
Final-Rejection issued in U.S. Appl. No. 13/432,811; dated Mar. 31, 2015, pp. 1-9.
Final-Rejection issued in U.S. Appl. No. 13/432,811; dated Sep. 6, 2014, pp. 1-8.
Fonseca V.A., et al., "Efficacy and Safety of the once-Daily GLP-1 Receptor Agonist Lixisenatide in Monotherapy: A Randomized, Double-Blind, Placebo-Controlled Trial in Patients with Type 2 Diabetes (Getgoal-Mono)," Diabetes Care, 2012, vol. 35 (6), pp. 1225-1231.
Fox J.D., et al., "Single Amino Acid Substitutions on the Surface of *Escherichia coli* Maltose-Binding Protein can have a Profound Impact on the Solubility of Fusion Proteins," Protein Science, 2001, vol. 10 (3), pp. 622-630.
Fransson J., et al., "Oxidation of Human Insulin-Like Growth Factor I in formulation Studies: Kinetics of Methionine Oxidation in Aqueous Solution and in Solid State," Pharmaceutical Research, 1996, vol. 13 (8), pp. 1252-1257.
Galloway J.A., et al., "New forms of Insulin," Diabetes, 1972, vol. 21 (2 Suppl), pp. 637-648.
Gallwitz B., "Liraglutide. GLP-1 Receptor Agonist Treatment of Type 2 Diabetes Treatment of Obesity," Drugs of the Future, 2008, vol. 33 (1), pp. 13-20.
Gandhi S., et al., "Molecular Pathogenesis of Parkinson's Disease," Human Molecular Genetics, 2005, vol. 14 (18), pp. 2749-2755.
Garber A., et al., "Liraglutide Versus Glimepiride Monotherapy for Type 2 Diabetes (Lead-3 Mono): A Randomised, 52-Week, Phase III, Double-Blind, Parallel-Treatment Trial," The Lancet, 2009, vol. 373 (9662), pp. 473-481.
Garg R., et al., "U-500 Insulin: Why, When and How to Use in Clinical Practice," Diabetes/Metabolism Research and Reviews, 2007, vol. 23 (4), pp. 265-268.
Garriques L.N., et al., "The Effect of Mutations on the Structure of Insulin Fibrils Studied by Fourier Transform infrared (FTIR) Spectroscopy and Electron Microscopy," Journal of Pharmaceutical Sciences, 2002, vol. 91 (12), pp. 2473-2480.
Gault V.A., et al., "GLP-1 Agonists Facilitate Hippocampal LTP and Reverse the Impairment of LTP induced by Beta-Amyloid," European Journal of Pharmacology, 2008, vol. 587 (1-3), pp. 112-117.
Gavin J.R., "Report of the Expert Committee on the Diagnosis and Classification of Diabetes Mellitus," Diabetes Care, 1997, vol. 20 (7), pp. 1183-1197.
Geiger R., "The Chemistry of Insulin," Chemiker Zeitung, 1976, vol. 100 (3), pp. 54-56.
Gengler S., et al., "Val(8)GLP-1 Rescues Synaptic Plasticity and Reduces Dense Core Plaques in APP/PS1 Mice," Neurobiology of Aging, 2012, vol. 33 (2), pp. 265-278.
Gerich et al., "Monotherapy with GLP-1 receptor agonist, Lixisenatide, significantly improves glycaemic control in type 2 diabetic patients," Diabetologia 53(Supplement 1)p. S330, Abstract 830, Presented at 46th Annual Meeting of EASD, Stockholm, Sweden, p. 1 (Sep. 2010).
Giugliano D., et al., "Treatment Regimens with Insulin Analogues and Haemoglobin A1C Target of <7% in Type 2 Diabetes: A Systematic Review," Diabetes Research and Clinical Practice, 2010, vol. 92 (1), pp. 1-10.
Goke R., et al., "Distribution of GLP-1 Binding Sites in the Rat Brain: Evidence That Exendin-4 is a Ligand of Brain GLP-1 Binding Sites," European Journal of Neuroscience, 1995, vol. 7 (11), pp. 2294-2300.
Goldstein D.E., et al., "Tests of Glycemia in Diabetes," Diabetes Care, 1995, vol. 18 (6), pp. 896-909.
Gough K., et al., "Assessment of Dose Proportionality: Report from the Statisticians in the Pharmaceutical Industry/ Pharmacokinetics UK Joint Working Party," Drug Information Journal, 1995, vol. 29, pp. 1039-1048.
Goykhman S., et al., "Insulin Glargine: A Review 8 Years After its introduction," Expert Opinion on Pharmacotherapy, 2009, vol. 10 (4), pp. 705-718.
Greig N.H., et al., "Once Daily Injection of Exendin-4 to Diabetic Mice Achieves Long-Term Beneficial Effects on Blood Glucose Concentrations," Diabetologia, 1999, vol. 42 (1), pp. 45-50.
Guidance for Industry, US Department of Health and Human Services, Food and Drug Administration, Center for Drug Evaluation and Research (COER), pp. 1-11, Feb. 2014.
"Guideline for Management of Postmeal Glucose," International Diabetes Federation, pp. 1-27, Lesaffre Printers, ISBN 2-930229-48-9 (2007).
Gura T., "Systems for Identifying New Drugs Are often Faulty," Science, 1997, vol. 278 (5340), pp. 1041-1042.
Gutniak M., et al., "Antidiabetogenic Effect of Glucagon-Like Peptide-1 (7-36) Amide in Normal Subjects and Patients with Diabetes Mellitus," The New England Journal of Medicine, 1992, vol. 326 (20), pp. 1316-1322.
Gygi S.P., et al, "Quantitative Analysis of Complex Protein Mixtures Using Isotope-Coded Affinity Tags," Nature Biotechnology, 1999, vol. 17 (10), pp. 994-999.
Hamilton A., et al., "Novel GLP-1 Mimetics Developed to Treat Type 2 Diabetes Promote Progenitor Cell Proliferation in the Brain," Journal of Neuroscience Research, 2011, vol. 89 (4), pp. 481-489.
Hamilton A., et al., "Receptors for the incretin Glucagon-Like Peptide-1 are Expressed on Neurons in the Central Nervous System," NeuroReport, 2009, vol. 20 (13), pp. 1161-1166.
Hanas R., et al., "2010 Consensus Statement on the Worldwide Standardization of the Hemoglobin A1C Measurement," Diabetes Care, 2010, vol. 33 (8), pp. 1903-1904.
Hanefeld M., et al., "The Postprandial State and the Risk of Atherosclerosis," Diabetic Medicine, 1997, vol. 14 (Suppl 3), pp. S6-S11.
Hanefeld M., "Normnahe Postprandiale Hyperglykamie-Eine Essenzielle Komponente Guter Diabeteskontrolle Und Prevention Kardiovaskularer Erkrankungen (Near-Normal Postprandial Hyperglycemia—An Essential Component of Good Diabetes Control and Prevention of Car-

(56) References Cited

OTHER PUBLICATIONS diovascular Diseases)," Paul Langerhans Lecture Diabetologie and Stoffwechsel, 2007, vol. 2, pp. 362-369.
Hanna et al., "Canadian Diabetes Association Clinical Practice Guidelines Expert Committee Pharmacologic Management of Type 2 Diabetes," Canadian Journal of Diabetes, 2003, vol. 27 (Supp 2), pp. S37-S42.
Harkavyi A., et al., "Glucagon-Like Peptide I Receptor Stimulation Reverses Key Deficits in Distinct Rodent Models of Parkinson's Disease," Journal of Neuroinflammation, 2008, vol. 5 (19), pp. 1-9.
Harris S.B., et al., "Clinical inertia in Patients with T2Dm Requiring Insulin in Family Practice," Canadian Family Physician, 2010, vol. 56 (12), pp. e418-e424.
Hartmann H., et al., "Biological Activity of Des-(B26-B30)-Insulinamide and Related Analogues in Rat Hepatocyte Cultures," Diabetologia, 1989, vol. 32 (7), pp. 416-420.
Hellstrom M., et al., "T1388 GTP-010 as a Therapetuic tool in IBS Pain Relief: Prospective, Randomized, Palebo-Controlled Study of a GLP-1 Analog," Gastroenterology, 2008, vol. 134 (4), pp. A-544.
Higgins G.C., et al., "Oxidative Stress: Emerging Mitochondrial and Cellular themes and Variations in Neuronal Injury," Journal of Alzheimer's Disease, 2010, vol. 20, pp. S453-S473.
Himeno T., et al., "Beneficial Effects of Exendin-4 on Experimental Polyneuropathy in Diabetic Mice," Diabetes, 2011, vol. 60 (9), pp. 2397-2406.
Hinds K., et al., "Synthesis and Characterization of Poly(Ethylene Glycol)-Insulin Conjugates," Bioconjugate Chemistry, 2000, vol. 11 (2), pp. 195-201.
Hoe 901/2004 Study Investigators Group, "Safety and Efficacy of Insulin Glargine (Hoe 901) Versus NPH Insulin in Combination with oral Treatment in Type 2 Diabetic Patients," Diabetic Medicine, 2003, vol. 20, pp. 545-551.
Holman R.R., et al., "10-Year Follow-Up of intensive Glucose Control in Type 2 Diabetes," The New England Journal of Medicine, 2008, vol. 359 (15), pp. 1577-1589.
Holscher C., "Development of Beta-Amyloid-induced Neurodegeneration in Alzheimer's Disease and Novel Neuroprotective Strategies," Reviews in the Neurosciences, 2005, vol. 16 (3), pp. 181-212.
Holscher C., et al., "New Roles for Insulin-Like Hormones in Neuronal Signalling and Protection: New Hopes for Novel Treatments of Alzheimer's Disease?," Neurobiology of Aging, 2008, vol. 31 (9), pp. 1495-1502.
Holscher C., "Incretin Analogues that have been Developed to Treat Type 2 Diabetes Hold Promise as a Novel Treatment Strategy for Alzheimer's Disease," Recent Patents on Cns Drug Discovery, 2010, vol. 5 (2), pp. 109-117.
Holscher C., "Possible Causes of Alzheimer's Disease: Amyloid Fragments, Free Radical, and Calcium Homeostasis," Neurobiology of Disease, 1998, vol. 5 (3), pp. 129-141.
Holscher C., "The Role of GLP-1 in Neuronal Activity and Neurodegeneration," Vitamins and Hormones, 2010, vol. 84, pp. 331-354.
Holst J.J., et al., "Combining GLP-1 Receptor Agonists with Insulin: therapeutic Rationales and Clinical Findings," Diabetes, Obesity and Metabolism, 2013, vol. 15 (1), pp. 3-14.
Home P.D., et al., "Insulin Treatment: A Decade of Change," British Medical Bulletin, 1989, vol. 45 (1), pp. 92-110.
http://diabetes.emedtv.com/lantus/generic-lantus.html; one page, last accessed Dec. 23, 2015.
Humalog® prescribing information, Apr. 2012, pp. 1-6.
Hunter K., et al., "Drugs Developed to Treat Diabetes, Liraglutide and Lixisenatide, Cross the Blood Brain Barrier and Enhance Neurogenesis," BMC Neuroscience, 2012, vol. 13, pp. 1-6.
Inpharma, Product News. "AVE0010 set to deliver in type 2 diabetes mellitus," Database Adisnews, retrieved from STN, Jun. 2008, pp. 1-3.
"Insulin Aspart Injection." Formulated Preparations: Specific Monographs. British Pharmacopoeia 3. pp. 1-3 (2012).
International Search Report by the ISA for International Application No. PCT/EP2007/005932; dated Oct. 9, 2007, pp. 1-6.
International Search Report by the ISA for International Application No. PCT/EP2009/000017; dated Jun. 22, 2009, pp. 1-7.
International Search Report by the ISA for International Application No. PCT/EP2010/059436; dated Jun. 17, 2011, pp. 1-5.
International Search Report by the ISA for International Application No. PCT/EP2010/059438; dated Oct. 4, 2010, pp. 1-3.
International Search Report by the ISA for International Application No. PCT/EP2010/062638; dated Mar. 18, 2011, pp. 1-5.
International Search Report by the ISA for International Application No. PCT/EP2010/067250; dated Mar. 23, 2011, pp. 1-3.
International Search Report by the ISA for International Application No. PCT/EP2011/058079; dated Mar. 22, 2012, pp. 1-6.
International Search Report by the ISA for International Application No. PCT/EP2011/058784; dated Jun. 30, 2011, pp. 1-9.
International Search Report by the ISA for International Application No. PCT/EP2012/051670; dated Mar. 26, 2012, pp. 1-18.
International Search Report by the ISA for International Application No. PCT/EP2012/055660; dated May 10, 2012, pp. 1-6.
International Search Report by the ISA for International Application No. PCT/EP2012/058745; dated Jul. 12, 2012, pp. 1-6.
International Search Report by the ISA for International Application No. PCT/EP2012/058747; dated Jul. 8, 2012, pp. 1-6.
International Search Report by the ISA for International Application No. PCT/EP2012/058749; dated Jul. 31, 2012, pp. 1-6.
International Search Report by the ISA for International Application No. PCT/EP2012/058779; dated Aug. 28, 2012, pp. 1-5.
International Search Report by the ISA for International Application No. PCT/EP2012/066617; dated Nov. 22, 2012, pp. 1-5.
International Search Report by the ISA for International Application No. PCT/EP2012/067144; dated Aug. 11, 2012, pp. 1-5.
International Search Report by the ISA for International Application No. PCT/EP2012/069483; dated Nov. 29, 2011, pp. 1-4.
International Search Report by the ISA for International Application No. PCT/EP2012/069485; dated Dec. 11, 2012, pp. 1-5.
International Search Report by the ISA for International Application No. PCT/EP2012/071271; dated Jan. 30, 2013, pp. 1-5.
International Search Report by the ISA for International Application No. PCT/EP2012/074150; dated Nov. 20, 2012, pp. 1-4.
International Search Report by the ISA for International Application No. PCT/EP2014/051976; dated Mar. 4, 2014, pp. 1-3.
International Search Report by the ISA for International Application No. PCT/EP2014/056498; dated Jun. 25, 2014, pp. 1-10.
International Search Report by the ISA for International Application No. PCT/EP2014/062418; dated Sep. 22, 2014, pp. 1-4 .
Inzucchi S.E., et al., "Management of Hyperglycemia in Type 2 Diabetes: A Patient-Centered Approach," Diabetes Care, 2012, vol. 35, pp. 1364-1379.
Isacson R., et al., "The Glucagon-Like Peptide 1 Receptor Agonist Exendin-4 improves Reference Memory Performance and Decreases Immobility in the forced Swim Test," European Journal of Pharmacology, 2009, vol. 650 (1), pp. 249-255.
ISPAD, International Diabetes Federation; "Global/IDF/ISPAD Guideline for Diabetes in Childhood and Adolescence," pp. 1-132 (2011).
Jackson R.L., et al., "Neutral Regular Insulin," Diabetes, 1972, vol. 21 (4), pp. 235-245.
Jain R.K., "Barriers to Drug Delivery in Solid Tumors," Scientific American, 1994, vol. 271 (1), pp. 58-65.
Jang J.H., et al., "Neuroprotective Effects of Triticum Aestivum L. Against B-Amyloid-induced Cell Death and Memory Impairments," Phytotherapy Research, 2010, vol. 24 (1), pp. 76-84.
Jekel P.A., et al., "Use of Endoproteinase Lys-C from Lysobacter Enzymogenes in Protein Sequence Analysis," Analytical Biochemistry, 1983, vol. 134 (2), pp. 347-354.
Jendle J., et al., "Insulin and GLP-1 Analog Combinations in Type 2 Diabetes Mellitus: A Critical Review," Expert Opinion on Investigational Drugs, 2012, vol. 21 (10), pp. 1463-1474.
Jimenez S., et al., "Inflammatory Response in the Hippocampus of PS1M146L/App751SL Mouse Model of Alzheimer's Disease: Age-Dependent Switch in the Microglial Phenotype from Alternative to Classic," The Journal of Neuroscience, 2008, vol. 28 (45), pp. 11650-11661.

(56) References Cited

OTHER PUBLICATIONS

Johnson et al., "When is a unit of insulin not a unit of insulin? Detemir dosing in type 2 diabetes" Poster, one page, 2008. http://professional.diabetes.org/ContenUPosters/2008/p8-LB.pdf.

Jorgensen K.H., et al., "Five Fold Increase of Insulin Concentration Delays the Absorption of Subcutaneously Injected Human Insulin Suspensions in Pigs," Diabetes Research and Clinical Practice, 2000, vol. 50, pp. 161-167.

Kaarsholm N.C., et al., "Engineering Stability of the Insulin Monomer Fold with Application to Structure-Activity Relationships," Biochemistry, 1993, vol. 32 (40), pp. 10773-10778.

Kadima W., "Role of Metal Ions in the T- to R-Allosteric Transition in the Insulin Hexamer," Biochemistry, 1999, vol. 38 (41), pp. 13443-13452.

Kaduszkiewicz H., et al., "Cholinesterase inhibitors for Patients with Alzheimer's Disease: Systematic Review of Randomised Clinical Trials," British Medical Journal (Clinical Research ed.), 2005, vol. 331 (7512), pp. 321-327.

Kaech S., et al., "Culturing Hippocampal Neurons," Nature Protocols, 2006, vol. 1 (5), pp. 2406-2415.

Kahn S.E., et al., "Glycemic Durability of Rosiglitazone, Metformin, or Glyburide Monotherapy," The New England Journal of Medicine, 2006, vol. 355 (23), pp. 2427-2443.

Kakhki V.R.D., et al., "Normal Values of Gallbladder Ejection Fraction Using 99m Tc-Sestamibi Scintigraphy after a Fatty Meal formula," Journal of Gastrointestinal and Liver Diseases, 2007, vol. 16 (2), pp. 157-161.

Kamisawa T., et al., "Pancreatographic investigation of Pancreatic Duct System and Pancreaticobiliary Malformation," Journal of Anatomy, 2008, vol. 212 (2), pp. 125-134.

Kanazawa M., et al., "Criteria and Classification of Obesity in Japan and Asia-Oceania," Asia Pacific Journal of Clinical Nutrition, 2002, vol. 11 (Suppl 7), pp. S732-S737.

Kang S., et al., "Subcutaneous Insulin Absorption Explained by Insulin'S Physicochemical Properties Evidence from Absorption Studies of Soluble Human Insulin and Insulin Analogues in Humans," Diabetes Care, 1991, vol. 14 (11), pp. 942-948.

Kao C.H., et al., "The Evaluation of Gallbladder Function by Quantitative Radionuclide Cholescintigraphy in Patients with Noninsulin-Dependent Diabetes Mellitus," Nuclear Medicine Communications, 1993, vol. 14 (10), pp. 868-872.

Kapitza et al., Abstract "Pharmacodynamic Characteristics of Lixisenatide QD vs Liraglutide QD in Patients with T2DM Inadequately Controlled with Metformin" Abtract D-0740, presented at the World Diabetes Congress in Dubai, Dec. 5-8, 2011, one page.

Kastin A.J., et al., "Entry of Exedin-4 into Brain Is Rapid but may be Limited at High Doses International Journal of Obesity and Related Metabolic Disorders," Journal of the International Association for the Study of Obesity, 2003, vol. 27 (3), pp. 313-318.

Kastin A.J., et al., "Interactions of Glucagon-Like Peptide-1 (GLP-1) with the Blood-Brain Barrier," Journal of Molecular Neuroscience, 2001, vol. 18 (1-2), pp. 7-14.

Kemmler W., et al., "Studies on the Conversion of ProInsulin to Insulin," The Journal of Biological Chemistry, 1971, vol. 246 (22), pp. 6786-6791.

Kendall D.M., et al., "Effects of Exenatide (Exendin-4) on Glycemic Control Over 30 Weeks in Patients with Type 2 Diabetes Treated with Metformin and a Sulfonylurea," Diabetes care, 2005, vol. 28 (5), pp. 1083-1091.

Kielgast U., et al., "Treatment of Type 1 Diabetic Patients with Glucagon-Like Peptide-1 (GLP-1) and GLP-1R Agonists," Current Diabetes Reviews, 2009, vol. 5 (4), pp. 266-275.

Kim S., et al., "Exendin-4 Protects Dopaminergic Neurons by Inhibition of Microglial Activation and Matrix Metalloproteinase-3 Expression in an Animal Model of Parkinson's Disease," Journal of Endocrinology, 2009, vol. 202 (3), pp. 431-439.

Knee T.S., et al., "A Novel Use of U-500 Insulin for Continuous Subcutaneous Insulin infusion in Patients with Insulin Resistance: A Case Series," Endocrine Practice, 2003, vol. 9 (3), pp. 181-186.

Knudsen L.B., et al., "Potent Derivatives of Glucagon-Like Peptide-1 with Pharmacokinetic Properties Suitable for once Daily Administration," Journal of Medicinal Chemistry, 2000, vol. 43 (9), pp. 1664-1669.

Kohn W.D., et al., "Pi-Shifted Insulin Analogs with Extended in Vivo Time Action and Favorable Receptor Selectivity," Peptides, 2007, vol. 28 (4), pp. 935-948.

Kohner E.M., "Diabetic Retinopathy," British Medical Bulletin, 1989, vol. 45 (1), pp. 148-173.

Kolterman O.G., et al., "Synthetic Exendin-4 (Exenatide) Significantly Reduces Postprandial and Fasting Plasma Glucose in Subjects with Type 2 Diabetes," The Journal of Clinical Endocrinology & Metabolism, 2003, vol. 88 (7), pp. 3082-3089.

Korczyn A.D., et al, "Emerging therapies in the Pharmacological Treatment of Parkinson's Disease," Drugs, 2002, vol. 62 (5), pp. 775-786.

Krishnamurthy G.T., et al., "Constancy and Variability of Gallbladder Ejection Fraction: Impact on Diagnosis and therapy," Journal of Nuclear Medicine, 2004, vol. 45 (11), pp. 1872-1877.

Lando, "The New 'Designer' Insulins", Clinical Diabetes, 18(4): Fall 2000 (http://journal.diabetes.org/clinical diabelesN18N42000/pg154.hlm; accessed Oct. 22, 2013, pp. 1-13).

Langston J.W., et al., "Chronic Parkinsonism in Humans due to a Product of Meperedine-Analog Synthesis," Science, 1983, vol. 219 (4587), pp. 979-980.

Langui D., et al., "Subcellular Topography of Neuronal A13 Peptide in APPxPS1 Transgenic Mice," The American Journal of Pathology, 2004, vol. 165 (5), pp. 1465-1477.

Lantus® Annex I—Summary of product characteristics. Date of first authorisation: Jun. 9, 2000, pp. 1-164.

Lantus® prescribing information, May 2012, pp. 1-6.

Lantus® Product Information—European Medicines Agency, first published Aug. 5, 2009, pp. 1-2.

Larsen B.D., et al., "Sequence-Assisted Peptide Synthesis (SAPS)," Journal of Peptide Research, 1998, vol. 52 (6), pp. 470-476.

Larsen P.J., et al, "Combination of the Insulin Sensitizer, Pioglitazone, and the Long-Acting GLP-1 Human Analog, Liraglutide, Exerts Potent Synergistic Glucose-Lowering Efficacy in Severely Diabetic ZDF Rats," Diabetes, Obesity and Metabolism, 2008, vol. 10, pp. 301-311.

Laursen K, et al., "Enhanced Monitoring of Biopharmaceutical Product Purity Using Liquid Chromatography-Mass Spectrometry," Journal of Chromatography A, 2011, vol. 1218 (28), pp. 4340-4348.

Lee C.H., et al., "Ischemia-lnduced Changes in Glucagon-Like Peptide-1 Receptor and Neuroprotective Effect of its Agonist, Exendin-4, in Experimental Transient Cerebral Ischemia," Journal of Neuroscience Research, 2011, vol. 89 (7), pp. 1103-1113.

Leib R.D., et al., "Direct Quantitation of Peptide Mixtures without Standards Using Clusters formed by Electrospray Ionization Mass Spectrometry," Analytical Chemistry, 2009, vol. 81 (10), pp. 3965-3972.

Lens J., "The Terminal Carboxyl Groups of Insulin," Biochimica et Biophysica Acta, 1949, vol. 3, pp. 367-370.

Levemir® prescribing information, Dec. 2011, pp. 1-6.

Levene P.A., et al., "Calculation of Isoelectric Point," The Journal of Biological Chemistry, 1923, vol. 55, pp. 801-813.

Levin P., et al., "Combination therapy with Insulin Glargine and Exenatide: Real-World Outcomes in Patients with Type 2 Diabetes," Current Medical Research and Opinion, 2012, vol. 28 (3), pp. 439-446.

Levine R.L., et al., "Oxidation of Methionine in Proteins: Roles in Antioxidant Defense and Cellular Regulation," IUBMB life, 2000, vol. 50 (4-5), pp. 301-307.

Leyer S., et al., "The Role of the C-Terminus of the Insulin B-Chain in Modulating Structural and Functional Properties of the Hormone," International Journal of Peptide and Protein Research, 1995, vol. 46 (5), pp. 397-407.

Li H., et al., "Chronic Treatment of Exendin-4 Affects Cell Proliferation and Neuroblast Differentiation in the Adult Mouse Hippocampal Dentate Gyrus," Neuroscience letters, 2010, vol. 19, pp. 1205-1219.

(56) References Cited

OTHER PUBLICATIONS

Li L., et al., "Common Pathological Processes in Alzheimer Disease and Type 2 Diabetes: a Review," Brain Research Reviews, 2007, vol. 56, pp. 384-402.

Li Y., et al., "Enhancing the GLP-1 Receptor Signaling Pathway Leads to Proliferation and Neuroprotection in Human Neuroblastoma Cells," Journal of Neurochemistry, 2010, vol. 113 (6), pp. 1621-1631.

Li Y., et al., "GLP-1 Receptor Stimulation Preserves Primary Cortical and Dopaminergic Neurons in Cellular and Rodent Models of Stroke and Parkinsonism," Proceedings of the National Academy of Sciences of the United States of America, 2009, vol. 106 (4), pp. 1285-1290.

Li Y., et al., "GLP-1 Receptor Stimulation Reduces Amyloid-Beta Peptide Accumulation and Cytotoxicity in Cellular and Animal Models of Alzheimer's Disease," Journal of Alzheimer's Disease, 2010, vol. 19 (4), pp. 1205-1219.

Lill N., "Production of Fast-Acting Insulins and Delayed-Release Insulins—How can this Problem be Solved by Technology? Insulin formulations," Pharmazie in Unserer Zeit, 2001, vol. 30 (1), pp. 56-61.

Liu & Ruus, Abstract "Pharmacokinetics and Safety of the GLP-1 Agonist AVE0010 in Patients with Renal Impairment," Diabetes 58 (Suppl. 1): Abstract 557-P for the 69th Scientific Session of the American Diabetes Association Jun. 5-9, 2009, New Orleans, Louisiana, pp. 1-2.

Lixisenatide, Chemical Structure CID 16139342, Pubchem, accessed Feb. 5, 2015 at URL pubchem.ncbi.nlm.nih.gov/summary/summary.cgi?sid=135267128&viewopt=Deposited, pp. 1-3.

Insulinpraparat Wikipedia, http://de.wikipedia.org/wiki/Insulinpr%C3%A4parat, pp. 1-15 (Feb. 5, 2013).

Insuman® Comb25 prescribing information, Feb. 2011, pp. 1-4.

Insuman® Infusat prescribing information, Feb. 2011, pp. 1-4.

Lotharius J., et al., "Effect of Mutant Alpha-Synuciein on Dopamine Homeostasis in a New Human Mesencephalic Cell Line," The Journal of Biological Chemistry, 2002, vol. 277 (41), pp. 38884-38894.

Lotharius J., et al., "Progressive Degeneration of Human Mesencephalic Neuron-Derived Cells Triggered by Dopamine-Dependent Oxidative Stress is Dependent on the Mixed-Lineage Kinase Pathway," Journal of Neuroscience, 2005, vol. 25 (27), pp. 6329-6342.

Lougheed W.D., et al., "Physical Stability of Insulin Formulations," Diabetes, 1983, vol. 32 (5), pp. 424-432.

Lyxumia 10 micrograms solution for injection, Summary of Product Characteristics, updated Oct. 31, 2014, pp. 1-12.

Lyxumia® ANNEX I—Summary of product characteristics. Date of first authorisation: Feb. 1, 2013, pp. 1-92.

Lyxumia, Chemical Subgroup A10BX, Community Register of Medicinal Products for Human Use, Eurpean Commission Public Health, p. 1-2 (May 2, 2013).

Lyxumia® Product Information—European Medicines Agency, first published Mar. 14, 2013, pp. 1-2.

Mancuso M., et al., "Clinical Features and Pathogenesis of Alzheimer's Disease: involvement of Mitochondria and Mitochondrial DNA," Advances in Experimental Medicine and Biology, 2010, vol. 685, pp. 34-44.

Marbury T.C., et al., "A Pilot Study to Examine the Feasibility of Insulin Glargine in Subjects with Impaired Fasting Glucose, Impaired Glucose tolerance or New-onset Type 2 Diabetes," Experimental and Clinical Endocrinology & Diabetes, 2008, vol. 116 (5), pp. 282-288.

Margolis R.L., et al., "Diagnosis of Huntington Disease," Clinical Chemistry, 2003, vol. 49 (10), pp. 1726-1732.

Markussen J., et al., "Soluble, Prolonged-Acting Insulin Derivatives. I. Degree of Protraction and Crystallizability of Insulins Substituted in the Termini of the B-Chain," Protein Engineering, 1987, vol. 1 (3), pp. 205-213.

Markussen J., et al., "Soluble, Prolonged-Acting Insulin Derivatives II Degree of Protraction and Crystallizability of Insulins Substituted in Positions A17, B8, B13, B27 and B30," Protein Engineering, 1987, vol. 1 (3), pp. 215-223.

Markussen J., et al., "Soluble, Prolonged-Acting Insulin Derivatives. III. Degree of Protraction, Crystallizability and Chemical Stability of Insulins Substituted in Positions A21, B13, B23, B27 and B30," Protein Engineering, 1988, vol. 2 (2), pp. 157-166.

Martin B., et al., "Exendin-4 Improves Glycemic Control, Ameliorates Brain and Pancreatic Pathologies, and Extends Survival in a Mouse Model of Huntington's Disease," Diabetes, 2009, vol. 58 (2), pp. 318-328.

Martin L.J., et al., "Neurodegeneration in Excitotoxicity, Global Cerebral Ischemia, and Target Deprivation: A Perspective on the Contributions of Apoptosis and Necrosis," Brain Research Bulletin, 1998, vol. 46 (4), pp. 281-309.

Mattson M.P., "Calcium and Neurodegeneration," Aging Cell, 2007, vol. 6 (3), pp. 337-350.

McClean P.L., et al., "Glucagon-Like Peptide-1 Analogues Enhance Synaptic Plasticity in the Brain: A Link between Diabetes and Alzheimer's Disease," European Journal of Pharmacology, 2010, vol. 630 (1-3), pp. 158-162.

McClean P.L., et al., "The Diabetes Drug Liraglutide Prevents Degenerative Processes in a Mouse Model of Alzheimer's Disease," The Journal of Neuroscience, 2011, vol. 31 (17), pp. 6587-6594.

Mecklenburg R.S., et al., "Complications of Insulin Pump therapy: The Effect of Insulin Preparation," Diabetes Care, 1985, vol. 8 (4), pp. 367-370.

Medline Plus, "Obesity" available at http://www.nlm.nih.gov/medlineplus/obesity.html, Retrieved Aug. 22, 2013, one page.

Meier J.J., "GLP-1 Receptor Agonists for individualized Treatment of Type 2 Diabetes Mellitus," Nature Reviews. Endocrinology, 2012, vol. 8 (12), pp. 728-742.

Merrifield B., "Solid Phase Synthesis," Science, 1986, vol. 232 (4748), pp. 341-347.

Mikhail N.E., "Is Liraglutide a Useful Addition to Diabetes therapy?," Endocrine Practice, 2010, vol. 16 (6), pp. 1028-1037.

Monnier L., et al., "The Loss of Postprandial Glycemic Control Precedes Stepwise Deterioration of Fasting with Worsening Diabetes," Diabetes Care, 2007, vol. 30 (2), pp. 263-269.

Moreno-Gonzalez I., et al., "Extracellular Amyloid-B and Cytotoxic Glial Activation Induce Significant Entorhinal Neuron Loss in Young PS1M146L/APP751SL Mice," Journal of Alzheimer's Disease, 2009, vol. 18, pp. 755-776.

Moretto T.J., et al., "Efficacy and tolerability of Exenatide Monotherapy Over 24 Weeks in Antidiabetic Drug-Naive Patients with Type 2 Diabetes: A Randomized, Double-Blind, Placebo-Controlled, Parallel-Group Study," Clinical Therapeutics, 2008, vol. 30 (8), pp. 1448-1460.

Muller G., et al., "Insulin Signaling in the Yeast *Saccharomyces cerevisiae*. 1. Stimulation of Glucose Metabolism and Snf 1 Kinase by Human Insulin," Biochemistry, 1998, vol. 37 (24), pp. 8683-8695.

Muzaffar M., et al., "The Mechanism of Enhanced Insulin Amyloid Fibril formation by Naciis Better Explained by a Conformational Change Model," PLoS One, 2011, vol. 6 (11), pp. 1-11.

Nakagawa A., et al., "Receptor Gene Expression of Glucagon-Like Peptide-1, but not Glucose-Dependent Insulinotropic Polypeptide, in Rat Nodose Ganglion Cells," Autonomic Neuroscience, 2004, vol. 110, pp. 36-43.

Nathan D.M., et al., "Management of Hyperglycaemia in Type 2 Diabetes Mellitus: A Consensus Algorithm for the initiation and Adjustment of therapy. Update Regarding the Thiazolidinediones," Diabetologia, 2008, vol. 51 (1), pp. 8-11.

Nathan M.D., et al., "Insulinotropic Action of Glucagon Like Peptide-1-(7-37) in Diabetic and Nondiabetic Subjects," Diabetes Care, 1992, vol. 15 (2), pp. 270-276.

Nauck M.A., et al., "Comparative Evaluation of Incretin-Based Antidiabetic Medications and Alternative therapies to be Added to Melformin in the Case of Monotherapy Failure," Journal of Diabetes Investigation, 2010, vol. 1 (1-2), pp. 24-36.

(56) References Cited

OTHER PUBLICATIONS

Nauck M.A., et al., "Effects of Subcutaneous Glucagon-Like Peptide 1 (GLP-1 [7-36 Amide]) in Patients with NIDDM," Diabetologia, 1996, vol. 39 (12), pp. 1546-1553.
Nauck M.A., et al., "Glucagon-Like Peptide 1 and its Potential in the Treatment of Non-Insulin-Dependent Diabetes Mellitus," Hormone and Metabolic Research, 1997, vol. 29 (9), pp. 411-416.
NCT00299871, ClinicalTrials.gov, "Dose Ranging Study of the GLP-1 Agonist AVE0010 in Metformin-Treated Subjects With Type 2 Diabetes Mellitus," Jun. 22, 2010, Retrieved Nov. 7, 2011, pp. 1-5.
NCT00688701 Clinical Trials.gov "GLP-1 Receptor Agonist Lixisenatide in Patients with Type 2 Diabetes for Glycemic Control and Safety Evaluation in Monotherapy (Getgoal-Mono)" accessed Jul. 27, 2014; pp. 1-5.
NCT00712673, Clinical Trials.gov, "GLP-A Agonist AVE0010 (Morning or Evening) in Patients with Type 2 Diabetes for Glycemic Control and Safety Evaluation, on Top of Metformin", Mar. 22, 2011, pp. 1-4.
NCT00715624 Clinical Trials.gov "GLP-1 Agonist AVE0010 in Patients With Type 2 Diabetes for Glycemic Control and Safety Evaluation, on Top of Basal Insulin" (updated Jul. 20, 2008), p. 1-3.
NCT00715624 Clinical Trials.gov "GLP-1 Receptor Agonist Lixisenatide in Patients With Type 2 Diabetes for Glycemic Control and Safety Evaluation, on Top of Basal Insulin (Getgoal-L)" (2008-2014), p. 1-6 (Feb. 2011).
Final Rejection issued in U.S. Appl. No. 13/382,442; dated Aug. 11, 2015, pp. 1-35.
NCT00763815, ClinicalTrials.gov, U.S. National Institutes of Health: "GLP-1 Agonist AVE0010 in Patients With Type 2 Diabetes for Glycemic Control and Safety Evaluation on Top of Pioglitazone (Getgoal-P)" pp. 1-8 (Jun. 27, 2011).
NCT00975286, Clinical Trials.gov, "24-week Treatment with Lbdsenalide in Type 2 Diabetes Insufficiently Controlled With Metformin and Insulin Glargine", Aug. 8, 2011, pp. 1-4.
NCT00976937, ClinicalTrials.gov, "24-week Study Comparing Lixisenatide (AVE0010) to Sitagliptin as add-on to Metformin in Obese Type 2 Diabetic Patients Younger Than 50," May 6, 2011, Retrieved Nov. 7, 2011, pp. 1-4.
NCT01146678, ClinicalTrials.gov "Relative Bioavailability and Activity of Different Formulations of Insulin Glargine and Lixisenatide in Patients With Diabetes Mellitus Type 1" last updated Sep. 10, 2010, pp. 1-4.
NCT01174810, ClinicalTrials.gov "Exendin-4 as a Treatment for Parkinson's Disease—Pilot Study" accessed Aug. 8, 2011, pp. 1-5.
NCT01195454, NIH Clinical Trials, "Euglycemic clamp dose-response study comparing insulin glargine U300 with Lantus U100" last updated Dec. 13, 2010, pp. 1-4.
NCT01255163, ClinicalTrials.gov "A Clinical Trial of Exendin-4 for the Treatment of Alzheimer's Disease" accessed Aug. 8, 2011, pp. 1-7.
NCT02058147 ClinicalTrials.gov "Efficacy and Safety of Insulin Glargine/Lixisenatide Fixed Ratio Combination Compared to Insulin Glargine Alone and Lixisenatide Alone on Top Metformin in Patients With T2DM (LixLan-O)" first received by ClinicalTrials. gov on Feb. 6, 2014, pp. 1-3.
NCT02058160 ClinicalTrials.gov "Efficacy and Safety of the Insulin Glargine/Lixisenatide Fixed Ratio Combination Versus Insulin Glargine in Patients With Type 2 Diabetes (LixiLan-L)" first received by ClinicalTrials.gov on Feb. 6, 2014, pp. 1-3.
Needleman S.B., et al., "A General Method Applicable to the Search for Similarities in the Amino Acid Sequence of Two Proteins," Journal of Molecular Biology, 1970, vol. 48 (3), pp. 443-453.
Neidle, "18.2 Failure Modes in the Discovery Process" Cancer Drug Design and Discovery, Elsevier/Academic Press, pp. 427-431 (2008).
Nettleton E.J., et al., "Characterization of the Oligomeric States of Insulin in Self-Assembly and Amyloid Fibril formation by Mass Spectrometry," Biophysical Journal, 2000, vol. 79 (2), pp. 1053-1065.
Nicklas et al., "Inhibition of Nadh-Linked Oxidation in Brain Mitochondria by 1-Methyl-4-Phenyl-Pyridine, A Metabolite of the Neurotoxin, 1-Methyl-4-Phenyl-1,2,5,6-Tetrahydropyridine," Life Sciences, 1985, vol. 36, pp. 2503-2508.
Nielsen L.L., et al., "Pharmacology of Exenatide (Synthetic Exendin-4): A Potential therapeutic for Improved Glycemic Control of Type 2 Diabetes," Regulatory Peptides, 2004, vol. 117 (2), pp. 77-88.
Noble S.L., et al., "Insulin Lispro: A Fast-Acting Insulin Analog," American Family Physician, 1998, vol. 57 (2), pp. 279-286.
Non-Final Office Action from U.S. Appl. No. 12/617,805; dated Jul. 24, 2014, pp. 1-12.
Non-Final Office Action from U.S. Appl. No. 12/617,805; dated May 2, 2012, pp. 1-11.
Non-Final Office Action from U.S. Appl. No. 12/617,805; dated May 10, 2011, pp. 1-12.
Non-Final Office Action from U.S. Appl. No. 12/617,805; dated Sep. 15, 2015, pp. 1-12.
Non-Final Office Action issued in U.S. Appl. No. 13/602,913; dated Dec. 2, 2014, pp. 1-12.
Non-Final Office Action issued in U.S. Appl. No. 13/602,913; dated Jan. 13, 2014, pp. 1-53.
Non-Final Office Action issued in U.S. Appl. No. 13/602,913; dated May 17, 2013, pp. 1-7.
Non-Final Rejection in U.S. Appl. No. 13/633,496; dated Apr. 29, 2013, pp. 1-53.
Non-Final Rejection in U.S. Appl. No. 13/633,496; dated Apr. 6, 2015, pp. 1-14.
Non-Final Rejection in U.S. Appl. No. 13/633,496; dated May 22, 2014, pp. 1-11.
Non-Final Rejection in U.S. Appl. No. 13/633,563; dated Dec. 1, 2014, pp. 1-9.
Non-Final Rejection in U.S. Appl. No. 13/633,563; dated Jul. 1, 2013, pp. 1-56.
Non-Final Rejection in U.S. Appl. No. 13/633,563; dated Jun. 4, 2014, pp. 1-11.
Non-Final Rejection in U.S. Appl. No. 13/633,583; dated Oct. 6, 2015, pp. 1-12.
Non-Final Rejection issued in U.S. Appl. No. 14/172,151; dated Mar. 24, 2015, pp. 1-16.
Non-Final Rejection issued in U.S. Appl. No. 12/817,811; dated Apr. 27, 2011, pp. 1-10.
Non-Final Rejection issued in U.S. Appl. No. 12/817,811; dated Jan. 14, 2015, pp. 1-15.
Non-Final Rejection issued in U.S. Appl. No. 12/617,811; dated Jun. 21, 2012, pp. 1-7.
Non-Final Rejection issued in U.S. Appl. No. 12/617,811; dated Oct. 27, 2011, pp. 1-13.
Non-Final Rejection issued in U.S. Appl. No. 13/110,568; dated Mar. 19, 2012, pp. 1-18.
Non-Final Rejection issued in U.S. Appl. No. 13/310,118; dated Mar. 19, 2012, pp. 1-19.
Non-Final Rejection issued in U.S. Appl. No. 13/310,118; dated Mar. 29, 2013, pp. 1-21.
Non-Final Rejection issued in U.S. Appl. No. 13/310,118; dated Mar. 25, 2015, pp. 1-15.
Non-Final Rejection issued in U.S. Appl. No. 13/363,956; dated Apr. 10, 2013, pp. 1-15.
Non-Final Rejection issued in U.S. Appl. No. 13/363,956; dated Feb. 11, 2015, pp. 1-18.
Non-Final Rejection issued in U.S. Appl. No. 13/363,956; dated May 29, 2015, pp. 1-17.
Non-Final Rejection issued in U.S. Appl. No. 13/363,956; dated Nov. 20, 2013, pp. 1-10.
Non-Final Rejection issued in U.S. Appl. No. 13/382,442; dated Nov. 7, 2012, pp. 1-26.
Non-Final Rejection issued in U.S. Appl. No. 13/382,442; dated Dec. 19, 2013, pp. 1-29.
Non-Final Rejection issued in U.S. Appl. No. 13/382,442; dated Feb. 5, 2015, pp. 1-31.
Non-Final Rejection issued in U.S. Appl. No. 13/382,772; dated Nov. 21, 2013, pp. 1-42.
Non-Final Rejection issued in U.S. Appl. No. 13/382,772; dated Sep. 29, 2014, pp. 1-33.
Non-Final Rejection issued in U.S. Appl. No. 13/382,772; dated Sep. 14, 2015, pp. 1-42.

(56) References Cited

OTHER PUBLICATIONS

Non-Final Rejection issued in U.S. Appl. No. 13/467,707; dated Jul. 15, 2013, pp. 1-20.
Non-Final Rejection issued in U.S. Appl. No. 13/467,707; dated Jul. 25, 2014, pp. 1-22.
Non-Final Rejection issued in U.S. Appl. No. 13/467,707; dated Sep. 16, 2015, pp. 1-13.
Non-Final Rejection issued in U.S. Appl. No. 13/468,422; dated Nov. 4, 2015; pp. 1-27.
Non-Final Rejection issued in U.S. Appl. No. 13/469,633; dated Aug. 19, 2013, pp. 1-25.
Non-Final Rejection issued in U.S. Appl. No. 13/469,633; dated Aug. 22, 2014, pp. 1-23.
Non-Final Rejection issued in U.S. Appl. No. 13/469,833; dated Mar. 27, 2013, pp. 1-39.
Non-Final Rejection issued in U.S. Appl. No. 13/509,507; dated Aug. 6, 2013, pp. 1-11.
Non-Final Rejection issued in U.S. Appl. No. 13/509,507; dated Sep. 19, 2014, pp. 1-9.
Non-Final Rejection issued in U.S. Appl. No. 13/509,507; dated Feb. 19, 2015, pp. 1-10.
Non-Final Rejection issued in U.S. Appl. No. 13/509,507; dated Dec. 8, 2015, pp. 1-14.
Non-Final Rejection issued in U.S. Appl. No. 13/509,542; dated May 23, 2013, pp. 1-21.
Non-Final Rejection issued in U.S. Appl. No. 13/509,542; dated Apr. 2, 2014, pp. 1-20.
Non-Final Rejection issued in U.S. Appl. No. 13/509,542; dated Aug. 11, 2015, pp. 1-30.
Non-Final Rejection issued in U.S. Appl. No. 13/595,590; dated Jun. 5, 2015, pp. 1-9.
Non-Final Rejection issued in U.S. Appl. No. 13/595,590; dated Oct. 16, 2013, pp. 1-7.
Non-Final Rejection issued in U.S. Appl. No. 13/595,590; dated Sep. 5, 2014, pp. 1-10.
Non-Final Rejection issued in U.S. Appl. No. 13/661,476; dated Jun. 4, 2015, pp. 1-31.
Non-Final Rejection issued in U.S. Appl. No. 13/661,476, dated Dec. 4, 2013, pp. 1-11.
Non-Final Rejection issued in U.S. Appl. No. 13/661,476, dated Mar. 6, 2014, pp. 1-28.
Non-Final Rejection issued in U.S. Appl. No. 13/661,476, dated Sep. 16, 2013, pp. 1-19.
Non-Final Rejection issued in U.S. Appl. No. 13/692,640; dated May 6, 2014, pp. 1-10.
Non-Final Rejection issued in U.S. Appl. No. 13/692,640; dated Oct. 31, 2013, pp. 1-10.
Non-Final Rejection issued in U.S. Appl. No. 13/700,631; dated Apr. 22, 2013, pp. 1-27.
Non-Final Rejection issued in U.S. Appl. No. 13/700,631; dated Dec. 17, 2015, pp. 1-18.
Non-Final Rejection issued in U.S. Appl. No. 13/700,631; dated Nov. 18, 2014, pp. 1-22.
Non-Final Rejection issued in U.S. Appl. No. 13/700,631; dated Nov. 29, 2013, pp. 1-23.
Non-Final Rejection issued in U.S. Appl. No. 13/819,114; dated Dec. 2, 2015, pp. 1-14.
Non-Final Rejection issued in U.S. Appl. No. 13/819,114; dated Jul. 31, 2014, pp. 1-9.
Non-Final Rejection issued in U.S. Appl. No. 14/220,562; dated Apr. 8, 2015, pp. 1-18.
Non-Final Rejection issued in U.S. Appl. No. 14/303,895; dated May 21, 2015, pp. 1-11.
Non-Final Rejection issued in U.S. Appl. No. 14/303,895; dated Sep. 9, 2015, pp. 1-12.
Non-Final Rejection issued in U.S. Appl. No. 13/467,757; dated Apr. 17, 2013, pp. 1-9.
Non-Final Rejection issued in U.S. Appl. No. 13/468,422; dated Jun. 4, 2014, pp. 1-24.
Non-Final Rejection issued in U.S. Appl. No. 13/468,422; dated Mar. 27, 2013, pp. 1-27.
Non-Final Rejection issued in U.S. Appl. No. 13/468,422; dated Sep. 16, 2013, pp. 1-19.
Non-Final Rejection issued in U.S. Appl. No. 13/382,772; dated Apr. 10, 2013, pp. 1-48.
Non-Final-Rejection issued in U.S. Appl. No. 13/432,811; dated Apr. 8, 2013, pp. 1-7.
Non-Final-Rejection issued in U.S. Appl. No. 13/432,811; dated Jul. 29, 2014, pp. 1-8.
Non-Final-Rejection issued in U.S. Appl. No. 13/432,811; dated Sep. 9, 2015, pp. 1-11.
Novolog® product information, Oct. 2009, pp. 1-4.
NovoMix® prescribing information, Feb. 2011, pp. 1-5.
NovoRapid® prescribing infonnation, Jul. 2012, pp. 1-5.
Organization for Economic Co-Ooperation and Development; OECD Principles of Good Laboratory Practice and Compliance Monitoring (as revised in 1997); ENV/MC/CHEM (98)17:1-41 (Jan. 21, 1998).
Orskov C., "Glucagon-Like Peptide-1, A New Hormone of the Entero-insular Axis," Diabetologia, 1992, vol. 35 (8), pp. 701-711.
Ott P., et al., "Diabetes in Germany(Dig) Study a Prospective 4-Year-Follow-Up Study on the Quality of Treatment for Type 2 Diabetes in Daily Practice," Deutsche Medtzinische Wochenschrift, 2009, vol. 134 (7), pp. 291-297.
Park C.W., et al., "PPARalpha Agonist Fenofibrate Improves Diabetic Nephropathy in Db/Db Mice," Kidney International, 2006, vol. 69 (9), pp. 1511-1517.
Parkin "Guideline for Management of Postmeal Glucose" International Diabetes Federation, pp. 1-32 (Oct. 2007).
Patel & Advance Collaborative Group, "Effects of a Fixed Combination of Perindopril and indapamide on Macrovascular and Microvascular Outcomes in Patients with Type 2 Diabetes Mellitus (the Advance Trial): A Randomised Controlled Trial," Lancet, 2007, vol. 370 (9590), pp. 829-840.
Patel K., et al., "Chemical Pathways of Peptide Degradation. II. Kinetics of Deamidation of an Asparaginyl Residue in a Model Hexapeptide," Pharmaceutical Research, 1990, vol. 7 (8), pp. 703-711.
Pederson R.A., et al., "Improved Glucose tolerance in Zucker Fatty Rats by oral Administration of the Dipeptidyl Peptidase IV inhibitor Isoleucine Thiazolidide," Diabetes, 1998, vol. 47 (8), pp. 1253-1258.
Perfetti R., "Combining Basal Insulin Analogs with Glucagon-Like Peptide-1 Mimetics," Diabetes Technology & Therapeutics, 2011, vol. 13 (9), pp. 873-881.
Perry T., et al., "A Novel Neurotrophic Property of Glucagon-Like Peptide 1: A Promoter of Nerve Growth Factor-Mediated Differentiation in PC12 Cells," The Journal of Pharmacology and Experimental Therapeutics, 2002, vol. 300 (3), pp. 958-966.
Perry T., et al., "Evidence of GLP-1-Mediated Neuroprotection in an Animal Model of Pyridoxine-induced Peripheral Sensory Neuropathy," Experimental Neurology, 2007, vol. 203 (2), pp. 293-301.
Perry T., et al., "Protection and Reversal of Excitotoxic Neuronal Damage by Glucagon-Like Peptide-1 and Exendin-4," The Journal of Pharmacology and Experimental Therapeutics, 2002, vol. 302 (3), pp. 881-888.
Perry T., et al., "The Glucagon-Like Peptides: A Double-Edged therapeutic Sword?," Trends in Pharmacological Sciences, 2003, vol. 24 (7), pp. 377-383.
Perry T.A., et al., "A New Alzheimer's Disease interventive Strategy: GLP-1," Current Drug Targets, 2004, vol. 5 (6), pp. 565-571.
Pillion D.J., et al., "Dodecylmaltoside-Mediated Nasal and Ocular Absorption of Lyspro-Insulin: Independence of Surfactant from Multimer Dissociation," Pharmaceutical Research, 1998, vol. 15(10), pp. 1637-1639.
Pinget M., et al., "Efficacy and safety of lixisenatide once daily versus placebo in type 2 diabetes insufficiently controlled on pioglitazone (GetGoal-P)," Diabetes, Obesity and Metabolism, 2013, vol. 15 (11), pp. 1000-1007.
Pohl M., et al., "Molecular Cloning of the Heloderman and Exendin-4 cDNAs in the Lizard," The Journal of Biological Chemistry, 1998, vol. 273 (16), pp. 9778-9784.

(56) References Cited

OTHER PUBLICATIONS

Porter D.W., et al., "Four Weeks Administration of Liraglutide Improves Memory and Learning As Well As Glycaemic Control in Mice with High Fat Dietary-induced Obesity and Insulin Resistance," Diabetes, Obesity and Metabolism, 2010, vol. 12 (10), pp. 891-899.
Pradier L et al. "Animal Models of Alzheimer's disease." Demences (Dementias); eds. Duyckaerts C. and Pasquier F.; publisher Doin; 165-170 (Sep. 10, 2002; available Aug. 27, 2002).
Prandini N., "Methods of Measuring Gallbladder Motor Functions—the Need for Standardization: Scintigraphy," Digestive and Liver Disease, 2003, vol. 35 (Suppl 3), pp. S62-S66.
"Preferable." Merriam-Webster.com. Merriam-Webster, n.d. Web. Sep. 7, 2015. http://www.merriamwebster.com/dictionary/preferable).
Pugeat M., et al., "Insulin Resistance, Polycystic Ovary Syndrome and Metformin," Drugs, 1999, vol. 58 (Suppl 1), pp. 41-46.
Quianzon C.L., et al., "Lixisentide-Once Daily Glucagon-Like Peptide-1 Receptor Agonist in the Management of Type 2 Diabetes," US Endocrinology, 2011, vol. 7 (2), pp. 104-109.
Raccah D., et al., "When Basal Insulin therapy in Type 2 Diabetes Mellitus is not Enough-What Next?," Diabetes/Metabolism Research and Reviews, 2007, vol. 23 (4), pp. 257-264.
Raju R.P., et al., "Optimum Palliation of inoperable Hilar Cholangiocarcinoma: Comparative Assessment of the Efficacy of Plastic and Self-Expanding Metal Stents," Digestive Diseases and Sciences, 2011, vol. 56, pp. 1557-1564.
Ramos B., et al., "Early Neuropathology of Somatostatin/NPY Gabaergic Cells in the Hippocampus of a Ps1xAPP Transgenic Model of Alzheimer's Disease," Neurobiology of Aging, 2006, vol. 27 (11), pp. 1658-1672.
Rao A.D., et al., "Is the Combination of Sulfonylureas and Metformin Associated with an increased Risk of Cardiovascular Disease or all-Cause Mortality? A Meta-Analysis of Observational Studies," Diabetes Care, 2008, vol. 31 (8), pp. 1672-1678.
Ratner R.E., et al., "A Dose-Finding Study of the New GLP-1 Agonist Ave0010 In Type 2 Diabetes Insufficiently Controlled with Melformin," Diabetes, 2008, vol. 57 (Suppl 1), pp. A129. Abstract # 433-P.
Ratner R.E., et al., "Dose-Dependent Effects of the Once-Daily GLP-1 Receptor Agonist Lixisenatide in Patients with Type 2 Diabetes Inadequately Controlled with Metformin: A Randomized Double-Blind, Placebo-Controlled Trial," Diabetic Medicine, 2010, vol. 27 (9), pp. 1024-1032.
Ratner R.E., et al., "Post-Meal Pharmacodynamics Profile of Ave0010, A Once-Daily GLP-1 Receptor Agonist, in Patiens with Type 2 Diabetes Inadequately Controlled on Metformin," Diabetologia, 2009, vol. 52 (Suppl 1), pp. S60. Abstract 131.
Ratner R.E., et al., "A Dose-Finding Study of the New GLP-1 Agonist AVE0010 in Type 2 Diabetes Insufficiently Controlled with Metformin," Diabetes, 68th Annual Meeting of the American Diabetes Association, San Francisco, Jun. 6-10, 2008, vol. 57 (Suppl 1), p. A129. Poster.
Request for "Type C" Meeting letter sent by Michael Lutz addressed to Mary Parks, dated Apr. 21, 2006, pp. 1-10.
Richter, von Margret, "Oldtimer as Newcomer" Pharmazie, pp. 1-9; http://www.pharmazeutische-zeitung.de/pza/2002-12/pharm1.htm (Feb. 2002).
Riddle M., et al., "Contributions of Basal and Postprandial Hyperglycemia over a Wide Range of A 1 C Levels before and after Treatment Intensification in Type 2 Diabetes," Diabetes Care, 2011, vol. 34, pp. 2508-2514.
Riddle M.C., et al., "Adding Once-Daily Lixisenatide for Type 2 Diabetes Inadequately Controlled by Established Basal Insulin: A 24-Week, Randomized, Placebo-Controlled Comparison (Getgoal-L)," Diabetes Care, 2013, vol. 36 (9), pp. 2489-2496.
Riddle M.C., et al., "Adding once-Daily Lixisenatide for Type 2 Diabetes inadequately Controlled with Newly initiated and Continuously Titrated Basal Insulin Glargine," Diabetes Care, 2013, pp. 2497-2503.
Ritzel U., et al., "A Synthetic Glucagon-Like Peptide-1 Analog with Improved Plasma Stability," The Journal of Endocrinology, 1998, vol. 159 (1), pp. 93-102.
Rohrmann C.A., "Differential Diagnosis of Pancreatic and Biliary Duct Diseases," Diseases of the Abdomen and Pelvis Syllabus, 1999, pp. 170-174.
Rosenstock et al., Abstract, "71st Scientific Sessions" http://www.call4abstracts.com/ada/ada11d11b/index.php 02:22:24 pp. 1-3, (Nov. 2011).
Rosenstock J., et al., "Dose Range Effects of the New Once Daily GLP-1 Receptor Agonist Ave0010 Added to Metformin in Type 2 Diabetes," Diabetologia, 2008, vol. 51 (Suppl 1), pp. S66. Abstract 145.
Rosenstock J., et al., "Post-Meal Effects of Ave0010, A Once-Daily GLP-1 Receptor Agonist, in Type 2 Diabetes Inadequately Controlled on Metformin," Diabetes, 2009, vol. 58 (Suppl 1), pp. A151-A152. Abstract 564P.
Rosenstock J., et al., "Efficacy and Safety of Lixisenatide Once Daily vs Exenatiide Twice Daily in Type 2 DM Inadequately Controlled on Metformin (GetGoal-X)," 71st Scientific Sessions, Nov. 2011. Poster.
Rubino A., et al., "Delayed initiation of Subcutaneous Insulin therapy after Failure of oral Glucose-Lowering Agents in Patients with Type 2 Diabetes: A Population-Based Analysis in the UK," Diabetic Medicine, 2007, vol. 24 (12), pp. 1412-1418.
Sampson H.A., et al., "Second Symposium on the Definition and Management of Anaphylaxis: Summary Report—Second National institute of Allergy and infectious Disease/Food Allergy and Anaphylaxis Network Symposium," The Journal of Allergy and Clinical Immunology, 2006, vol. 117 (2), pp. 391-397.
Sanger F., et al., "The Amide Groups of Insulin," The Biochemical Journal, 1955, vol. 59 (3), pp. 509-518.
Sanofi and Zealand Pharma Press Release (Evaluate), "Additional Positive Results from Global Phase III Program With Lixisenatide for Type 2 Diabetes", (Apr. 12, 2011) pp. 1-3.
Sanofi's Lantus Draft Prescribing Information/Package Insert: "NDA 21-081 Draft package insert" (Sponsor revision #5) Date of submission: Apr. 20, 2000; see http://www.drugbank.ca/system/fds_labels/DB00047.pdf 1265922812; pp. 1-14.
Sanofi Press Release entitled "FDA Accepts Sanofi's New Drug Application for Basal Insulin Toujeo®," dated Jul. 8, 2014, pp. 1-2.
Sanofi Press Release; "Lyxumia (lixisenatide) in Combination with Basal insulin plus Oral Anti-Diabetics Significantly Reduced HbA1c and Post-Prandial Glucose"; Paris, France (Jun. 9, 2012) pp. 1-6.
Sanofi Press Release (Peron and Schaeffer), "Sanofi GetGoal Program on Lyxumia®, as an Add-on to Basal Insulin, Shows Significant Positive Phase III Results," Paris, France (May 31, 2011) pp. 1-2.
Sanofi Press release (Peron and Schaeffer); "Sanofi Reports Positive Results for Once-daily Lyxumia® (lixisenatide) in Combination with Lantus® (insulin glargine) in Type 2 Diabetes" Paris, France (Dec. 6, 2011) pp. 1-3.
Sanofi Press Release (Peron and Schaeffer), "Lyxumia® (lixisenatide) One-Step Regimen as Effective as Two-Step Regimen in Improving Glycemic Control in Type 2 Diabetes" Paris, France (Sep. 12, 2011) pp. 1-3.
Sanofi Press Release "Positive Results for Investigational Compound Lyxumia (Lixisenatide) Presented at American Diabetes Association's 71st Annual Scientific Sessions," (Jun. 24, 2011), pp. 1-5.
Sanofi Press Release (Sigurd), "Lixisenatide Significantly Reduces HbA1c Without Increasing Hypoglycemia in Patients Uncontrolled on Sulfonylureas", Pressmeddelande (Apr. 12, 2011) pp. 1-2.
Sanofi-aventis Press Release (Gabriel), "New Diabetes Compound AVE0010 Showed Clear Dose Response Results With Once-A-Day Injection in Phase IIb Study" Paris, France (Jun. 7, 2008) pp. 1-2.
Sanofi-aventis Press Release, "Once Daily Lixisenatide (AVE 0010) Given as Monotherapy Successfully Meets Phase III Study Endpoints in Diabetes" Paris, France (Apr. 15, 2010) pp. 1-2.
Sanofi-aventis Press Release (Peron and Schaeffer), "Sanofi-aventis Announces Positive Top-line Lixisenatide Phase III Results" Paris, France (Feb. 2, 2011) pp. 1-2.

(56) References Cited

OTHER PUBLICATIONS

Sanofi Press Release entitled "Sanofi Receives FDA Approval of Once-Daily Basal Insulin Toujeo®," dated Feb. 26, 2015, pp. 1-4.
Schapira A.H., "Causes of Neuronal Death in Parkinson's Disease," Advances in Neurology, 2001, vol. 86, pp. 155-162.
Schellenberger V., et al., "Attempts for Quantifying the S' Subsite Specificity of Serine Proteases, Selected Papers Presented at the 2nd International Meeting on the Molecular and Cellular Regulation of Enzyme Activity, Advances in the Biosciences, Peptides and Proteases," Recent Advances, 1987, vol. 65, pp. 159-166.
Schellenberger V., et al., "Protease-Catalyzed Kinetically Controlled Peptide Synthesis," Angewante Chemie, 1991, vol. 30 (11), pp. 1437-1449.
Schindowski K., et al., "Impact of Aging: Sporadic, and Genetic Risk Factors on Vulnerability to Apoptosis in Alzheimer's Disease," Neuromolecular Medicine, 2003, vol. 4 (3), pp. 161-178.
Schmitz C., et al., "Hippocampal Neuron Loss Exceeds Amyloid Plaque Load in a Transgenic Mouse Model of Alzheimer's Disease," The American Journal of Pathology, 2004, vol. 164 (4), pp. 1495-1502.
Schwartz G.P., et al., "A Superactive Insulin: [B10-Aspartic Acid]Insulin(Human)," Proceedings of the National Academy of Sciences of the United States of America, 1987, vol. 84 (18), pp. 6408-6411.
Search Report of the Indecopi for Patent Application in Peru No. 000643-2012/DIN, dated Jul. 23, 2015, pp. 1-2.
Search Report of the Intellectual Property Corporation of Malaysia for Malaysian Patent Application No. PI 2011006204; dated Sep. 15, 2015, pp. 1-3.
Secnik Boye K., et al., "Patient-Reported Outcomes in a Trial of Exenatide and Insulin Glargine for the Treatment of Type 2 Diabetes," Health and Quality of Life Outcomes, 2006, vol. 4 (80), pp. 1-8.
Seino Y., et al., "Report of the Committee on the Classification and Diagnostic Criteria of Diabetes Mellitus," Journal of the Japan Diabetes Society, 2010, vol. 53, pp. 450-467 (in Japanese) English summary also provided.
Seino Y., et al., "Randomized, Double-Blind, Placebo-Controlled Trial of the Once-Daily GLP-1 Receptor Agonist Lixisenatide in Asian Patients with Type 2 Diabetes Insufficiently Controlled on Basal Insulin with or without a Sulfonylurea (Getgoal-L-Asia)," Diabetes, Obesity and Metabolism, 2012, vol. 14 (10), pp. 910-917.
Sharplin P., et al., "Improved Glycaemic Control by Switching from Insulin NPH to Insulin Glargine: A Retrospective Observational Study," Cardiovascular Diabetology, 2009, vol. 8 (3), pp. 1-8.
Sherer T.B., et al., "Subcutaneous Rotenone Exposure Causes Highly Selective Dopaminergic Degeneration and A-Synuclein Aggregation," Experimental Neurology, 2003, vol. 179, pp. 9-16.
Sluzky V., et al., "Kinetics of Insulin Aggregation in Aqueous Solutions Upon Agitation in the Presence of Hydrophobic Surfaces," Proceedings of the National Academy of Sciences of the United States of America, 1991, vol. 88 (21), pp. 9377-9381.
Smolka M.B., et al., "Optimization of the Isotope-Coded Affinity Tag-Labeling Procedure for Quantitative Proteome Analysis," Analytical Biochemistry, 2001, vol. 297 (1), pp. 25-31.
Sporn M.B., et al., "Chemoprevention of Cancer," Carcinogenesis, 2000, vol. 21 (3), pp. 535-530.
St. John Providence Health Center, "Preventing Obesity" http://www.stjohnprovidence.org/HealthInfolib/swarticle.aspx?type=85&id= P07863, Retrieved Aug. 22, 2013, pp. 1-2.
Starkova N.T., "Clinical Endocrinology," Guide for physicians, Medicine, 1991, pp. 192-262.
Stolk R.P., et al., "Insulin and Cognitive Function in an Elderly Population the Rotterdam Study," Diabetes Care, 1997, vol. 20 (5), pp. 792-795.
Summary of Product Characteristics Lyxumia 10 micrograms solution for injection, pp. 1-93, published Mar. 14, 2013.
Sundby F., "Separation and Characterization of Acid-induced Insulin Transformation Products by Paper Electrophoresis in 7 M Urea," The Journal of Biological Chemistry, 1982, vol. 237 (11), pp. 3406-3411.
Tanner C.M., et al., "Rotenone, Paraquat, and Parkinson's Disease," Environmental Health Perspectives, 2011, vol. 119 (6), pp. 866-872.
Tempero M.A., "How I Treat Pancreatic Ductal Adenocarcinoma," Current Clinical Issues, Journal of Oncology Practice, 2008, vol. 4 (1), pp. 46-47.
Teramoto S., et al., "Exendin-4, a Glucagon-Like Peptide-1 Receptor Agonist, provides Neuroprotection in Mice Transient Focal Cerebral Ischemia," Journal of Cerebral Blood Flow and Metabolism, 2011, vol. 31 ( 8), pp. 1696-1705.
Tessari P., et al., "Insulin in Methionine and Homocysteine Kinetics in Healthy Humans: Plasma Vs intracellular Models," American Journal of Physiology. Endocrinology and Metabolism, 2005, vol. 288 (6), pp. E1270-E1276.
Tetich M., et al., "Neuroprotective Effects of (24R)-1,24-Dihydroxycholecalciferol in Human Neuroblastoma SH-SY5Y Cell Line," The Journal of Steroid Biochemistry and Molecular Biology, 2004, vol. 89-90 (1-5), pp. 365-370.
The Expert Committee on the Diagnosis and Classification of Diabetes Mellitus. Report of the Expert Committee on the Diagnosis and Classification of Diabetes Mellitus Diabetes Care, Jan. 1998, 21:Supplement 1 S5-S19.
Thong K.Y., et al., "Safety, Efficacy and tolerability of Exenatide in Combination with Insulin in the Association of British Clinical Diabetologists Nationwide Exenatide Audit," Diabetes, Obesity and Metabolism, 2011, vol. 13 (8), pp. 703-710.
Thurow H., et al., "Stabilisation of Dissolved Proteins against Denaturation at Hydrophobic Interfaces," Diabetologia, 1984, vol. 27 (2), pp. 212-218.
Toth M.L., et al., "Neurite Sprouting and Synapse Deterioration in the Aging Caenortiabditis Elegans Nervous System," The Journal of Neuroscience, 2012, vol. 32 (26), pp. 8778-8790.
Translation of pp. 1109, 1116 and 1117 of "Clinical Effectiveness of Long-Term Administration of BAY g5421 (Acarbose) on Insulin-Treated Diabetes," Jpn. Pharmacal. Ther 1996 vol. 24 No. 5: 1109-1129, pp. 1-4.
Translation of pp. 121 and 124 of Igaku to Yakugaku, "Utility of Voglibose Long-term Combined Therapy in Non-Insulin Dependent Diabtetic Patients with Little Effective of Sulfonylureas," 1999, vol. 42, No. 1: 121-129, pp. 1-3.
Translation of pp. 2346 and 2348 of Rinsho to Kenkyu, "Effectiveness of Combination Therapy Using Voglibose and Insulin in Patients with NIDDM," 1997, vol. 74, No. 9: 2346-2352, pp. 1-3.
Translation of pp. 750, 753 and 754 of Igaku No Ayumi, "Incretin Receptors," May 2010, vol. 233; No. 9: 750-754, pp. 1-4.
Turner R.C., et al., "Glycemic Control with Diet, Sulfonylurea, Metformin, or Insulin in Patients with Type 2 Diabetes Mellitus: Progressive Requirement for Multiple therapies (UKPDS 49)," JAMA, 1999, vol. 281 (21), pp. 2005-2012.
Tyler-Cross R., et al., "Effects of Amino Acid Sequence, Buffers, and Ionic Strength on the Rate and Mechanism of Deamidation of Asparagine Residues in Small Peptides," The Journal of Biological Chemistry, 1991, vol. 266 (33), pp. 22549-22556.
UK Prospective Diabetes Study (UKPDS) Group, "Effect of intensive Blood-Glucose Control with Metformin on Complications in Overweight Patients with Type 2 Diabetes (UKPDS 34)," Lancet, 1998, vol. 352 (9131), pp. 854-865.
UK Prospective Diabetes Study (UKPDS) Group, "Intensive Blood-Glucose Control with Sulphonylureas or Insulin Compared with Conventional Treatment and Risk of Complications in Patients with Type 2 Diabetes (UKPDS 33)," The Lancet, 1998, vol. 352, pp. 837-853.
"Suspension" Stedman's Medical Dictionary, 20th Edition, p. 1450 (Williams & Wilkins Co., Baltimore 1961).
"Suspension" Taber's Cyclopedic Medical Dictionary, 19th Edition, p. 2097 (F.A. Davis Co., Philadelphia 2001).
Valle J., et al., "Cisplatin Plus Gemcitabine Versus Gemcitabine for Biliary Tract Cancer," The New England Journal of Medicine, 2010, vol. 362 (14), pp. 1273-1281.

(56) References Cited

OTHER PUBLICATIONS

Van Delden, "Pancreas-Carcinoma, CT Assessment of Resectability," Radiology Department of the Academical Medical Centre, Apr. 2006, pp. 1-12.
Varadarajan S., et al., "Review: Alzheimer's Amyloid Beta-Peptide-Associated Free Radical Oxidative Stress and Neurotoxicity," Journal of Structural Biology, 2000, vol. 130 (2-3), pp. 184-208.
Venezia V., et al., "Apoptotic Cell Death and Amyloid Precursor Protein Signaling in Neuroblastoma SH-SY5Y Cells," Annals of the New York Academy of Sciences, 2004, vol. 1030, pp. 339-347.
Victoza® ANNEX I—Summary of product characteristics. First published 2009, pp. 1-32.
Victoza Press Release, "Diabetes drugs show promise in Alzheimer's" published Jan. 17, 2011, pp. 1-2.
Victoza® Product information—European Medicines Agency, first published Aug. 7, 2009, pp. 1-2.
Volund A., et al., "In Vitro and in Vivo Potency of Insulin Analogues Designed for Clinical Use," Diabetic Medicine, 1991, vol. 8 (9), pp. 839-847.
Vora J., et al., "Incretin-Based therapy in Combination with Basal Insulin: A Promising Tactic for the Treatment of Type 2 Diabetes," Diabetes & Metabolism, 2013, vol. 39 (1), pp. 6-15.
Wafa W.S., et al., "Use of U-500 Regular Insulin in Type 2 Diabetes," Diabetes Care, 2006, vol. 29 (9), pp. 2175-2176.
Wajchenberg B.L., "Clinical Approaches to Preserve Beta-Cell Function in Diabetes," Advances in Experimental Medicine and Biology, 2010, vol. 654, pp. 515-535.
Wan Z., et al., "Enhancing the Activity of Insulin at the Receptor Interface: Crystal Structure and Photo-Cross—Linking of A8 Analogues," Biochemistry, 2004, vol. 43 (51), pp. 16119-16133.
Wang L., et al., "Real-World Outcomes of US Employees with Type 2 Diabetes Mellitus Treated with Insulin Glargine or Neutral Protamine Hagedorn Insulin: A Comparative Retrospective Database Study," BMJ Open, 2013, vol. 3 (4), pp. e002348 1-9.
Ward J.D., "Diabetic Neuropathy," British Medical Bulletin, 1989, vol. 45 (1), pp. 111-126.
Watson G.S., et al., "Insulin increases CSF Abeta42 Levels in Normal Older Adults," Neurology, 2003, vol. 60 (12), pp. 1899-1903.
Weiss M.A., et al., "Activities of Monomeric Insulin Analogs at Position A8 are Uncorrelated with their thermodynamic Stabilities," The Journal of Biological Chemistry, 2001, vol. 276 (43), pp. 40018-40024.
Werner et al., "Abstract, Insulin Glargine U-100 Has a Favourable Time-Action Profile Compared to U-40 or NPH Insulin in Healthy, Normoglycaemic Dogs", Poster 37th Annual Meeting of Endocrine Society of India, Tirupati, A.P., India, ESICON, 2007, p. 2.
Werner U., et al., "Pharmacological Profile of Lixisenatide: A New GLP-1 Receptor Agonist for the Treatment of Type 2 Diabetes," Regulatory Peptides, 2010, vol. 164 (2-3), pp. 58-64.
White I.R., et al., "Randomized Clinical Trials with Added Rescue Medication: Some Approaches to their Analysis and interpretation," Statistics in medicine, 2001, vol. 20 (20), pp. 2995-3008.
Whittingham J.L., et al., "Insulin At pH 2: Structural Analysis of the Conditions Promoting Insulin Fibre formation," Journal of Molecular Biology, 2002, vol. 318 (2), pp. 479-490.
WHO BMI classification, accessed at URL apps.who.int/bmi/index.jsp?introPage=itrol_3.html, Sep. 9, 2013, one page.
WHO Drug Information vol. 22(2), list 99, p. 142 (lixisenatide) (Jul. 2008).
Widjaja A., et al., "UKPDS 20: Plasma Leptin, Obesity, and Plasma Insulin in Type 2 Diabetic Subjects," The Journal of Clinical Endocrinology and Metabolism, 1997, vol. 82 (2), pp. 654-657.
Wiernsperger N.F., et al., "The Antihyperglycaemic Effect of Metformin: Therapeutic and Cellular Mechanisms," Drugs, 1999, vol. 58 (Suppl 1), pp. 31-39.
Wirths O., et al., "Intraneuronal Abeta Accumulation Precedes Plaque formation in beta-Amyloid Precursor Protein and Presenilin-1 Double-Transgenic Mice," Neuroscience Letters, 2001, vol. 308 (1-2), pp. 116-120.
Wirths O., et al., "Intraneuronal APP/A Beta Trafficking and Plaque formation in Beta-Amyloid Precursor Protein and Presenilin-1 Transgenic Mice," Brain Pathology, 2002, vol. 12 (3), pp. 275-286.
Wirths O., et al., "Reelin in Plaques of Beta-Amyloid Precursor Protein and Presenilin-1 Double-Transgenic Mice," Neuroscience Letters, 2001, vol. 316 (3), pp. 145-148.
Wollen K.A., "Alzheimer's Disease: the Pros and Cons of Pharmaceutical, Nutritional, Botanical, and Stimulatory therapies, with a Discussion of Treatment Strategies from the Perspective of Patients and Practitioners," Alternative Medicine Review, 2010, vol. 15 (3), pp. 223-244.
Workgroup on Hypoglycemia, American Diabetes Association, "Defining and Reporting Hypoglycemia in Diabetes: A Report from the American Diabetes Association Workgroup on Hypoglycemia," Diabetes Care, 2005, vol. 28 (5), pp. 1245-1249.
Written Opinion of the ISA for International Application No. PCT/EP2011/058079, dated Mar. 22, 2012, pp. 1-8.
Xie H., et al., "Characterization of Protein Impurities and Site-Specific Modifications Using Peptide Mapping with Liquid Chromatography and Data Independent Acquisition Mass Spectrometry," Analytical Chemistry, 2009, vol. 81 (14), pp. 5699-5708.
Yki-Jarvinen H., et al., "Insulin Glargine or NPH Combined with Metformin in Type 2 Diabetes: The Lanmet Study," Diabetologia, 2006, vol. 49 (3), pp. 442-451.
Yki-Jarvinen H., "Thiazolidinediones," The New England Journal of Medicine, 2004, vol. 351 (11), pp. 1106-1118.
Yoon N.M., et al., "Exenatide Added to Insulin therapy: A Retrospective Review of Clinical Practice Over Two Years in an Academic Endocrinology Outpatient Setting," Clinical Therapeutics, 2009, vol. 31 (7), pp. 1511-1523.
Yu Z.P., et al., "Effect of Zinc Sulphate and Zinc Methionine on Growth, Plasma Growth Hormone Concentration, Growth Hormone Receptor and Insulin-Like Growth Factor-I Gene Expression in Mice," Clinical and Experimental Pharmacology & Physiology, 2005, vol. 32 (4), pp. 273-278.
Zealand Pharma Press Release entitled "Sanofi-Aventis finalize phase lia clinical study with GLP-1 agonist for type 2 diabetes licensed from Zealand Pharma" dated Mar. 3, 2005, one page.
Ziemer D.C., et al., "Clinical Inertia Contributes to Poor Diabetes Control in a Primary Care Setting," The Diabetes Educator, 2005, vol. 31 (4), pp. 564-571.
Ziessman H.A., et al., "Sincalide-Stimulated Cholescintigraphy: A Multicenter Investigation to Determine Optimal Infusion Methodology and Gallbladder Ejection Fraction Normal Values," Journal of Nuclear Medicine, 2010, vol. 51 (2), pp. 277-281.
Zimmet P., et al., "Clinical Efficacy of Metformin Against Insulin Resistance Parameters: Sinking the Iceberg," Review Article, Drugs, 1999, vol. 58 (Suppl 1), pp. 21-28.
Zinman B., et al., "Efficacy and Safety of the Human Glucagon-Like Peptide-1 Analog Liraglutide in Combination with Metformin and Thiazolidinedione in Patients with Type 2 Diabetes (LEAD-4 Met+TZD)," Diabetes Care, 2009, vol. 32 (7), pp. 1224-1230.
Zinman B., "The Physiologic Replacement of Insulin an Elusive Goal," The New England Journal of Medicine, 1989, vol. 321 (6), pp. 363-370.
Wikipedia® entry for "Standard deviation" dated Oct. 10, 2017, pp. 1-3.
Non-Final Rejection issued is U.S. Appl. No. 15/595,929; dated Sep. 20, 2017, pp. 1-9.
Non-Final Rejection issued in U.S. Appl. No. 15/237,285; dated Sep. 29, 2017, pp. 1-10.
Non-Final Rejection issued in U.S. Appl. No. 15/144,270; dated Dec. 13, 2017, pp. 1-25.
Non-Final Rejection issued in U.S. Appl. No. 15/411,557; dated Mar. 19, 2018, pp. 1-11.
Non-Final Rejection issued in U.S. Appl. No. 14/624,575; dated Mar. 26, 2015, pp. 1-14.
Non-Final Rejection issued in U.S. Appl. No. 15/162,563; dated Feb. 8, 2017, pp. 1-13.
Final Rejection issued in U.S. Appl. No. 15/162,563; dated Dec. 18, 2017, pp. 1-16.
Non-Final Office Action issued in U.S. Appl. No. 15/146,255; dated Sep. 18, 2017, pp. 1-10.

(56) References Cited

OTHER PUBLICATIONS

Final Rejection in U.S. Appl. No. 13/633,563; dated Apr. 28, 2017, pp. 1-12.
Non-Final Rejection issued in U.S. Appl. No. 14/995,910; dated Dec. 11, 2017, pp. 1-7.
Non-Final Rejection issued in U.S. Appl. No. 15/073,364; dated Nov. 9, 2017, pp. 1-8.
Extended European Search Report for European Application No. 16 19 0103.8; dated Jun. 23, 2017, pp. 1-5.
Extended European Search Report for European Application No. 17 20 2727.8; dated Dec. 20, 2017, pp. 1-9.
Search Report in Chinese Patent Application No. 201410818149.0; dated Jan. 10, 2017, pp. 1-3. English translation submitted.
Search Report of the Intellectual Property Office of Singapore for Patent Application No. 10201403840V; search completed Nov. 21, 2017 dated Jan. 4, 2017, pp. 1-3.
Adis R&D Profile "Insulin Glargine: Glargine, HOE 71GT15, HOE 71GT80, HOE 901", Drugs R&D 2(2)107-109 (Aug. 1999).
Ashford & Landi, "Stabilizing Properties of Tween 80 in Dilute Protein Solutions" Bull Parenteral Drug Assoc. 20(3):74-84 (May—Jun. 1966).
Aventis SEC Form 20-F; pp. 1-303 (Apr. 8, 2002).
Bam et al., "Tween protects recombinant human growth hormone against agitation-induced damage via hydrophobic interactions" J. Ph. Sci. 87(12):1554-59 (Dec. 1998).
Bam et al., "Stability of Protein Formulations: Investigation of Surfactant Effects by a Novel EPR Spectroscopic Technique," Pharmaceutical Research, 12(1):2-11 (Jan. 1995).
Bates et al., "Kinetics of hydrolysis of polyoxyethylene (20) sorbitan fatty acid ester surfactants," J. Pharmacy and Pharmacology 25(6):470-77 (Jun. 1973).
Berchtold & Hilgenfeld, "Binding of Phenol to R6 Insulin Hexamers" Biopolymers 51(2):165-72 (1999).
Caprio, "Obesity and Type 2 Diabetes: The Twin Epidemic" Diabetes Spectrum 16(4):230 (2003).
Chawla et al., "Aggregation of Insulin, Containing Surfactants, in Contact with Different Materials", Diabetes 34(5):420-24 (May 1985).
Clinical Trials Archive for Trial No. NCT00763815 updated Feb. 21, 2014. Accessed at https://clinicaltrials.gov/archive/NCT00763815/2014_02_21/changes Accessed on Nov. 13, 2017. pp. 1-13.
Colagiuri, "Diabesity: therapeutic options" Diabetes, Obesity and Metabolism 12(6):463-73 (Jun. 2010).
Definition of "hypoglycemia" Stedman's Medical Dictionary, 5th Edition, Japan, published on Feb. 20, 2002, p. 853; in Japanese, English translation also submitted.
Derewenda et al., "Phenol Stabilizes More Helix in a New Symmetrical Zinc Insulin Hexamer" Nature 338 (6216):594-96 (Apr. 1989).
Drug Facts and Comparison; J. B. Lippincot Company, St. Louis, MO; pp. 1781-1790 (1988).
EMEA Public Statement on INSUMAN INFASAT (Feb. 14, 2000), at http://www.ema.europa.eu/ema/index.jsp?curl=pages/news_and_events/news/2010/08/news_detail_001094.jsp&mid=WC0b01ac058004d5c1 (accessed Jun. 1, 2017); pp. 1-2.
European Medicines Agency, LYXUMIA 10/20 micrograms solution for injection, Summary of Product Characteristics, Date of first authorisation: Feb. 1, 2013, pp. 1-82 (retrieved from the internet on Mar. 12, 2018).
Excerpts from "Handbook of Pharmaceutical Excipients" 2nd Edition (eds. A. Wade and P.J. Weller) American Pharmaceutical Association, Washington, The Pharmaceutical Press, London; pp. 1-55 (1994).
Farag & Gaballa, "Diabesity: an overview of a rising epidemic" Nephrol Dial Transplant 26(1):28-35 (Jan. 2011; Epub Nov. 2, 2010).
FDA, "Guidance of Industry - Bioequivalence studies with pharmacokinetic endpoints for drugs submitted under an ANDA" Draft Guidance by the U.S. Department of Health and Human Services, Food and Drug Administration, Center for Drug Evaluation and Research (CDER), Dec. 2013, pp. 1-24.
Gatlin & Gatlin, "Formulation and Administration Techniques to Minimize Injection Pain and Tissue Damage Associated with Parenteral Products" in Injectable Drug Development, Chapter 17; pp. 401-421 (eds. P. K. Gupta and G.A. Brazeau) (CRC Press) (1999).
Gillies et al, "Insulin Glargine" Drugs 59(2)L253-60 (Feb. 2000).
Grau & Saudek, "Stable Insulin Preparation for Implanted Insulin Pumps", Diabetes 36(12):1453-59 (Dec. 1987).
Gualandi-Signorini & Giorgi, "Insulin formulations—a review" European Review for Medical and Pharmacological Sciences 5:73-83 (2001).
Hallas-Moller, "The Lente Insulins", Diabetes 5:7-14 (Jan. —Feb. 1956).
Heile & Schneider, "The Evolution of Insulin Therapy in Diabetes Mellitus", J Fam Pract 61(5 Suppl.):S6-12 (May 2012).
Insuman Infusat entry in Rote Liste, one page (2001).
Insuman Infusat; FASS Entry for INSUMAN INFUSAT; pp. 1-6 (Jan. 2000). English translation of Jun. 5, 2017, pp. 1-8 also submitted.
Jones, "Insulin Glargine Aventis Pharma", IDrugs 3(9):1081-87 (Sep. 2000).
Jones et al. "Surfactant-Stabilized Protein Formulations: A Review of Protein-Surfactant interactions and Novel Analytical Methodologies," Therapeutic Protein & Peptide Delivery, ACS Symposium Series; Chapter 12, pp. 206-222 (1997).
Katakam et al., "Effect of Surfactants on the Physical Stability of Recombinant Human Growth Hormone" J Pharm Sci 84(6):713-16 (Jun. 1995).
Lantus® 100U/ml solution for injection (insulin glargine); published in vol. 24 No. 9 of Pract. Diab. Int. Nov./Dec. 2007, p. 472.
Lantus® entry in Physician's Desk Reference; pp. 1-6 (2001).
Lantus®—FDA Drug Approval Letter for Lantus® (NDA 02-1081) at https://www.accessdata.fda.gov/scripts/cder/daf/index.cfm?event=overview.process&ApplNo=021081 (accessed Jan. 25, 2018), pp. 1-5.
Lantus®—FDA Drug Approval Label for Lantus® (NDA 02-1081) (Apr. 20, 2000) at https://www.accessdata.fda.gov/scripts/cder/daf/index.cfm?event=overview.process&ApplNo=021081 (accessed Jan. 25, 2018), pp. 1-14.
Lee et al., "Effect of Brij-78 on Systemic Delivery of Insulin from an Ocular Device" J Pharm Sci 86(4):430-33 (Apr. 1997).
Lee et al., "Review on the Systemic Delivery of Insulin via the Ocular Route" Int'l J Pharmaceutics 233(1-2):1-18 (Feb. 2002).
Lougheed et al., "Insulin Aggregation in Artificial Delivery Systems" Diabetologia 19(1):1-9 (Jul. 1980).
Manning et al., "Stability of Protein Pharmaceuticals," Pharm Research, 6(11):903-18 (Nov. 1989).
McKeage & Goa, "Insulin Glargine: A Review of its Therapeutic Use as Long-Acting Agent for the Management of Type 1 and Type 2 Diabetes Mellitus," Drugs 61(11):1599-1624 (Sep. 2001).
NCT01195454, NIH Clinical Trials, "Euglycemic clamp dose-response study comparing insulin glargine U300 with Lantus U100" last updated Sep. 3, 2010, pp. 1-3.
NCT00765817, Clinical Trials.gov "Addition of Exenatide to Insulin Glargine in Type 2 Diabetes Mellitus" last updated Oct. 26, 2016, last accessed Jan. 19, 2018, pp. 1-8.
Owens et al., "Pharmacokinetics of 125I-labeled insulin glargine (HOE 901) in healthy men: comparison with NPH insulin and the influence of different subcutaneous injection sites." Diabetes Care 23(6):813-19 (Jun. 2000).
Profile of Lantus® (insulin glargine injection) 100 units/ml vs. NPH in patients with type 1 diabetes; https://www.lantus.com/hcp/aboutlantus/vs-nph, pp. 1-4, last accessed Feb. 19, 2016.
Rosenstock et al., "Reduced Hypoglycemia Risk with Insulin Glargine: A meta-analysis comparing insulin glargine with human NPH insulin in type 2 diabetes" Diabetes Care 28(4):950-55 (Apr. 2005).
Sanofi-aventis Press Release (Melia), "New Diabetes Compound AVE0010 Showed Clear Dose Response Results With Once-A-Day Injection in Phase IIb Study" San Francisco, California (Jun. 7, 2008) pp. 1-3.

(56) References Cited

OTHER PUBLICATIONS

Schmolka, "Poloxamers in the Pharmaceutical Industry" in Polymers For Controlled Drug Delivery, Chapter 10, pp. 189-214 (CRC Press) (1991).
Shi, "The Newest Handbook of Clinical Drugs" Military Medical Science Press, p. 809, (Jan. 2008). English translation submitted.
Soeborg et al., "Absorption kinetics of insulin after subcutaneous administration" European Journal of Pharmaceutical Sciences 36(1):78-90 (Jan. 2009; Epub Nov. 5, 2008).
Tang, "Biotech Drugs—Introduction and Practice Handbook" Chemical Industry Press, pp. 635-36, (Jan. 2008). English translation submitted.
Wang, "Instability, Stabilization and Formulation of Liquid Protein Pharmaceuticals," Int'l J Pharm, 185(2):129-88 (Aug. 1999).
U.S. Appl. No. 15/803,589, filed Nov. 3, 2017, Hagendorf.
U.S. Appl. No. 15/730,033, filed Oct. 11, 2017, Niemöller.
U.S. Appl. No. 15/803,589, filed Nov. 3, 2017, Pharmaceutical Composition Comprising A GLP-1 Agonist, An Insulin and Methionine, Pending.
U.S. Appl. No. 15/730,033, filed Oct. 11, 2017, Pharmaceutical Combination For Improving Glycemic Control As Add-On Therapy To Basal Insulin, Pending.

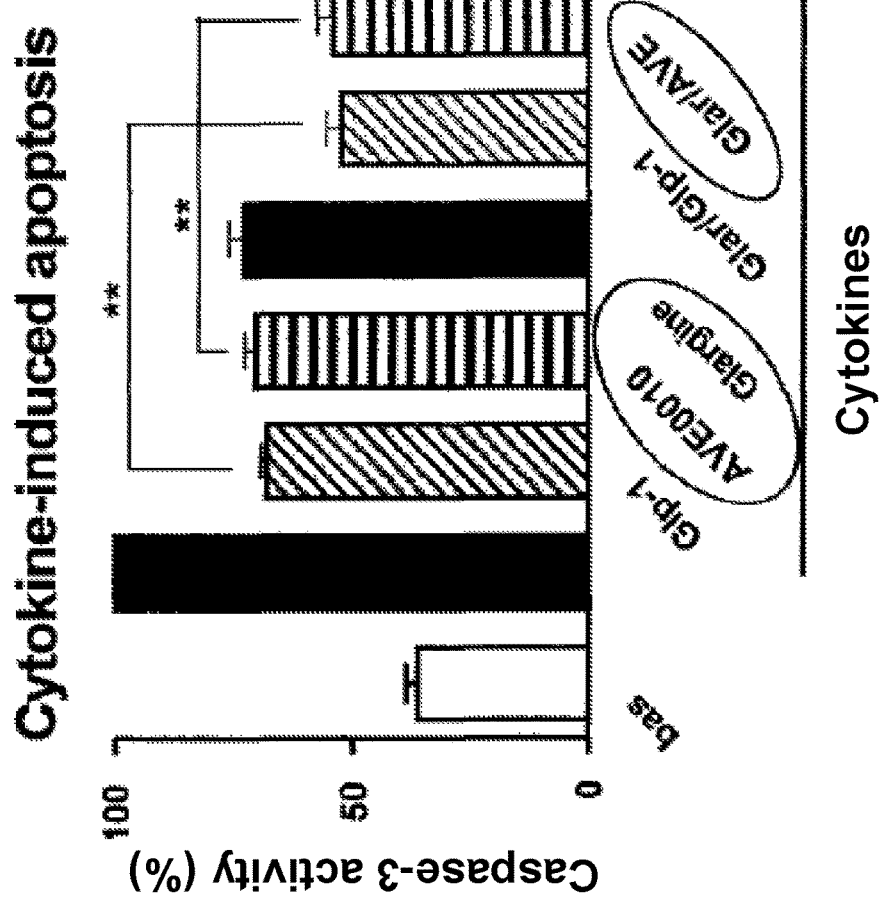

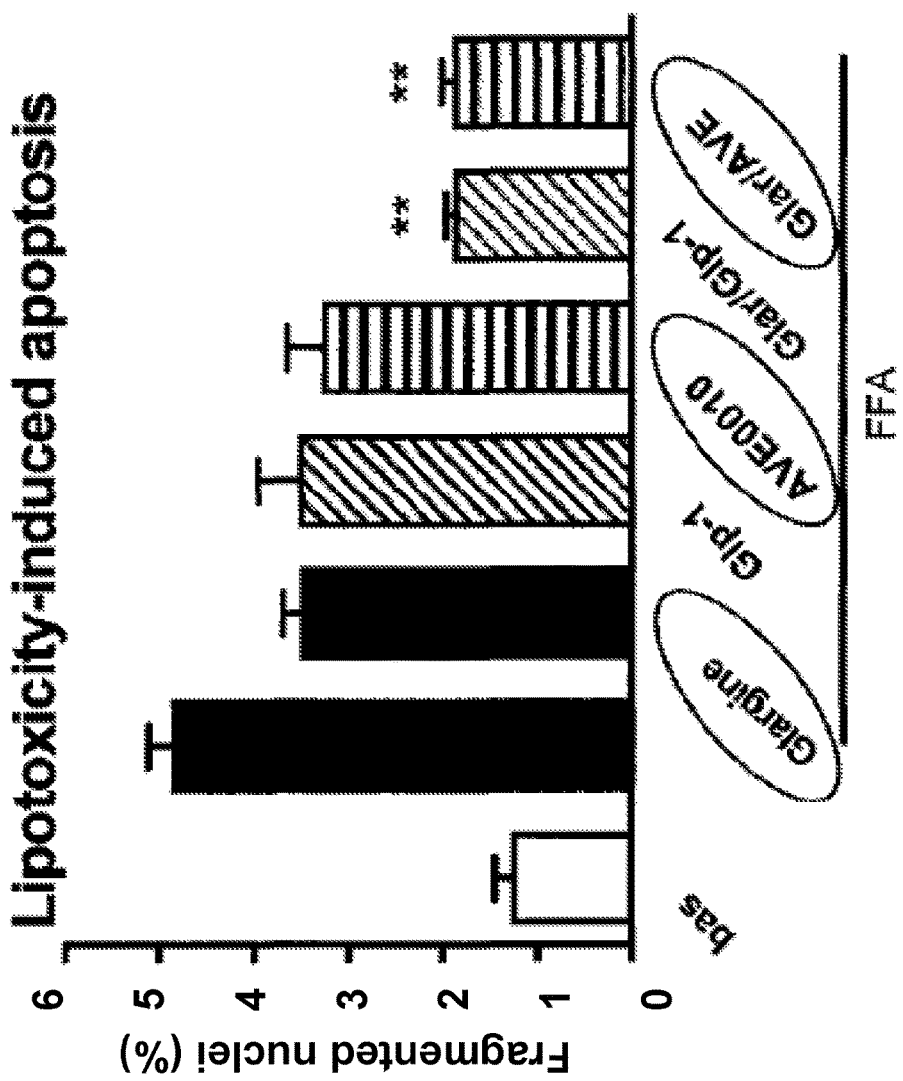

COMBINATION OF AN INSULIN AND A GLP-1 AGONIST

This application is a continuation application of U.S. application Ser. No. 13/123,835, now U.S. Pat. No. 9,526,764, filed Sep. 30, 2011, which is a national stage application under 35 U.S.C. § 371 of International Application No. PCT/EP2009/063195, filed on Oct. 9, 2009, and which claims the benefit of priority from German Patent Application No. 10 2009 038 210.0, filed Aug. 20, 2009, German Patent Application No. 10 2008 053 048.4, filed Oct. 24, 2008, and German Patent Application No. 10 2008 051 834.4, filed Oct. 17, 2008, the disclosures of each of which are explicitly incorporated by reference herein.

The invention relates to a medicament comprising at least one insulin and at least one GLP1 receptor agonist, referred to below as GLP-1 agonist, the medicament being formulated and/or compounded in such a way that it comprises the insulin and the GLP-1 agonist each in a predetermined amount and can be administered in a dose adapted to the individual requirement of a patient.

The invention relates more particularly to a medicament comprising a first pharmaceutical composition and a second pharmaceutical composition, and, optionally, at least one further pharmaceutical composition, which each comprise at least one insulin and at least one GLP-1 agonist and contain the at least one insulin and/or the at least one GLP-1 agonist in different fractions relative to the total weight of the composition.

More particularly the present invention relates to a medicament which comprises a first pharmaceutical composition and a second pharmaceutical composition, and, optionally, at least one further pharmaceutical composition, the first pharmaceutical composition comprising at least one insulin, and the second pharmaceutical composition comprising at least one insulin and at least one GLP-1 agonist, and the at least one further pharmaceutical composition comprising at least one insulin and at least one further active compound.

Around 250 million people worldwide suffer from diabetes mellitus. For the type 1 diabetics among them, replacement of the deficient endocrine insulin secretion is the only possible therapy at present. Those affected are dependent on insulin injections for life, usually several times a day. Type 2 diabetes contrasts with type 1 diabetes in that there is not always a deficiency of insulin, but in a large number of cases, especially at the advanced stage, treatment with insulin, where appropriate in combination with an oral antidiabetic. Is considered the most advantageous form of therapy.

In healthy individuals, insulin release by the pancreas is strictly coupled to the blood glucose concentration. Elevated blood glucose levels like those occurring after meals are rapidly compensated by a corresponding rise in insulin secretion. In the fasting state, the plasma insulin level falls to a baseline value which is sufficient to ensure a continuous supply of glucose to insulin-sensitive organs and tissues and to keep hepatic glucose production low during the night The replacement of the endogenous insulin secretion by exogenous, usually subcutaneous administration of insulin does not in general come close to the above-described quality of the physiological regulation of blood glucose. Frequently there are instances of blood glucose being thrown off-track, either upwardly or downwardly, and in their most severe forms these may be life-threatening. In addition, however, blood glucose levels which are elevated over years, without initial symptoms, constitute a considerable health risk. The large-scale DCCT study in the USA (The Diabetes Control and Complications Trial Research Group (1993) N. Engl. J. Med. 329, 977-986) showed unambiguously that chronically elevated blood glucose levels are responsible for the development of late diabetic complications. Late diabetic complications are micro- and macrovascular damage which is manifested in certain circumstances as retinopathy, nephropathy or neuropathy and leads to blindness, renal failure, and loss of extremities, and, in addition, is associated with an increased risk of cardiovascular disorders. From this it can be inferred that an improved therapy of diabetes must be aimed primarily at keeping blood glucose as closely as possible within the physiological range, According to the concept of intensified insulin therapy, this is to be achieved by means of injections, several times a day, of fast-acting and slow-acting insulin preparations, Fast-acting formulations are given at mealtimes in order to compensate the postprandial rise in blood glucose. Slow-acting basal insulins are intended to ensure the basic supply of insulin especially during the night, without leading to hypoglycemia.

Insulin is a polypeptide composed of 51 amino acids which are divided over 2 amino acid chains: the A chain, with 21 amino acids, and the B chain, with 30 amino acids. The chains are linked together by 2 disulfide bridges. Insulin preparations have been employed for many years for diabetes therapy. Such preparations use not only naturally occurring insulins but also, more recently, insulin derivatives and insulin analogs.

Insulin analogs are analogs of naturally occurring insulins, namely human insulin or animal insulins, which differ by replacement of at least one naturally occurring amino acid residue by other amino acids and/or addition/deletion of at least one amino acid residue from the corresponding, otherwise identical, naturally occurring insulin. The amino acids in question may also be amino acids which do not occur naturally.

Insulin derivatives are derivatives of naturally occurring insulin or of an insulin analog which are obtained by chemical modification. The chemical modification may consist, for example, in the addition of one or more defined chemical groups and to one or more amino acids. Generally speaking, the activity of insulin derivatives and insulin analogs is somewhat altered as compared with human insulin.

Insulin analogs with an accelerated onset of action are described in EP 0 214 826, EP 0 375 437, and EP 0 678 522. EP 0 214 826 relates, among other things, to replacements of B27 and B28. EP 0 678 522 describes insulin analogs which have different amino acids in position B29, preferably proline, but not glutamic acid. EP 0 375 437 encompasses insulin analogs with lysine or arginine in B28, which may optionally also be modified in B3 and/or A21. An accelerated activity is also exhibited by the insulin analogs described in EP-A-0 885 961.

EP 0 419 504 discloses insulin analogs which are protected from chemical modifications by modification of asparagine in B3 and of at least one further amino acid in positions A5, A15, A18 or A21.

WO 92/00321 describes insulin analogs in which at least one amino acid in positions 81-86 has been replaced by lysine or arginine. Such insulins, according to WO 92/00321, have an extended activity. A delayed activity is also exhibited by insulin analogs described in EP-A 0 368 187 and by the insulin analogs described in German patent applications 10 2008 003 568.8 and 10 2008 003 566.1.

The insulin preparations of naturally occurring insulins for insulin replacement that are on the market differ in the origin of the insulin (e.g., bovine, porcine, human insulin) and also in their composition, whereby the profile of action can be influenced (onset of action and duration of action). By combining different insulin products it is possible to obtain a wide variety of profiles of action and to set blood sugar levels which are as close as possible to physiological. Recombinant DNA technology nowadays allows the production of such modified insulins. These include insulin glargine (Gly(A21)-Arg(B31)-Arg(B32) human insulin), with an extended duration of action. Insulin glargine is injected as an acidic, clear solution and, on account of its solution properties in the physiological pH range of the subcutaneous tissue, is precipitated as a stable hexamer associate. Insulin glargine is injected once daily and is notable over other long-activity insulins for its flat serum profile and the associated reduction in the risk of nocturnal hypoglycemias (Schubert-Zsilavecz et al., 2:125-130 (2001)).

The specific preparation of insulin glargine that leads to a prolonged duration of action is characterized by a clear solution with an acidic pH.

Glucagon-like peptide 1 (GLP-1) is an endocrine hormone which increases the insulin response following oral intake of glucose or fat. GLP-1 generally regulates the concentrations of glucagons, slows down gastric emptying, stimulates the biosynthesis of (Pro-)insulin, increases the sensitivity toward insulin, and stimulates the insulin-independent biosynthesis of glycogen (Hoist (1999), Curr. Med. Chem 6:1005, Nauck et aL (1997) Exp Clin Endocrine! Diabetes 105: 187, Lopez-Delgado et al (1998) Endocrinology 139:2811).

Human GLP-1 has 37 amino acid residues (Heinrich et al., Endocrinol. 115:2176 (1984), Uttenthal et al, J Clin Endocrinol Metabol (1985) 61:472). Active fragments of GLP-1 include GLP-1(7-36) amide and GLP-1(7-37).

Exendins are another group of peptides which are able to lower blood glucose concentrations. Exendins have a certain similarity in sequence to GLP-1(7-36) (53%, Goke et al. J. Biol Chem 268, 19650-55). Exendin-3 and exendin-4 stimulate an increase in cellular cAMP production in acinar cells of the guinea pig pancreas by interaction with exendin receptors (Raufman, 1996, Reg. Peptides 61:1-18). In contrast to exendin-4, exendin-3 produces an increase in amylase release in acinar cells of the pancreas.

Exondin-3, exendin-4, and exendin agonists have been proposed for the treatment of diabetes mellitus and the prevention of hyperglycemia; they reduce gastric motility and gastric emptying (U.S. Pat. No. 5,424,286 and WO98/05351).

Exendin analogs may be characterized by amino acid replacements and/or C.-terminal truncation of the natural exendin-4 sequence. Exendin analogs of this kind are described in WO 99/07404, WO 99/25727, WO 99/25728.

Combinations of insulin and GLP-1 are known from WO 2004/005342 for the treatment of diabetes.

In clinical practice the amount of insulin to be administered is adjusted to the individual requirement of the individual diabetes patients. Individual patients generally need different amounts of insulin and/or GLP-1 agonist. Typically the predetermined dose is administered by administering a defined amount of a composition having a defined concentration. A result of this is that a composition which comprises insulin and GLP-1 at the same time allows the administration of only one particular proportion of insulin and GLP-1. This means that only one of the two amounts of insulin and GLP-1 can be adapted optimally to the requirement of the patients. Since in practice the correct adjustment of the amount of insulin administered is essential, it is assumed that, when a particular proportion of insulin to GLP-1 is administered, the GLP-1 agonist is either underdosed or overdosed and is correct by chance at best There are various systems known for injecting a combination of active compounds. The active compounds may be formulated in a composition and provided in a device, as for example in a prefilled syringe. A system of this kind does allow the dosing of the combination, but only in a fixed portion of the active compounds, as is present in the composition. As set out therein, this is a disadvantage for the combination of an insulin with a GLP-1 agonist, since different amounts of the insulins and of the GLP-1 agonist have to be administered, according to the therapeutic requirement.

It is also possible for two active compounds to be administered in two separate formulations, each comprising one of the two active compounds, which are injected independently of one another each with one device (e.g., prefilled syringes). In the case of an injection therapy such as the injection of insulin, for example, patient compliance is a key prerequisite for the success of the therapy. Generally speaking, in the case of an injection therapy, pain, needle-phobia, and the carrying facility for the injection apparatus are a problem, which can lead to reduced compliance. If the patient is to use two separate devices for injection, then these problems multiply.

A single device for the administration of insulin and a GLP-1 agonist is advantageous over the use of two separate devices for administering insulin and a GLP-1 agonist as far as the patient/user is concerned. Moreover, the use of only one device rather than two devices may reduce the number of steps which the patient/user must carry out, which lowers the frequency of errors in use. This reduces the risk of unwanted side effects.

U.S. Pat. No. 4,689,042, U.S. Pat. No. 5,478,323, U.S. Pat. No. 5,253,785, and WO 01/02039 describe devices for the simultaneous administration of two injectable products to a patient. These devices comprise two containers each containing one composition. In these devices the two compositions are injected via a needle. This does make it possible to overcome the disadvantages produced by the use of two separate devices. As a result of the mixing process, there is a dilution in the concentrations of the two active compounds. This may impact adversely on the pharmacokinetics.

The pharmacokinetics of insulin, particularly of insulin glargine, is influenced by the dilution of the Insulin in the administered composition. In order to ensure reliable activity of a particular dose of insulin, therefore, the concentration of insulin ought to be kept constant as far as possible. Dosing ought to take place essentially via the volume of the insulin composition administered. This is also true for the administration of a combination of insulin and a GLP-1 agonist. When a combination of insulin and a GLP-1 agonist is administered, this proviso can only be met if both substances are dosed in a fixed proportion to one another in one composition. Where both substances are provided in separate compositions and are mixed for injection in a suitable device (e.g., from WO 01/02039), then a constant concentration of insulin can be realized only if the insulin composition is not substantially diluted by the composition of the GLP-1 agonist. This imposes limits on the possibility of independent dosing of insulin and of the GLP-1 agonist.

One conceivable solution would be to provide the GLP-1 agonist in such a high concentration that the dosed addition of the GLP-1 agonist produces not significant dilution of the insulin composition (e.g., not more than 10%). Polypeptides such as insulins (e.g., insulin glargine, Lantus®) or GLP-1 agonists cannot be concentrated ad infinitum. First, the solubility of proteins is limited, and high concentrations of protein may alter the flow characteristics of the solution. The most important problem for the use of solutions with a high concentration of active compound is the dosing accuracy. At high concentrations it would be necessary to administer small volumes or to carry out dosing into a different solution. There are devices known for the precise dosing of small or very small volumes. However, such devices are expensive and, on the basis of their operation, are intended only for use by trained personnel, as in the laboratory, for example. Since, generally speaking, patients inject themselves with insulins and/or GLP-1 agonists, the use of such devices for administering insulins and/or GLP-1 agonists is ruled out The devices that are described, for example, in U.S. Pat. No. 4,689,042, U.S. Pat. No. 5,478,323, U.S. Pat. No. 5,253,785, and WO 01/02039, which allow the patients to inject themselves with active compound solutions, are unsuitable for the dosing of small and very small volumes.

The problems which arise with the injection of a combination of an insulin and a GLP-1 agonist are as follows
the proportion of the active compounds must be variable;
the pharmacokinetics of at least one of the active compounds (the insulin) is influenced by the concentration/dilution;
the pharmacokinetics of at least one other active compound (the GLP-1 agonist) is not, or not substantially, influenced by the concentration/dilution.

It was an object of the present invention, therefore, to provide a medicament which at least partly overcomes the above-described disadvantages of the prior art. A further intention is that there should as far as possible be only one administration per day.

It has been found, surprisingly, that the combination of an insulin with a GLP-1 agonist exhibits synergistic effects in the regulation of blood glucose in the postprandial and postabsorptive phases as compared with the use of insulin or the GLP-1 agonist alone:
Higher activity on the basis of the combination of the complementary activities on the fasting and postprandial glucose levels, which complement one another (examples 2 and 3). The combination exhibits a lowering in postprandial glucose concentration (i.e., improved glucose tolerance) like a GLP-1 agonist alone, and additionally exhibits the postabsorptive lowering of glucose like an insulin (example 9).
Reduction in the risk of hypoglycemia (examples 2-4).
Improved adaptation of the blood glucose concentration to normoglycemic levels (example 8).
Improved glucose tolerance and lowering of postabsorptive glucose concentrations (example 9).
The synergistic activities of the combination on the glucose concentration are observed in a GLP-1 agonist concentration range of one order of magnitude (factor 10). (Example 6 compared with examples 4 and 2). Only in the case of relatively small GLP-1 doses and/or relatively large proportions of insulin to GLP-1 are the activities of Insulin predominant.
Maintains the function of the β-cells (example 10).
Weight loss/reduction in weight gain.
All examples show that GLP-1 agonists and insulins exhibit no adverse interactions.
As a result of the activities on the fasting, postprandial, and postabsorptive blood glucose concentrations, it becomes possible to reduce the number of administrations of the combination to once daily.

The invention provides a medicament comprising at least one insulin and at least one GLP-1 agonist, the medicament being formulated and/or compounded in such a way that it comprises the insulin and the GLP-1 agonist each in a predetermined amount and can be administered in a dose adapted to the individual requirement of a patient.

The medicament of the invention is used in particular for treating patients with diabetes mellitus, more particularly patients with type 1 or type 2 diabetes.

The medicament of the invention allows the blood glucose concentration to be adapted more effectively to normoglycemic levels in the case of patients with diabetes, more particularly type 1 or type 2 diabetes.

The medicament is used preferably to adjust the fasting, postprandial and/or postabsorptive blood glucose concentration of patients with diabetes, more particularly patients with type 1 or type 2 diabetes. More preferably the medicament of the Invention is used to adjust the postprandial and/or postabsorptive blood glucose concentration of patients with diabetes, more particularly patients with type 1 or type 2 diabetes. Adjustment in this context means that normoglycemlc blood glucose concentrations are substantially achieved or at least an approximation thereto is obtained. By normoglycemic levels are meant more particularly blood glucose concentrations in the normal range (breadth of fluctuation 60-140 mg/dl, corresponding to 3.3 to 7.8 mmol/l). This range of fluctuation encompasses blood glucose concentrations under fasting conditions, postprandial conditions, and postabsorptive conditions.

Postprandial and postabsorptive are terms familiar to the person skilled in the field of diabetology. Postprandial is used herein to refer more particularly to the phase after a meal and/or after glucose loading in an experiment. This phase is characterized more particularly in a healthy individual by an increase and fall again in the concentration of glucose in the blood. Postabsorptive, or postabsorptive phase, is used herein to refer more particularly to the phase which follows the postprandial phase. The postprandial phase typically ends up to 4 h after the meal and/or glucose loading. The postabsorptive phase lasts typically for up to 8 to 16 h.

The medicament of the invention is also used preferably for improving glucose tolerance in the treatment of a patient with diabetes, more particularly with a type 1 or type 2 diabetes. Improving the glucose tolerance means that the medicament of the invention lowers the postprandial blood glucose concentration. Improving the glucose tolerance is also taken to mean that the medicament of the invention lowers the postabsorptive blood glucose concentration. Lowering means more particularly that the blood glucose concentration substantially reaches normoglycemic values or at least is approximated thereto.

The medicament of the invention is able to lower the risk of hypoglycemia, which may occur, for example, in the postabsorptive phase. The medicament of the invention is used preferably for preventing hypoglycemia in the treatment of a patient with diabetes, more particularly with a type 1 or type 2 diabetes, it being possible for the hypoglycemia to occur more particular in the postabsorptive phase.

The medicament of the invention may maintain the function of the pancreatic β-cells. The medicament of the invention is used preferably for preventing a loss of function of the pancreatic β-cells in a patient with diabetes, more particularly with a type 1 or type 2 diabetes. The loss of function of the p-cells may be caused more particularly by apoptosis.

Furthermore, the medicament of the invention may bring about a loss in weight and/or prevent a gain in weight in patients with diabetes, more particularly type I or II. In diabetes patients, especially those of type 2, weight gain and excessive weight are frequent problems. Accordingly, administering the medicament of the invention may support a therapy for the treatment of excessive weight.

It will be appreciated that the medicament of the invention can be used in order to treat more than one of the preferred indications described therein in a patient with diabetes, more particularly with a type 1 or 2 diabetes. Accordingly the present invention encompasses not only the individual preferred indications but also arbitrary combinations of the indications. The medicament of the invention can therefore be used to treat one or more of the herein-described indications in patients with diabetes, more particularly of patients with type 1 or type 2 diabetes, for the purpose, for example, of adjusting the fasting, postprandial and/or postabsorptive blood glucose concentration, for improving glucose tolerance, for preventing hypoglycemia, for preventing a loss of function of the pancreatic β-cells, for weight loss and/or for preventing weight gain, Preference is given to the adjustment of fasting, postprandial and/or postabsorptive blood glucose concentration, the improvement of glucose tolerance and/or the prevention of hypoglycemia.

The medicament of the invention can also be used for producing a medicinal product for treating one or more of the herein-described indications, as, for example, for adjusting the fasting, postprandial and/or postabsorptive blood glucose concentration, for improving glucose tolerance, for preventing hypoglycemia, for preventing a loss of function of the pancreatic β-cells, for weight loss and/or for preventing weight gain.

The at least one insulin and the at least one GLP-1 agonist may also be used for producing a medicinal product for treating one or more of the herein described indications, as for example for adjusting the fasting, postprandial and/or postabsorptive blood glucose concentration, for improving glucose tolerance, for preventing hypoglycemia, for preventing a loss of function of the pancreatic β-cells, for weight loss and/or for preventing weight gain.

The at least one GLP-1 agonist and the at least one insulin may be provided together in one pharmaceutical composition. In this case a first and a second composition and, optionally, at least one further pharmaceutical composition are provided, each comprising the insulin and the GLP1 agonist. Accordingly the invention provides a medicament comprising a first pharmaceutical composition and a second pharmaceutical composition, and, optionally, at least one further pharmaceutical composition, each comprising at least one insulin and at least one GLP-1 agonist, and containing the at least one insulin and/or the at least one GLP-1 agonist in different weight fractions relative to the total weight of the composition.

In the present specification "optionally, at least one further pharmaceutical composition" means that the medicament of the Invention, in addition to the first and second pharmaceutical compositions, may comprise at least one further pharmaceutical composition. Hence the medicament of the invention may comprise, for example, 3, 4, 5, 6, 7, 8, 9, 0.10 or more pharmaceutical compositions of the invention.

Preferred medicaments are those which comprise a first and a second pharmaceutical composition of the invention.

Likewise preferred are medicaments which comprise a first, a second, and a third pharmaceutical composition of the invention, Likewise preferred are medicaments which comprise a first, a second, a third, and a fourth pharmaceutical composition of the invention.

Likewise preferred are medicaments which comprise a first, a second, a third, a fourth, and a fifth pharmaceutical composition.

The weight fractions of the at least one insulin and of the at least one GLP-1 agonist may be selected in the first pharmaceutical composition, the second pharmaceutical composition, and, where used, the at least one further pharmaceutical composition in such a way that the pharmaceutical compositions contain different proportions of Insulin to GLP-1 agonist, based on the weight fraction.

In this case the first composition may contain the smallest proportion and the second composition the next-greater proportion. Where at least one further composition is present, it may contain the next-greater proportion. Where a further composition is present as well, it may contain the next-greater proportion in turn. The compositions may therefore contain proportions of insulin to GLP-1 agonist, based on the weight fraction, that increase from the first to the second and, where used, further compositions.

The weight fraction of one of the two active compounds, i.e., of the at least one insulin or of the at least one GLP-1 agonist, in the first pharmaceutical composition, the second pharmaceutical composition, and, where used, the at least one further pharmaceutical composition is preferably selected in each case such that the predetermined dose of this active compound can be administered by administering a defined volume of the first, second and/or at least one further composition. With particular preference this active compound is the at least one insulin.

The weight fraction of the other of the two active compounds, i.e., of the at least one insulin or of the at least one GLP-1 agonist, in the first pharmaceutical composition, the second pharmaceutical composition, and, where used, the at least one further pharmaceutical composition is preferably selected such that the proportions of insulin to GLP-1 agonist, based on the weight fraction, increase from the first to the second and, where used, further compositions. With particular preference this active compound is the at least one GLP-1 agonist.

Furthermore, the weight fraction of the other of the two active compounds in the pharmaceutical compositions is determined such that one of the pharmaceutical compositions can be selected in such a way that the dose of the first of the two active compounds that is to be administered and the dose of the second active compound that is to be administered are given in a defined volume. Hence a pharmaceutical composition is selected which contains the desired proportion.

Theoretically it would be possible to provide a pharmaceutical composition for each individual therapeutically desired proportion of the weight fractions of the at least one insulin to the at least one GLP-1 agonist, in order to obtain an optimum dosage, tailored to requirements, for both active compounds for every patient.

In the present invention, a particular number of pharmaceutical compositions is sufficient in order to cover the dosages needed in practice for the two active compounds. For each patient a defined dosage range is defined within a therapeutically rational interval for each of the two active compounds. The dose to be administered ought hereby to fluctuate essentially within this dosage range for a particular patient, without any overdosing or underdosing.

Surprisingly it has been found that the synergistic effects of the combination of at least one insulin and at least one GLP-1 agonist on the concentration of glucose in the blood plasma occur in a concentration range of the GLP-1 agonist of one order of magnitude (factor 10). Since it is primarily the amount of insulin that must be adapted and precisely dosed to the individual patient, the synergistic concentration range of the GLP-1 agonist allows a pharmaceutical composition of the invention that contains a defined proportion of at least one insulin to the at least one GLP-1 agonist to cover a therapeutic range of insulin doses simultaneously with the associated, synergistic amount of GLP-1 agonist. The proportion can be selected such that every desired insulin dose has its corresponding dose of the at least one GLP-1 agonist, which is situated within the desired range, e.g., the synergistic range. As set out earlier on above, the proportions of the first, second, and, where used, at least one further composition of the medicament may also be chosen such that the proportions increase from the first to the second and, where used, the at least one further composition. If the dose of the GLP-1 agonist at the desired insulin dose of a composition (e.g., of the first composition) is outside (generally above) the desired dosage range of the GLP-1 agonist, then the next composition (e.g., the second composition) or a further composition with a greater proportion of the at least one insulin to the at least one GLP-1 agonist, is selected for use, in which the amount of the GLP-1 agonist at the desired insulin dose lies within the desired range. The proportions of the first, second, and, where used, at least one further composition of the medicament may further be chosen such that the ranges of the insulin dosages which correspond to the desired dosages of the at least one GLP-1 agonist border one another and/or overlap one another. Preferably the ranges overlap. Overlapping means more particularly that it is possible to select at least two compositions which, at the desired dose of the at least one insulin, each contain an amount of the at least one GLP-1 agonist which lies within the desired dosage range.

For example, three compositions are sufficient to adjust the dose of the at least one insulin for an Individual patient to a level selected from the range from 15 to 80 units of insulin and at the same time to dose the GLP-1 agonist with an amount within the range from 10 to 20 µg (see example 11).

It is also possible to provide a medicament of the Invention in which the proportion is selected such that for each desired dosage of the GLP-1 agonist there is a corresponding dosage of the at least one insulin which lies within the desired range, e.g., the synergistic range. The proportions of the first, second, and, where used, at least one further composition of the medicament may also be chosen such that the ranges of the dosages of the GLP-1 agonist that correspond to the desired dosages of the at least one insulin border one another and/or overlap one another. Preferably the ranges overlap. Overlapping in this context means more particularly that it is possible to select at least two compositions which, at the desired dosage of the at least one GLP1 agonist, each contain an amount of the at least one insulin that lies within the desired dosage range.

Preferably the medicament of the invention contains not more than 10 pharmaceutical compositions as defined above, more preferably not more than 5, not more than 4, not more than 3 or 2 pharmaceutical compositions.

The compositions of the invention may contain the at least one insulin in identical or different weight fractions. For example, at least two of the compositions of the invention may contain the at least one insulin in a substantially identical weight fraction.

It is preferred for the first, second, and, where used, further compositions to contain the at least one insulin in a substantially identical weight fraction and the at least one GLP-1 agonist in different weight fractions.

The compositions of the invention may contain the at least one GLP-1 agonist in identical or different weight fractions. For example, at least two of the compositions of the invention may contain the at least one GLP-1 agonist in a substantially identical weight fraction.

It is also preferred for the first, second, and, where used, further compositions to contain the at least one GLP-1 agonist in a substantially identical weight fraction and the at least one insulin in different weight fractions.

Besides the first, second, and, where used, at least one further composition, the medicament of the invention may comprise at least one further pharmaceutical composition which contains either at least one insulin or at least one GLP-1 agonist. The medicament of the invention may also comprise at least one further pharmaceutical composition which contains at least one insulin and at least one GLP-1 agonist in a proportion of the weight fractions which is like the herein-described first, second or, where used, further pharmaceutical composition.

The invention further provides a medicament comprising a first pharmaceutical composition and a second pharmaceutical composition, the first pharmaceutical composition comprising at least one insulin and the second pharmaceutical composition comprising at least one GLP-1 agonist, the medicament being formulated and/or compounded for the independent administration of the first and second pharmaceutical compositions.

Example 12 shows how a combination of two or more active compounds can be formulated such that, when two or more compositions are combined, both active compounds can be administered in any desired amounts and in any desired proportions to one another. This takes account of the fact that at least one of the active compounds must not be diluted as a result of the combining (e.g., through mixing immediately prior to administration).

The present invention provides a medicament which comprises a first active compound and a second active compound, and, optionally, at least one further active compound, these active compounds being provided in a first, a second, and, optionally, at least one further composition. The first active compound is present in all of the compositions. The second active compound is present in the second formulation, and the at least one further active compound, where used, is present in the optionally at least one further composition. Hence the second and each further composition comprise the first active compound in combination with another active compound.

The present invention thus further provides a medicament which comprises a first pharmaceutical composition and a second pharmaceutical composition, and, optionally, at least one further pharmaceutical composition, the first pharmaceutical composition comprising at least one first active compound, and the second pharmaceutical composition comprising at least one first active compound and at least one second active compound, and the at least one further pharmaceutical composition comprising at least one first and at least one further active compound. The active compounds here may be any desired active compounds.

The first composition preferably comprises as active compound only the at least one first active compound.

The first, second, and, where used, at least one further compositions may comprise the first active compound in a substantially identical weight fraction or In different weight fractions relative to the total weight of the composition.

It is preferred for the first pharmaceutical composition, the second pharmaceutical composition, and, where used, the at least one further pharmaceutical composition to comprise the first active compound in substantially equal weight fractions relative to the total weight of the composition. By this means it is possible to ensure that any desired proportion of the first and second composition and, where appropriate, any desired proportion of the first and at least one further composition can be used, the dosing of the first active compound taking place via the total amount of the compositions administered. Via the proportion of the two compositions it is possible to increment steplessly the amount of the active compound which is present only in the second composition and, where appropriate, in the at least one further composition. In this way, therefore, it is readily possible to dose any desired amount and any desired proportion of the first to the second active compound and, where appropriate, of the first active compound to a further active compound, without altering the concentration of the first active compound.

The first active compound may be at least one insulin. The second active compound may be at least one GLP-1 agonist. Preference is given to a medicament which comprises a first pharmaceutical composition and a second pharmaceutical composition, and, optionally, At least one further pharmaceutical composition, the first pharmaceutical composition comprising at least one insulin, and the second pharmaceutical composition comprising at least one insulin and at least one GLP-1 agonist, and the at least one further pharmaceutical composition comprising at least one insulin and at least one further active compound.

The first composition preferably comprises as active compound only the at least one insulin.

The further active compound may be any desired active compound. More particularly the further active compound is an active compound which is used for treating patients with diabetes mellitus (type 1 and/or type 2), including active compounds for treating concomitant disorders of diabetes as well.

The first, second, and, where used, at least one further composition may comprise the insulin in a substantially equal weight fraction or in different weight fractions relative to the total weight of the composition.

It is preferred for the first pharmaceutical composition, the second pharmaceutical composition, and, where used, the at least one further pharmaceutical composition to comprise the Insulin in substantially equal weight fractions relative to the total weight of the composition. By this means it is possible to ensure that any desired proportion of the first and second composition and, where appropriate, any desired proportion of the first and at least one further compositions can be used, the dosing of the insulin taking place via the total amount of the compositions administered. Via the proportion of the two compositions it is possible to increment steplessly the amount of the active compound which Is present only in the second composition and, where appropriate, in the at least one further composition. In this way, therefore, it is readily possible to dose any desired amount and any desired proportion of insulin to GLP-1 agonist and, where appropriate, of insulin to a further active compound, without altering the concentration of the at least one insulin.

In the present invention, "substantially equal weight fractions" of an active compound in two compositions means that one of the two compositions contains the active compound in a weight fraction which is, for example, not more than 10%, not more than 5%, not more than 1% or not more than 0.1% higher than its weight fraction in the other composition.

The first active compound may also be at least one GLP-1 agonist. The second active compound may be at least one insulin. Preference is given to a medicament which comprises a first pharmaceutical composition and a second pharmaceutical composition, and, optionally, at least one further pharmaceutical composition, the first pharmaceutical composition comprising at least one GLP-1 agonist, and the second pharmaceutical composition comprising at least one GLP-1 agonist and at least one insulin, and the at least one further pharmaceutical composition comprising at least one GLP-1 agonist and at least one further active compound.

The first composition preferably comprises as active compound only the at least one GLP1 agonist.

The first, second, and, where used, at least one further compositions may comprise the GLP-1 agonist in a substantially equal weight fraction or in different weight fractions relative to the total weight of the composition. It is preferred for the first pharmaceutical composition, the second pharmaceutical composition and, where used, the at least one further pharmaceutical composition to comprise the at least one GLP-1 agonist in substantially equal weight fractions relative to the total weight of the composition.

Accordingly the present invention provides a medicament which exhibits a number of advantages over compositions of the prior art comprising separate compositions each containing one active compound, more particularly an insulin or a GLP-1 agonist, said advantages including the following:

the ratio of the first active compound to the second active compound and, where appropriate, of the first active compound to the at least one further active compound can be chosen freely by the user.

Since the first active compound is present in all of the compositions, more particularly in equal weight fractions, this active compound is not diluted when the first composition is mixed with the second and, where appropriate, further compositions. This is important for active compounds such as insulin, for example, where the pharmacokinetics is influenced by the concentration/dilution.

The injection volume is reduced (see example 12). Hence there is a reduction in the dilution of the second active compound (e.g., a GLP-1 agonist) and, where appropriate, of a further active compound.

The invention additionally provides a kit comprising a medicament of the invention. The kit of the invention may be intended for use by medical staff or by persons without specialist medical training, more particularly by the patients themselves or helpers such as relatives. In the kit of the invention, the individual pharmaceutical compositions comprising the medicament of the invention are assembled in separate packs, and so the patient is able to select the composition appropriate to the current requirement and to administer an amount in line with that requirement. The kit of the invention comprises, for example, the medicament of the invention in the form of a set of syringes, glass ampoules and/or pens which comprise a composition of the invention.

There are a variety of ways in which the medicament of the invention can be administered. The medicament may be administered parenterally. The medicament may be injected, with the possible use of injection systems with or without needles. Furthermore, the medicament may be administered by inhalation. In this case it is possible for liquid compositions to be inhaled, or the compositions can be inhaled in the form of powder. Furthermore, the medicament of the invention may be administered as a spray, more particularly as a nasal spray. In addition the medicament of the invention may be administered by a transdermal system. The skilled worker is aware of these methods of administration and is able to formulate the medicament of the invention in such a way that it can be effectively administered by one of these methods of administration. The compositions of the medicament of the invention are preferably liquid. It is preferred, furthermore, for the medicament of the invention to be administered parenterally, more particularly by injection.

The present invention further provides a device for administering the medicament of the invention. This device comprises the pharmaceutical compositions which are encompassed by the medicament of the invention, in separate containers, and allows the pharmaceutical compositions to be dosed independently of one another. The device of the invention may be a device for parenteral administration. The device of the invention may be a device for injection with or without needles. Furthermore, the device may be a device for inhalation, in which case liquid compositions are inhaled, or the compositions can be inhaled in the form of powder. Moreover, the device may be a device for administering a spray, more particularly a nasal spray. In addition, the device may be a transdermal administration system. It is preferred for the device of the invention to be a device for parenteral administration, more particularly an injection device.

"Compounding" is a term which is known to the skilled worker and which in pharmacology identifies the finishing treatment, such as portioning and packing, for example, of medicaments for use by the end user. In the present specification, "compounded" or "compounding" means more particularly that the pharmaceutical compositions of the invention are packaged in a suitable way in a therapeutically effective amount to allow the herein-described selection of at least one of the compositions of the medicament of the invention for the desired dosing of the at least one insulin and of the at least one GLP-1 agonist. Intended more particularly is a parenteral administration, preferably an injection, more preferably subcutaneous injection. Suitable packaging is, for example, a syringe or a glass vessel with a suitable closure, from which, as required, individual therapeutically active doses can be taken. Likewise suitable are injection pens for the administration of insulin, comprising a container (e.g., a cartridge) which contains a pharmaceutical composition of the invention.

"Formulating" or "formulation" is a term which is known to the skilled worker and which, in the field of pharmacology, refers to the production of medicaments and medicament compositions, and their preparation with excipients. In the present specification "formulating" or "formulation" means more particularly that the composition of the invention is provided in a suitable form which allows administration of a therapeutically effective amount of the active compounds. More particularly a formulation is intended for parenteral administration, preferably for injection, more preferably for subcutaneous injection.

In the present invention the term "GLP-1 agonist" includes GLP-1, analogs and derivatives thereof, exendin-3 and analogs and derivatives thereof, and exendin-4 and analogs and derivatives thereof. The compositions of the invention comprise one or more selected independently of one another from the group consisting of glucagon-like peptide-1 (GLP-1), analogs and derivatives of GLP-1, exendin-3, analogs and derivatives of exendin-3, exendin-4, analogs and derivatives of exendin-4, and pharmacologically tolerable salts thereof. Also included are substances which exhibit the biological activity of GLP-1.

GLP-1 analogs and derivatives are described in WO 98/08871, for example; exendin-3, analogs and derivatives of exendin-3, and exendin-4 and analogs and derivatives of exendin-4 can be found in WO 01/04156, WO 98/30231, U.S. Pat. No. 5,424,286, in EP application 99 610043A, in WO 2004/005342 and WO 04/035623. These documents are included herein by reference. The exendin-3 and exendin-4 described in these documents, and the analogs and derivatives thereof that are described there, can be used in the compositions of the present invention as GLP-1 agonists. It is also possible to use any desired combinations of the exendin-3 and exendin-4 described in these documents, and the analogs and derivatives described therein, as GLP-1 agonists. The at least one GLP-1 agonist is preferably independently selected from the group consisting of exendin-4, analogs and derivatives of exendin-4, and pharmacologically tolerable salts thereof.

A further preferred GLP-1 agonist is an analog of exendin-4 selected from a group consisting of:
H-desPro$^{36}$-exendin-4-Lys$_6$-NH$_2$,
H-des(Pro$^{36,37}$)-exendin-4-Lys$_4$-NH$_2$,
H-des(Pro$^{36,37}$)-exendin-4-Lys$_5$-NH$_2$, and pharmacologically tolerable salts thereof.

A further preferred GLP-1 agonist is an analog of exendin-4 selected from a group consisting of:
desPro$^{36}$ [Asp$^{28}$]exendin-4 (1-39),
desPro$^{36}$ [IsoAsp$^{28}$]exendin-4 (1-39),
desPro$^{36}$ [Met(O)$^{14}$, Asp$^{28}$]exendin-4 (1-39),
desPro$^{36}$ [Met(O)$^{14}$, IsoAsp$^{26}$]exendin-4 (1-39),
desPro$^{36}$ [Trp(O$_2$)$^{25}$, Asp$^{28}$]exendin-2 (1-39),
desPro$^{36}$ [Trp(O$_2$)$^{26}$, IsoAsp$^{28}$]exendin-2 (1-39),
desPro$^{36}$ [Met(O)$^{14}$Trp(O$_2$)$^{25}$, Asp$^{28}$]exendin-4 (1-39),
desPro$^{36}$ [Met(O)$^{14}$Trp(O$_2$)$^{25}$, IsoAsp$^{28}$]exendin-4 (1-39),
and pharmacologically tolerable salts thereof.

A further preferred GLP-1 agonist is an analog of exendin-4 selected from a group as described in the paragraph above in which the peptide-Lys$_6$-NH$_2$ has been attached at the C-terminii of the analogs of exendin-4.

A further preferred GLP-1 agonist is an analog of exendin-4 selected from a group consisting of:
H-(Lys)$_6$-des Pro$^{36}$ [Asp$^{28}$]exendin-4(1-39)-Lys$_6$-NH$_2$
des Asp$^{28}$Pro$^{36}$, Pro$^{37}$, Pro$_{38}$ exendin-4(1-39)-NH$_2$,
H-(Lys)$_6$-des Pro$^{36}$, Pro$^{37}$, Pro$^{38}$ [Asp$^{26}$]exendin-4(1-39)-NH$_2$,
H-Asn-(Glu)$_5$ des Pro$^{36}$, Pro$^{37}$, Pro$^{38}$ [Asp$^{28}$]exendin-4(1-39)-NH$_2$,
des Pro$^{36}$, Pro$^{37}$, Pro$^{38}$ [Asp$^{28}$]exendin-4(1-39)-(Lys)$_6$-NH$_2$,
H-(Lys)$_6$-des Pro$^{36}$, Pro$^{37}$, Pro$^{38}$ [Asp$^{28}$]exendin-4(1-39)-(Lys)$_6$-NH$_2$,
H-Asn-(Glu)$_5$-des Pro$^{36}$, Pro$^{37}$, Pro$^{38}$ [Asp$^{28}$]exendin-4(1-39)-(Lys)$_6$-NH$_2$,
H-(Lys)$_6$-des Pro$^{36}$[Trp(O$_2$)$^{25}$, Asp$^{28}$]exendin-4(1-39)-Lys$_6$-NH$_2$,
H-des Asp$^{28}$ Pro$^{36}$, Pro$^{37}$, Pro$^{38}$ [Trp(O$_2$)$^{26}$]exendin-4(1-39)-NH$_2$,
H-(Lys)$_6$-des Pro$^{36}$, Pro$^{37}$, Pro$^{38}$ [TrP(O$_2$)$_{25}$, Asp$^{28}$]exendin-4(1-39)-NH$_2$,
H-Asn-(Glu)$_5$-des Pro$^{36}$, Pro$^{37}$, Pro$^{38}$ [Trp(O$_2$)$^{25}$, Asp$^{28}$]exendin-4(1-39)-NH$_2$,
des Pro$^{36}$, Pro$^{37}$, Pro$^{38}$ [Trp(O$_2$)$^{25}$, Asp$^{28}$]exendin-4(1-39)-(Lys)$_6$-NH$_2$,
H-(Lys)$_6$-des Pro$^{36}$, Pro$^{37}$, Pro$^{38}$ [Trp(O$_2$)$^{25}$, Asp$^{26}$]exendin-4(1-39)-(Lys)$_6$-NH$_2$, H-Asn-(Glu)$_5$-des Pro$^{36}$, Pro$^{37}$, Pro$^{38}$ [Trp(O$_2$)$^{25}$, Asp$^{28}$] exendin-4(1-39)-(Lys)$_e$-NH$_2$,
H-(Lys)$_6$-des Pro$^{36}$ [Met(O)$^{14}$, Asp$^{28}$]exendin-4(1-39)-Lys$_6$-NH$_2$,
des Met(O)$^{14}$ Asp$^{28}$ Pro$^{36}$, Pro$^{37}$, Pro$^{38}$ exendin-4(1-39)-NH$_2$,
H-(Lys)$_6$-des Pro$^{36}$, Pro$^{37}$, Pro$^{38}$ [Met(O)$^{14}$, Asp$^{28}$]exendin-4(1-39)-NH$_2$,
H-Asn-(Glu)$_5$-des Pro$^{36}$, Pro$^{37}$, Pro$^{38}$ [Met(O)$^{14}$, Asp$^{28}$] exendin-4(1-39)-NH$_2$,
des Pro$^{36}$, Pro$^{37}$, Pro$^{38}$ [Met(O)$^{14}$, Asp$^{28}$]exendin-4(1-39)-(Lys)$_6$-NH$_2$,
H-(Lys)$_6$-des Pro$^{36}$, Pro$^{37}$, Pro$^{38}$ [Met(O)$^{14}$, Asp$^{28}$]exendin-4(1-39)-Lys$_6$-NH$_2$,
H-Asn-(Glu)$_5$ des Pro$^{36}$, Pro$^{37}$, Pro$^{38}$ [Met(O)$^{14}$, Asp$^{28}$] exendin-4(1-39)-(Lys)$_6$-NH$_2$,
H-(Lys)$_6$-des Pro$^{36}$ [Met(O)$^{14}$, Trp(O$_2$)$^{25}$, Asp$^{28}$]exendin-4(1-39)-Lys$_6$-NH$_2$,
des Asp$^{28}$ Pro$^{36}$, Pro$^{37}$, Pro$^{38}$ [Met(O)$^{14}$, Trp(O$_2$)$^{25}$]exendin-4(1-39)-NH$_2$,
H-(Lys)$_6$-des Pro$^{36}$, Pro$^{37}$, Pro$^{38}$ [Met(O)$^{14}$, Trp(O$_2$)$^{25}$, Asp$^{28}$]exendin-4(1-39)-NH$_2$,
H-Asn-(Glu)$_5$-des Pro$^{36}$, Pro$^{37}$, Pro$^{38}$ [Met(O)$^{14}$, Asp$^{28}$] exendin-4(1-39)-NH$_2$,
des Pro$^{36}$, Pro$^{37}$, Pro$^{38}$[Met(O)$^{14}$, Trp(O$_2$)$^{25}$, Asp$^{28}$]exendin-4(1-39)-(Lys)$_6$-NH$_2$,
H-(Lys)$_6$-des Pro$^{36}$, Pro$^{37}$, Pro$^{38}$ [Met(O)$^{14}$, Trp(O$_2$)$^{25}$, Asp$^{28}$]exendin-4(1-39)-(Lys)$_6$-NH$_2$,
H-Asn-(Glu)$_5$-des Pro$^{36}$, Pro$^{37}$, Pro$^{38}$ [Met(O), Trp(O$_2$)$^{25}$, Asp$^{28}$]exendin-4(1-39)-(Lys)$_6$-NH$_2$, and pharmacologically tolerable salts thereof.

A further preferred GLP-1 agonist is selected from a group consisting of Arg$^{34}$, Lys$^{26}$(N$^\varepsilon$(γ-glutamyl(N$^\alpha$-hexadecanoyl)))GLP-1(7-37) [liraglutide] and a pharmacologically tolerable salt thereof.

A further preferred GLP-1 agonist is AVE0010. AVE0010 has the sequence of Pro$^{36}$exendin-4(1-39)-Lys$_6$-NH$_2$. This substance is published as SEQ ID No: 93 in WO 01/04156. Preference is also given to pharmacologically tolerable salts of AVE0010.

The term "at least one GLP-1 agonist" includes combinations of the herein-described GLP-1 agonists which are used in the compositions of the invention, examples being any desired combinations of two or more GLP-1 agonists selected from the GLP-1 agonists described herein.

The at least one GLP-1 agonist is further preferably independently selected from exendin-4, Pro$^{36}$exendin-4(1-39)-Lys$_6$-NH$_2$, and Arg$^{34}$, Lys$^{26}$(N$^\varepsilon$(γ-glutamyl(N$^\alpha$-hexadecanoyl)))GLP-1(7-37) [liraglutide], and pharmacologically tolerable salts thereof.

The compositions of the invention contain the GLP-1 agonist in an amount of 10 μg/ml to 20 mg/ml, preferably 25 μg/ml to 15 mg/mL. For the acidic to neutrally dissolved GLP-1 agonists the figures are preferably 20 μg/ml to 300 μg/ml, and for the neutral to basic agonists they are preferably 500 μg/ml to 10 mg/mL. For exendin-4 analogs, 20 μg/ml to 150 μg/ml are preferred.

In the present specification the term "insulin" encompasses not only unmodified insulins but also insulin analogs, insulin derivatives, and insulin metabolites. The compositions of the invention comprise one or more independently selected from the group consisting of insulins (e.g., unmodified insulins), insulin analogs, insulin derivatives, and insulin metabolites, and any desired combinations thereof.

The at least one insulin may independently be selected from the group consisting of bovine insulins, analogs, derivatives, and metabolites thereof, porcine insulins, analogs, derivatives, and metabolites thereof, and human insulins, analogs, derivatives, and metabolites thereof. Preferably the at least one insulin is independently selected from human insulins, analogs, derivatives, and metabolites thereof.

Furthermore, an insulin of the invention may be selected independently from unmodified insulins, more particularly from bovine insulins, porcine insulins, and human insulins.

The at least one insulin may independently be selected from the group consisting of bovine insulins, porcine insulins, and human insulins. More preferably the at least one insulin is independently selected from human insulins. An insulin of the invention may be selected from unmodified insulins, more particularly from bovine insulins, porcine insulins, and human insulins.

Insulin derivatives of the invention are derivatives of a naturally occurring insulin and/or an insulin analog, which are obtained by chemical modification. The chemical modification may consist, for example, in the addition of one or more defined chemical groups onto one or more amino acids"

Insulin analogs which are described in EP 0 214 826, EP 0 375 437, EP 0 678 522, EP 0 885 961, EP 0 419 504, WO 92/00321, German patent applications 10 2008 003 568.8 and 10 2008 003 566.1, and EP-A 0 368 187 may be part of the compositions of the invention. The documents EP 0 214 826, EP 0 375 437, EP 0 678 522, EP 0 419 504, WO 92/00321, and EP-A 0 368 187 are included herein by reference.

One preferred insulin analog of the invention may be selected from the group consisting of Gly(A21)-Arg(B31)-Arg(B32) human insulin (insulin glargine, Lantus); Arg (A0)-His(A8)-Glu(A15)-Asp(A18)-Gly(A21)-Arg(B31)-Arg(B32) human insulin amide, Lys(B3)-Glu(B29) human insulin; Lys$^{B28}$Pro$^{B29}$ human Insulin (insulin lyspro), B28 Asp human insulin (insulin aspart), human insulin in which proline in position B28 has been substituted by Asp, Lys, Leu, Val or Ala and where Lys in position B29 may be substituted by Pro; AlaB26 human insulin; des(B28-B30) human insulin; des(B27) human insulin or B29Lys(ε-tetradecanoyl),des(B30) human insulin (insulin detemir).

A preferred insulin derivative of the invention may be selected from the group consisting of B29-N-myristoyl-des (B30) human insulin, B29-N-palmitoyl-des(B30) human insulin, B29-N-myristoyl human insulin, B29-N-palmitoyl human insulin, B28-N-myristoyl Lys$^{B28}$Pro$^{B29}$ human insulin, B28-N-palmitoyl-Lys$^{B28}$Pro$^{B29}$ human insulin, B30-N-myristoyl-Thr$^{B29}$Lys$^{B30}$ human Insulin, B30-N-palmitoyl-Thr$^{B29}$Lys$^{B30}$ human insulin, B29-N—(N-palmitoy!-γ-glutamyl)-des(B30) human insulin, B29-N—(N-lithochoiyl-γ-glutamyl)-des(B30) human insulin, B29-N-(ω-carboxyheptadecanoyl)-des(B30) human insulin, and B29-N-(ωw-carboxyheptadecanoyl) human insulin.

A more highly preferred insulin derivative of the invention is selected from the group consisting of Gly(A21)-Arg (B31)-Arg(B32) human insulin, Lys$^{B28}$Pro$^{B29}$ human insulin (insulin lyspro), B28 Asp human Insulin (insulin aspart), B29Lys(ε tetradecanoyl), desB30 human insulin (insulin detemir).

The term "at least one insulin" includes combinations of the herein-described insulins, analogs, derivatives, and metabolites thereof which are used in the compositions of the invention, e.g., any desired combinations of two or more selected from the herein-described insulins, analogs, derivatives, and metabolites.

The compositions of the invention contain 60-6000 nmol/ml, preferably 240-3000 nmol/ml, of an insulin as defined herein. Depending on the insulin used, a concentration of 240-3000 nmol/ml corresponds approximately to a concentration of 1.4-35 mg/ml or 40-500 units/ml.

In the 2 to 10, preferably 3 to 5, pens cover all system, the compositions are in the range from 20 µg/ml of GLP-1 agonist and 100 U/ml of insulin to 300 µg/ml of GLP-1 agonist and 500 U/ml of insulin. Preference is given to the following concentration ranges: 25 µg/ml and 100 U/ml, 33 µg/ml and 100 U/ml, 40 µg/ml and 100 U/ml, 66 µg/ml and 100 U/ml, and 75 µg/ml and 100 U/ml.

The desired dosage range of the insulin is in particular a dosage with a synergistic effect. Here the values are 5 to 100 U, preferably 15 to 80 U. For the GLP-1 agonist the values for the dosage range are 5 µg to 2 mg, preferably 10 µg to 1.8 mg, more preferably 10 µg to 30 µg.

The preferred presentation form of the pharmaceutical compositions of the present invention is that of liquid compositions suitable in particular for parenteral administration, more preferably for injection, most preferably for subcutaneous injection. In particular the pharmaceutical composition of the present invention is suitable for injection once daily.

The pharmaceutical composition of the present invention may have an acidic or physiological pH. An acidic pH range is situated preferably in the range of pH 1-6.8, more preferably pH 3.5-6.8, even more preferably pH 3.5-4.5, most preferably at a pH about 4.0-4.5. A physiological pH is situated preferably in the range of pH 4.0-8.5, more preferably pH 5.0 to 8.5, even more preferably pH 6.0 to 8.5.

The composition of the invention may comprise a suitable preservative. Examples of suitable preservatives include phenol, m cresol, benzyl alcohol and/or p hydroxybenzoic esters.

The composition of the invention may further comprise a suitable buffer. Buffer substances which can be used, particularly for setting a pH level between about 4.0 and 8.5, include, for example, sodium acetate, sodium citrate, sodium phosphate, etc. Otherwise, physiologically unobjectionable dilute acids (typically HCl) or alkalis (typically NaOH) are suitable for setting the pH level. Preferred concentrations of the buffers and also of corresponding salts are in the range of 5-250 mM, more preferably in the range of 10-100 mM.

The composition of the invention may comprise zinc ions. The concentration of the zinc ions is preferably in the range from 0 µg/ml to 500 µg/ml, more preferably from 5 µg to 200 µg of zinc/ml.

The composition of the Invention may further comprise suitable isotonicity agents. Suitable examples include glycerol, dextrose, lactose, sorbitol, mannitol, glucose, NaCl, calcium compounds or magnesium compounds such as $CaCl_2$, etc. Glycerol, dextrose, lactose, sorbitol, mannitol, and glucose are typically in the range of 100-250 mM, NaCl in a concentration of up to 150 mM.

The composition of the invention may further comprise a surfactant. A surfactant may greatly increase the stability of acidic insulin compositions. Using surfactant it is even possible to prepare compositions which guarantee the superior stability with respect to hydrophobic aggregation nuclei over a number of months with temperature exposure.

The surfactant is preferably selected from the group consisting of partial and fatty acid esters and ethers of polyhydric alcohols such as of glycerol and of sorbitol, and polyols, the partial and fatty acid esters and ethers of glycerol and of sorbitol being selected from a group containing Span®, Tween®, Myrj®, Brij®, and Cremophor®; and the polyols being selected from the group of polypropylene glycols, polyethylene glycols, poloxamers, polysorbates, Pluronics, and Tetronics. Preferred concentrations of the surfactants are in the range of 5-200 µg/ml, preferably of 5-120 µg/ml and more preferably of 20-75 µg/ml.

The composition of the invention may further comprise other additives such as, for example, salts, which retard the release of at least one insulin.

One particularly preferred subject of the invention is a medicament as described herein comprising at least one insulin independently selected from $Lys^{B28}Pro^{B29}$ human insulin (insulin lyspro), B28 Asp human Insulin (insulin aspart), B29Lys(ε-tetradecanoyl),desB30 human insulin (insulin detemir), and insulin glargine (Gly(A21)-Arg(B31)-Arg(B32) human insulin), and comprising AVE0010 and/or a pharmacologically tolerable salt thereof. A further particularly preferred subject is a medicament as described herein comprising insulin glargine (Gly(A21)-Arg(B31)-Arg(B32) human insulin) and AVE0010 (des $Pro^{36}$exendin-4(1-39)-$Lys_6$-$NH_2$) and/or a pharmacologically tolerable salt thereof. The compositions of these particularly preferred medicaments preferably have an acidic pH of 1-6.8, more preferably pH 3.5-6.8, even more preferably pH 3.5-5.0, most preferably a pH of about 4.0 to 4.5. In addition, the compositions of these particularly preferred medicaments may comprise a surfactant as described herein.

A further subject of the invention is a combination of insulin glargine (Gly(A21)-Arg(B31)-Arg(B32) human insulin) and AVE0010 (des $Pro^{36}$exendin-4(1-39)-$Lys_6$-$NH_2$) and/or a pharmacologically tolerable salt thereof.

The invention further provides a method of treating a patient with a kit or medicament of the invention as described herein.

The method of the invention for treating a patient comprises the administration of a medicament of the invention comprising at least one insulin and at least one GLP-1 agonist, the medicament being formulated and/or compounded such that it contains the insulin and the GLP-1 agonist each in a predetermined amount and can be administered in a dose adapted to the Individual requirement of a patient.

More particularly the method comprises the administration of a medicament comprising a first pharmaceutical composition and a second pharmaceutical composition, and, optionally, at least one further pharmaceutical composition, each comprising at least one insulin and at least one GLP-1 agonist, and comprising the at least one insulin and/or the at least one GLP-1 agonist in different weight fractions relative to the total weight of the composition, said method comprising:

(a) selecting a dose of the at least one insulin that is to be administered,
(b) selecting a dose of the at least one GLP-1 agonist that is to be administered,
(c) selecting a composition, from the first, second, and, where used, at least one further compositions of the medicament that comprises the doses from (a) and (b) in a concentration such that the doses from (a) and (b) are present in the same volume, and
(d) determining and administering an amount which corresponds to the doses from (a) and (b).

The dose according to step (a) and/or step (b) is determined according to the individual requirement of the patients.

Step (c) of the treatment method of the invention can be carried out on the basis of a table. This table may be part of the medicament of the invention. Example 11 contains an example of a table of the invention.

The method of treating a patient may more particularly comprise the administration a medicament, the medicament comprising a first pharmaceutical composition and a second pharmaceutical composition, and, optionally, at least one further pharmaceutical composition, the first pharmaceutical composition comprising at least one first active compound, and the second pharmaceutical composition comprising at least one first active compound and at least one second active compound, the at least one further pharmaceutical composition comprising at least one first active compound and at least one further active compound, and the method comprising the following steps:
  (i) selecting a dose of the at least one first active compound that is to be administered, and determining the total amount of the first, second, and, where used, at least one further composition, so that the selected dose of the at least one first active compound is present in the total amount,
  (ii) selecting a dose of the at least one second active compound that is to be administered and determining the amount of the second composition so that the selected dose of the at least one second active compound is present in the amount of the second composition,
  (iii) where appropriate, selecting a dose of the at least one further active compound that is to be administered, and determining the amount of the at least one further composition so that the selected dose of the at least one further active compound is present in the amount of the at least one further composition,
  (iv) administering an amount of the first composition to the patient, the administered amount corresponding to the total amount as per step (i) minus the amount of the second composition as per step (ii), and, where appropriate, minus the amount of the at least one further composition as per step (iii), and
  (v) administering the amount of the second composition that was determined in step (ii), and, where appropriate, the amount of the at least one further composition that was determined in step (iii), to the patient The first active compound may be an insulin, and the second active compound may be a GLP-1 agonist. Hence the method of treating a patient may comprise more particularly the administration of a medicament, the medicament comprising a first pharmaceutical composition and a second pharmaceutical composition, and, optionally, at least one further pharmaceutical composition, the first pharmaceutical composition comprising at least one Insulin, and the second pharmaceutical composition comprising at least one insulin and at least one GLP-1 agonist, and the at least one further pharmaceutical composition comprising at least one insulin and at least one further active compound, and the method comprising the steps of:
  (i) selecting a dose of the at least one insulin that is to be administered, and determining the total amount of the first, second, and, where used, at least one further composition, so that the selected dose of the at least one insulin is present in the total amount,
  (ii) selecting a dose of the at least one GLP-1 agonist that is to be administered and determining the amount of the second composition so that the selected dose of the at least one GLP-1 agonist is present in the amount of the second composition,
  (ill) where appropriate, selecting a dose of the at least one further active compound that is to be administered, and determining the amount of the at least one further composition so that the selected dose of the at least one further active compound is present in the amount of the at least one further composition,
  (iv) administering an amount of the first composition to the patient, the administered amount corresponding to the total amount as per step (i) minus the amount of the second composition as per step (ii), and, where appropriate, minus the amount of the at least one further composition as per step (iii), and
  (v) administering the amount of the second composition that was determined in step (ii), and, where appropriate, the amount of the at least one further composition that was determined in step (iii), to the patient.

The first active compound may be a GLP-1 agonist, and the second active compound may be an insulin. Hence the method of treating a patient may comprise more particularly the administration of a medicament, the medicament comprising a first pharmaceutical composition and a second pharmaceutical composition, and, optionally, at least one further pharmaceutical composition, the first pharmaceutical composition comprising at least one GLP-1 agonist, and the second pharmaceutical composition comprising at least one GLP-1 agonist and at least one insulin, and the at least one further pharmaceutical composition comprising at least one GLP-1 agonist and at least one further active compound, and the method comprising the steps of:
  (l) selecting a dose of the at least one GLP-1 agonist that is to be administered, and determining the total amount of the first, second, and, where used, at least one further composition, so that the selected dose of the at least one GLP-1 agonist is present in the total amount,
  (ii) selecting a dose of the at least one insulin that is to be administered and determining the amount of the second composition so that the selected dose of the at least one insulin is present in the amount of the second composition,
  (iii) where appropriate, selecting a dose of the at least one further active compound that is to be administered, and determining the amount of the at least one further composition so that the selected dose of the at least one further active compound is present in the amount of the at least one further composition,
  (iv) administering an amount of the first composition to the patient, the administered amount corresponding to the total amount as per step (i) minus the amount of the second composition as per step (ii), and, where appropriate, minus the amount of the at least one further composition as per step (iii), and
  (v) administering the amount of the second composition that was determined in step (ii), and, where appropriate, the amount of the at least one further composition that was determined in step (iii), to the patient Steps (i), (ii) and/or (iii) may be carried out on the basis of at least one table, which may be part of the medicament For each of steps (i), (ii), and (iii) independently of one another a table may be provided.

The treatment method of the invention may be used more particularly for treating patients with diabetes, more particularly with diabetes type 1 or II. Preferably the method is used to adjust the fasting, postprandial and/or postabsorptive blood glucose concentration, for improving glucose tolerance, for preventing hypoglycemia, for 2.0 preventing loss of function of the pancreatic cells, for weight loss and/or for preventing weight gain.

The invention further provides a method of preparing a medicament of the invention, comprising formulating and/or compounding, such that it contains the insulin and the GLP-1 agonist each in a predetermined amount and can be administered in a dose adapted to the individual requirement of a patient in the preparation method the medicament is preferably formulated and compounded such that one of the herein-described medicaments of the invention can be obtained, as for example a medicament of the invention comprising a first pharmaceutical composition and a second pharmaceutical composition, and, optionally, at least one further pharmaceutical composition, each comprising at least one insulin and at least one GLP-1 agonist, and comprising the at least one insulin and/or the at least one GLP-1 agonist in different weight fractions relative to the total weight of the composition.

The invention is illustrated by the following figures and the following examples, which do not restrict the invention in any way whatsoever.

DETAILED DESCRIPTION OF THE DRAWINGS

Figure 2:
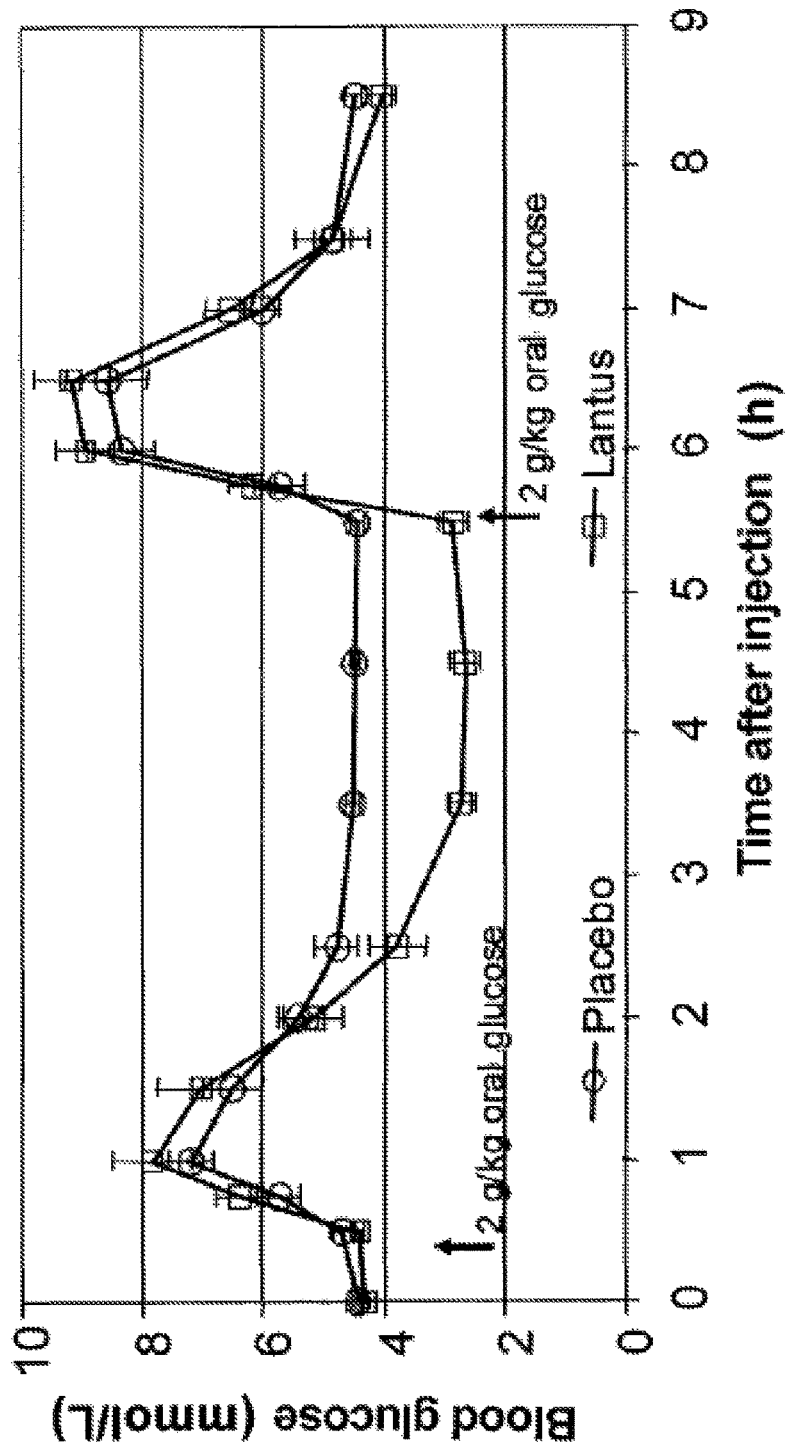
Figure 3:
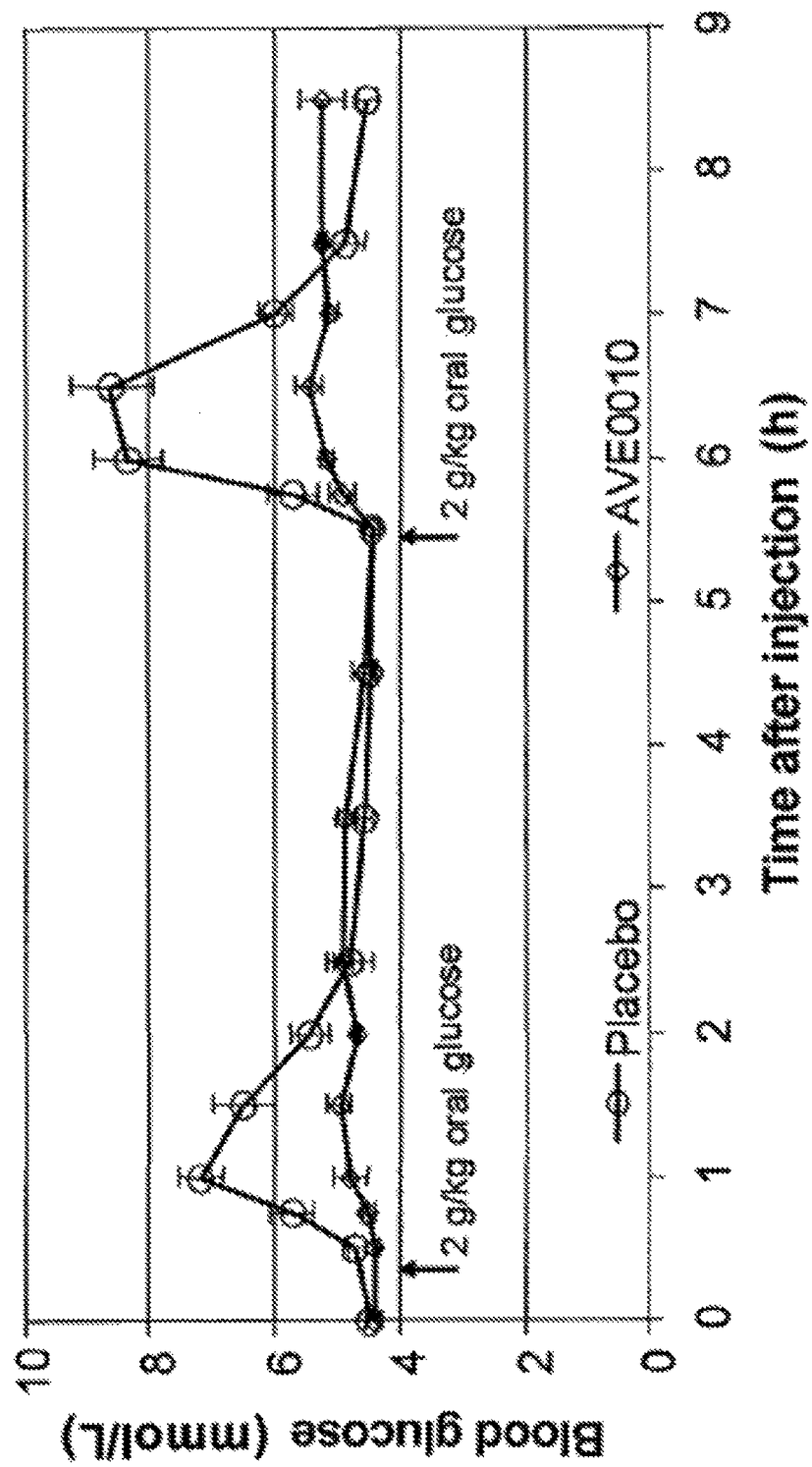
Figure 4:
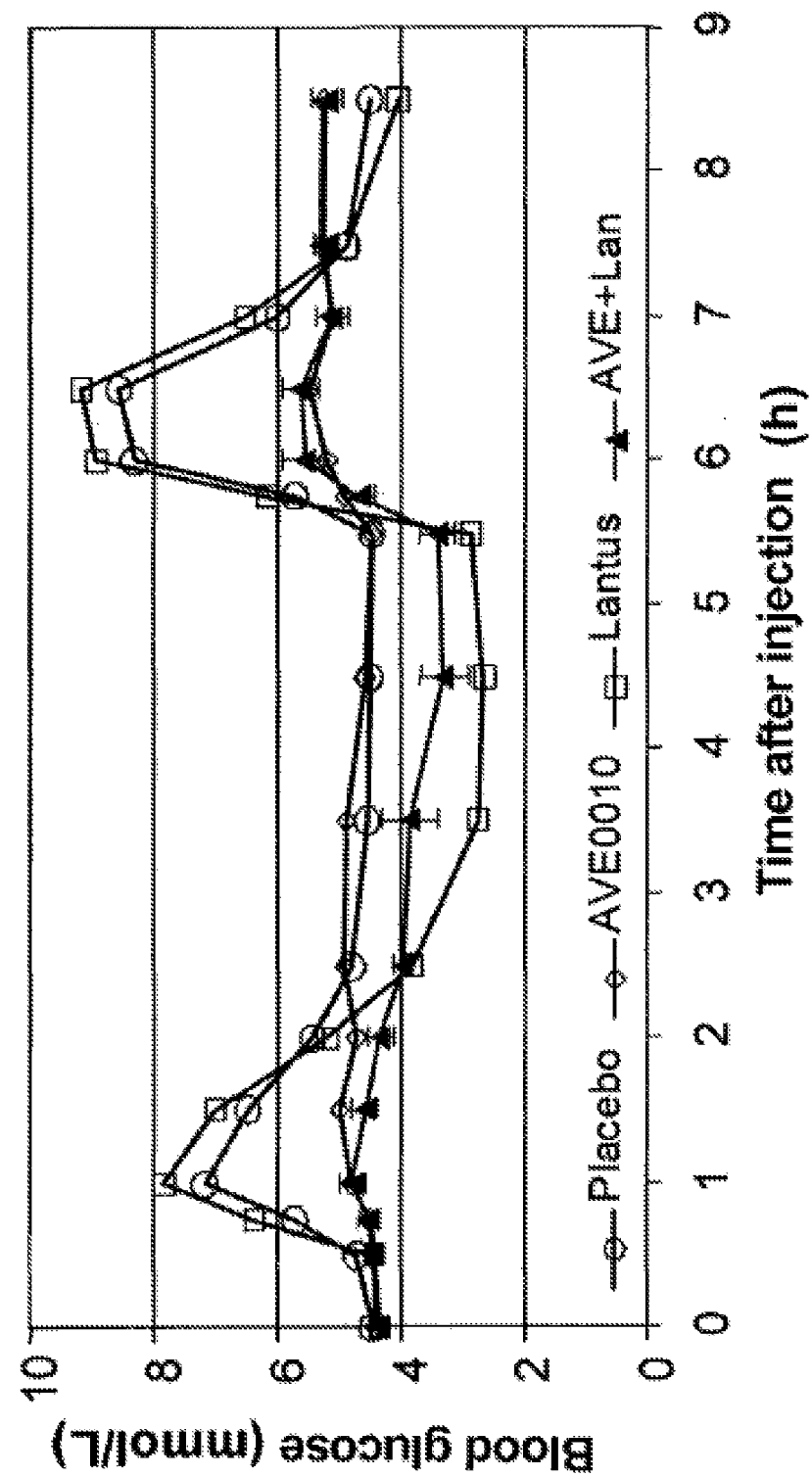
Figure 5A:
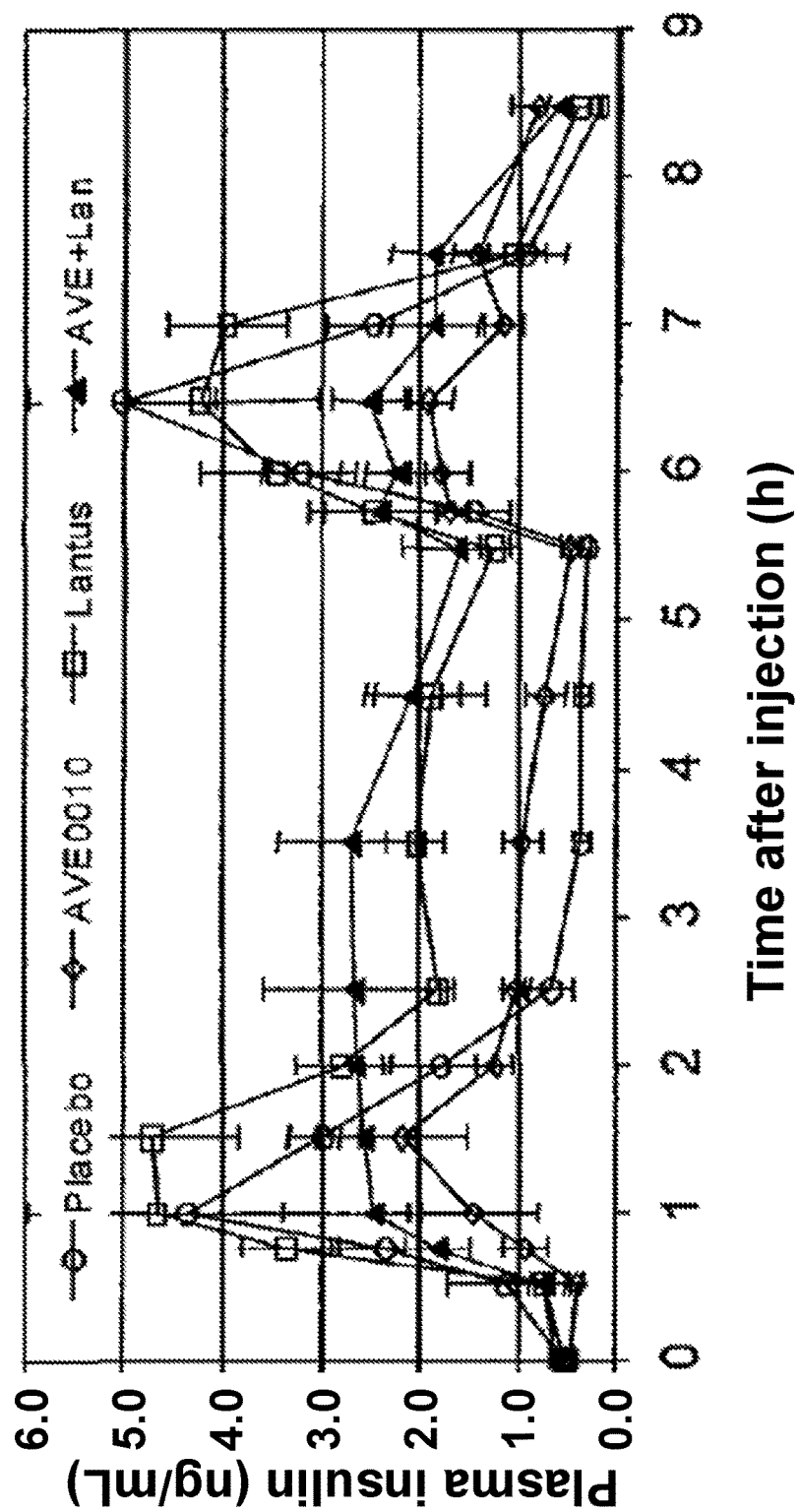
Figure 5B:
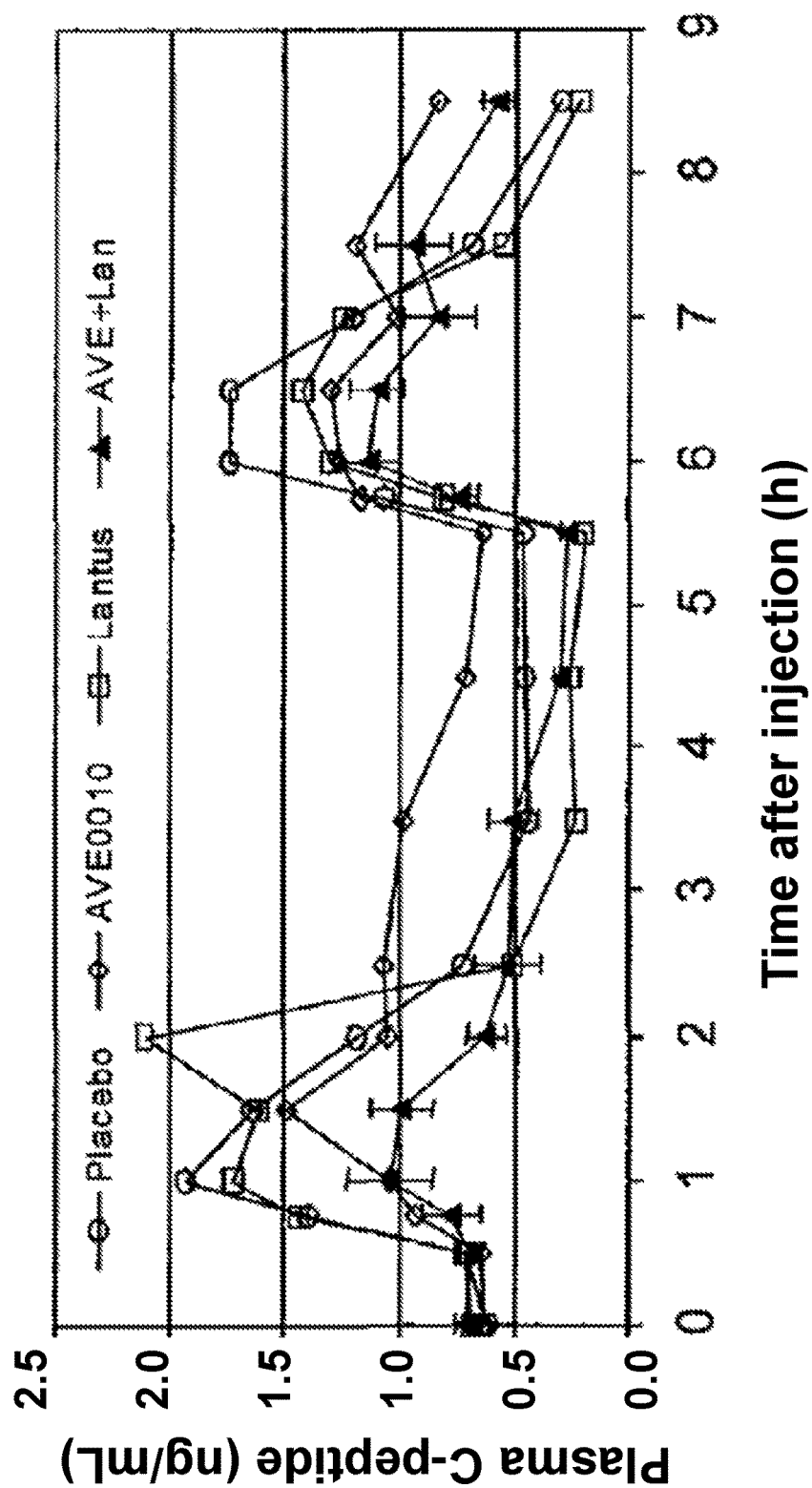
Figure 6:
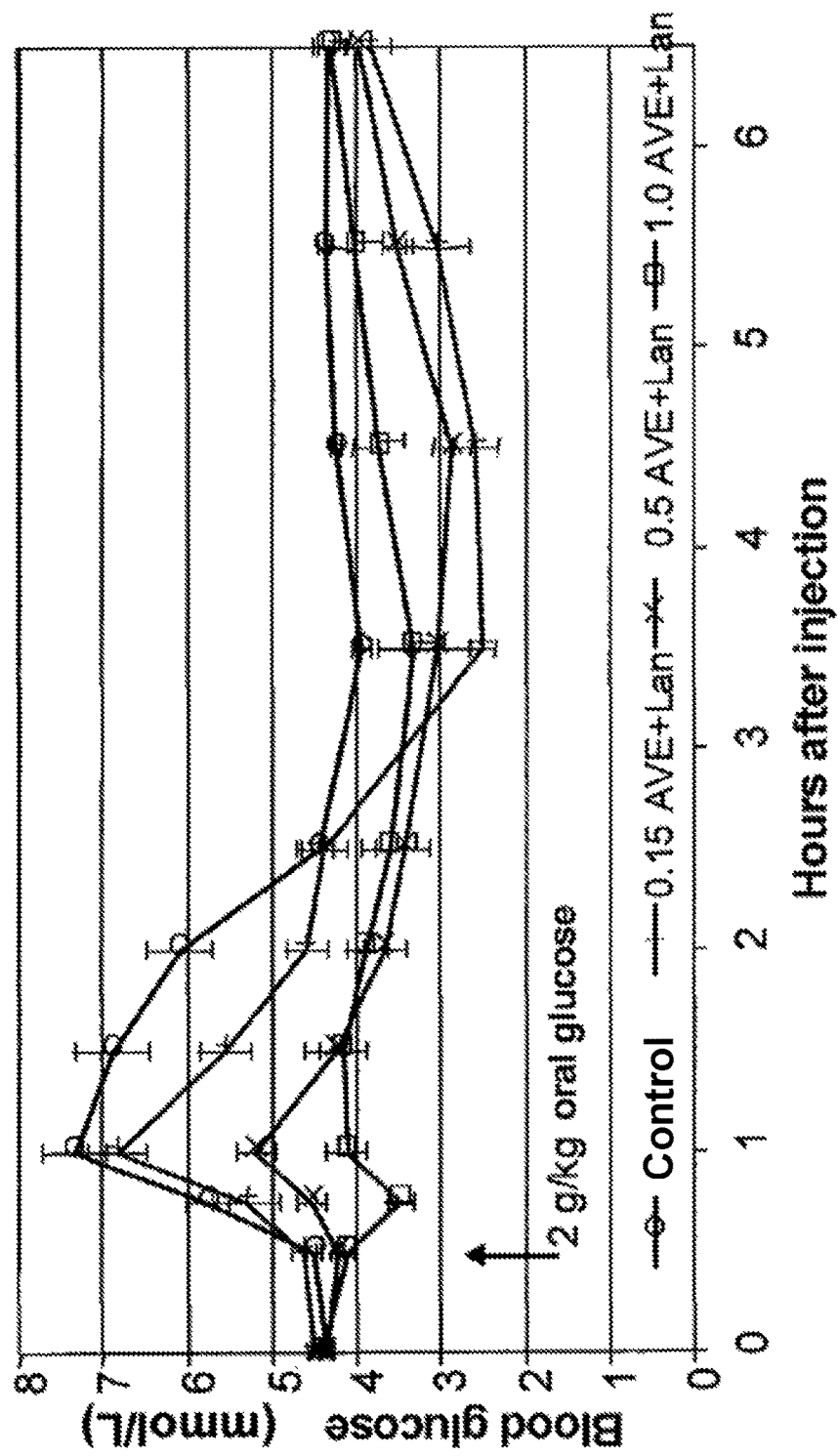
Figure 7:
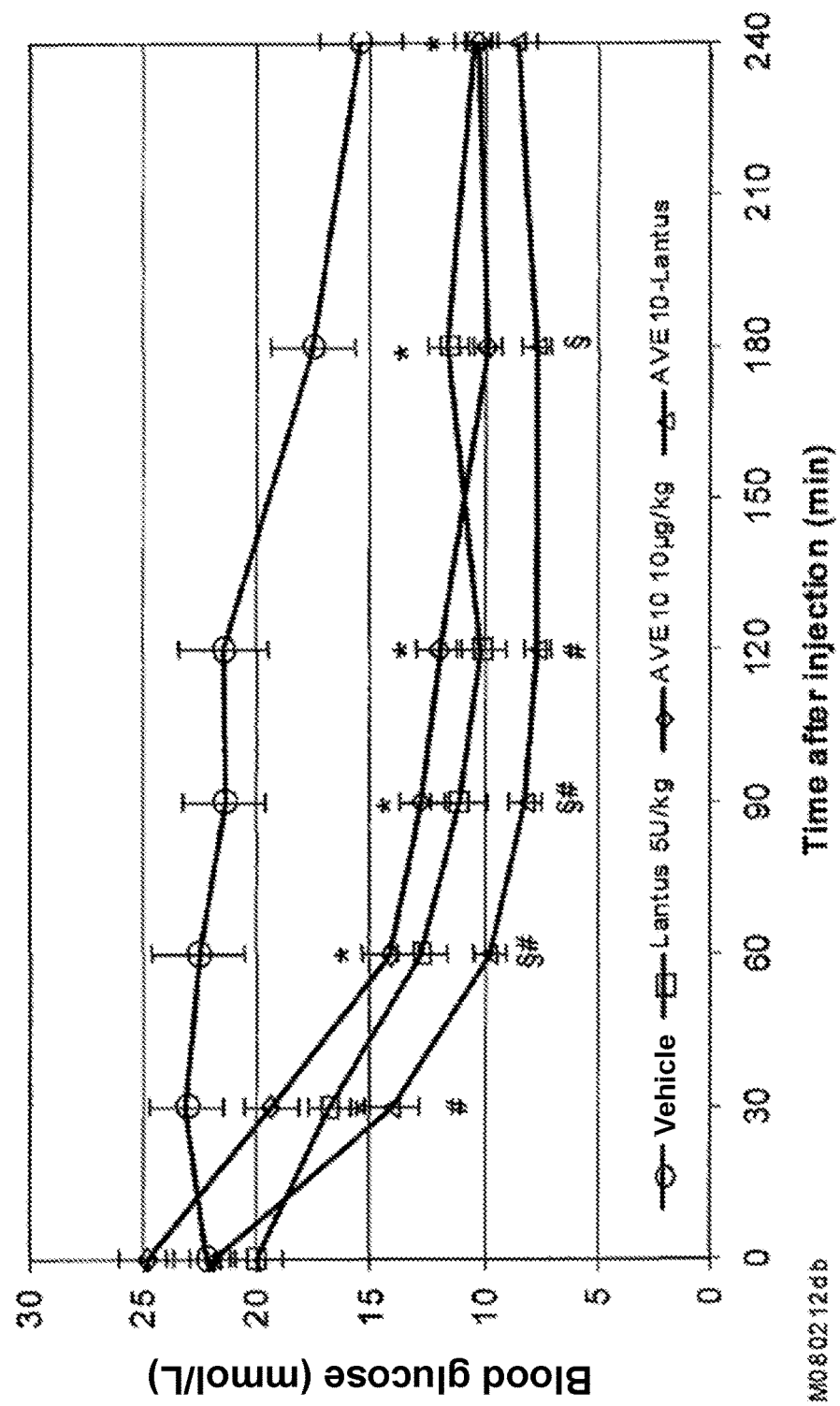
Figure 8:
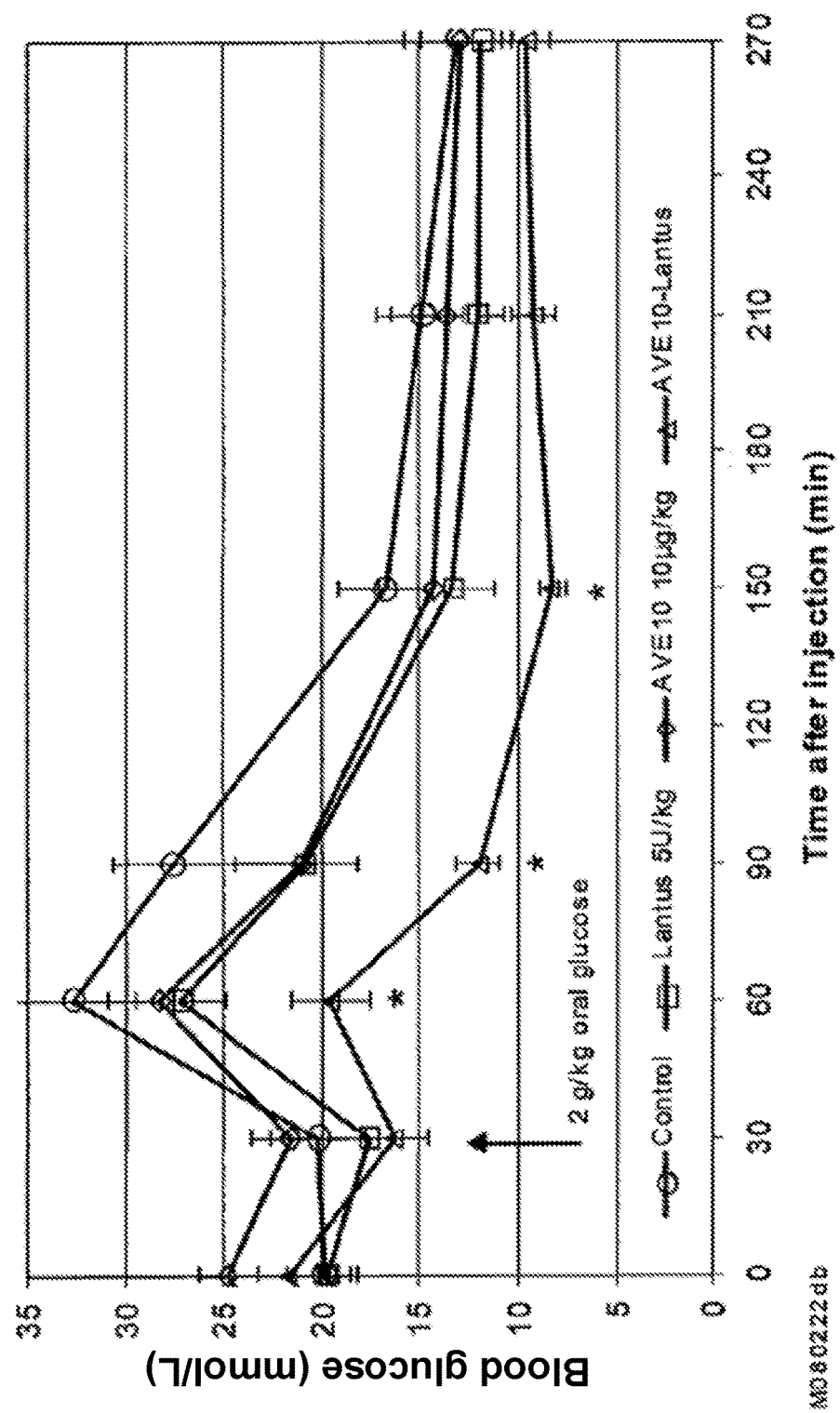
Figure 10:
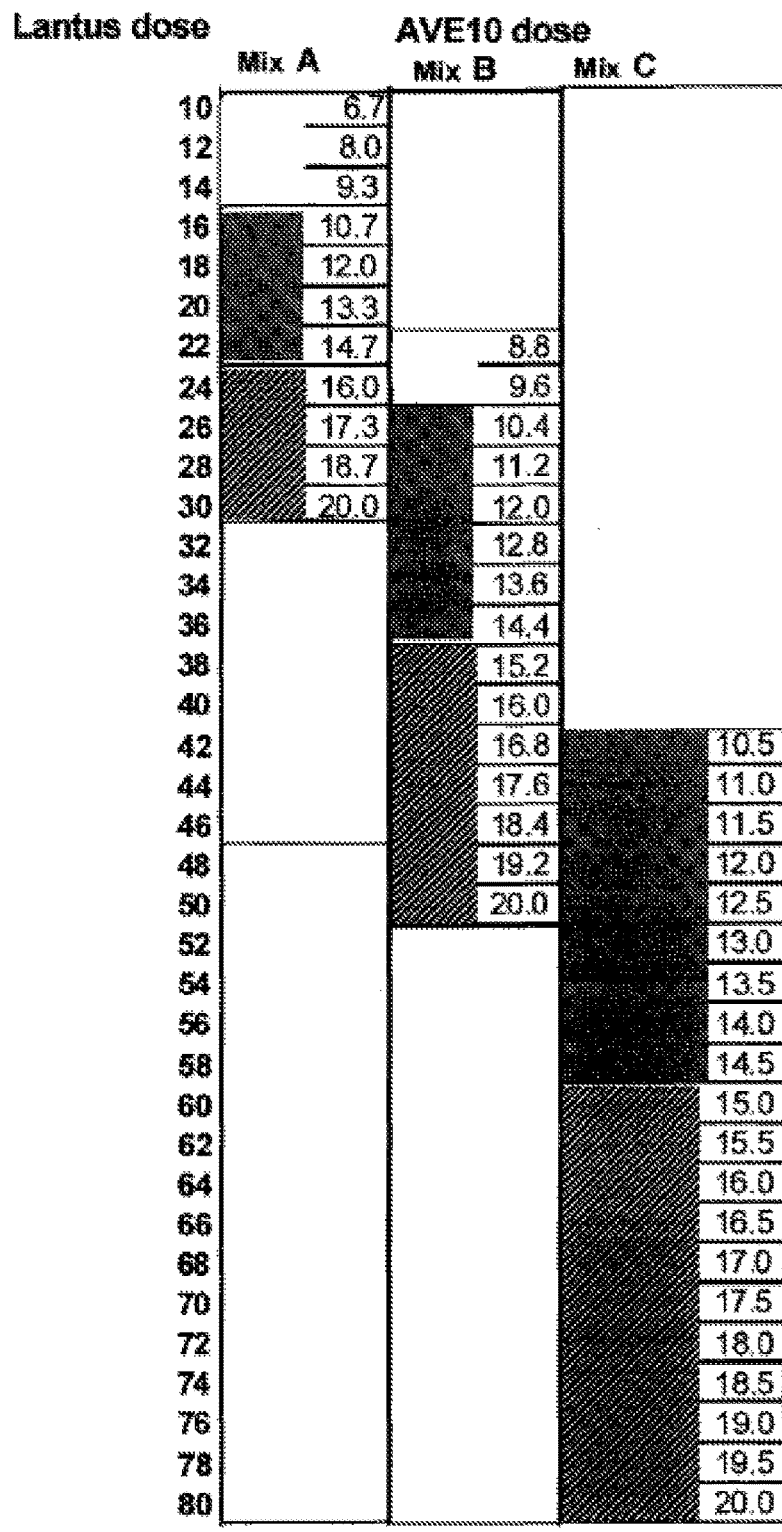

FIG. 1: Study design for oral glucose tolerance test
FIG. 2: OGTT in the dog: Effect of insulin glargine relative to placebo.
FIG. 3: OGTT in the dog: Effect of AVE0010 relative to placebo.
FIG. 4: OGTT in the dog: Effect of an AVE0010/insulin glargine combination on blood glucose level.
FIG. 5A: OGTT in the dog: Effect of an AVE0010/insulin glargine combination on plasma insulin.
FIG. 5B: OGTT in the dog: Effect of an AVE0010/insulin glargine combination on the c-peptide level.
FIG. 6: OGTT in the dog: Effect of a dose lowering of AVE0010 with different proportions relative to insulin glargine in the combined formulation.
FIG. 7: Effect of an AVE0010/insulin glargine combination on blood glucose in the diabetic db/db mouse.
FIG. 8: Effect of an AVE0010/insulin glargine combination in the oral glucose tolerance test in the diabetic db/db mouse.
FIG. 9A: Effect of an AVE0010/insulin glargine combination on cytokine-induced-cell apoptosis in vitro.
FIG. 9B: Effect of an AVE0010/insulin glargine combination on lipotoxicity-induced cell apoptosis in vitro.
FIG. 10: The "3 pens cover all" system.

EXAMPLES

Example 1

Model: Oral glucose tolerance test (OGTT) in healthy dogs: Comparison of the insulin glargine/AVE0010 combination with the two individual active compounds.
Animals
  Male normoglycemic beagles
  Bodyweight: ~15 kg
  Number per group: n=6
Study Design (See FIG. 1)
  Individual subcutaneous injections of placebo or test formulation at time 0
  2 oral administrations of glucose, at 2 g of glucose/kg of bodyweight, at times 30 min and 5 h
  Blood samples are taken to determine blood glucose, plasma insulin, and c-peptide
Group Division (n=6)
  Placebo (Lantus placebo formulation without API)
  Insulin glargine (0.3 µl/kg s.c., equivalent to 1.8 nmol/kg). Insulin glargine is Gly(A21)-Arg(B31)-Arg(B32) human insulin.
  AVE0010 (10 µg/kg s.c. in Lantus placebo formulation, equivalent to 2 nmol/kg).
  AVE0010 is des Pro$^{36}$exendin-4(1-39)-Lys$_6$-NH$_2$.
  AVE0010/insulin glargine combination (10 µg/kg AVE0010/0.3 µl/kg insulin glargine s.c.)

Example 2

OGTT in the dog: Effect of insulin glargine relative to placebo
The experiment was carried out in accordance with the protocol described in example 1.
  repeated OGTT (2 g/kg p.o.)
  male beagle, n=6
  mean±Sem
  placebo=Lantus placebo
  insulin glargine (0.3 U/kg s.c.)
Result: The data are shown in FIG. 2. The single administration of insulin glargine does not prevent the OGTT-induced increase in blood glucose. Insulin glargine reinforces the expected delayed lowering of blood glucose concentration in the postabsorptive phase.

Example 3

OGTT in the dog: Effect of AVE0010 relative to placebo
The experiment was carried out in accordance with the protocol described in example 1.
  repeated OGTT (2 g/kg p.o.)
  male beagle, n=6
  mean±Sem
  placebo=Lantus placebo
  AVE0010 (10 µg/kg s.c.)
Result: The data are shown in FIG. 3. AVE0010 prevents the OGTT-induced postprandial increase in blood glucose almost completely. There is no effect on the glucose concentration in the postabsorptive phase. This example shows that the effect of AVE0010 on the OGTT-induced postprandial increase in blood glucose is complementary to the blood sugar-lowering effect of insulin glargine in the postabsorptive phase.

Example 4

OGTT in the dog: Effect of an AVE0010/insulin glargine combination on the blood glucose level.
The experiment was carried out in accordance with the protocol described in example 1
  repeated OGTT (2 g/kg p.o.)
  male beagle, n=6
  mean±Sem
  placebo=Lantus placebo
  AVE0010 (10 µg/kg s.c.)
  Insulin glargine (0.3 U/kg s.c.)
  AVE+Lan (=premix of 10 µg/kg of AVE0010 and 0.3 U/kg of insulin glargine in one formulation)
Result: The data are shown in FIG. 4. The combination has the same action on the postprandial glucose increase as AVE0010 (cf. example 3). The hypoglycemic effect of insulin glargine In the postabsorptive phase is likewise present, but attenuated (cf. example 2). This is a synergistic effect of insulin glargine and AVE0010, since AVE0010 alone has no effect on the level of glucose, which has fallen again following administration of glucose, and insulin glargine on its own has no effect on the postprandial glucose level.

Example 5

OGTT in the dog: Effect of an AVE0010/insulin glargine combination on the plasma insulin and the c-peptide level.

The experiment was carried out in accordance with the protocol described in example 1.
  repeated OGTT (2 g/kg p.o.)
  male beagle, n=6
  mean±Sem
  placebo=Lantus placebo
  AVE0010 (10 µg/kg s.c.)
  Insulin glargine (0.3 U/kg s.c.)
  AVE+Lan (=premix of 10 µg/kg of AVE0010 and 0.3 U/kg of insulin glargine in one formulation)

The C-peptide is released in the course of the conversion of proinsulin to insulin, and serves as a marker for the secretion of insulin by the pancreatic β-cells. In a glucose loading test, the c-peptide can be used to determine the response capacity of the pancreas.

Result: The data are shown in FIG. 5A and FIG. 5B. In the combination group, the postprandial reduction in insulin is followed by an increased postabsorptive insulin glargine level C-peptide levels for the combination correspond to the insulin curve of AVE0010 during the prandial phases, and of insulin glargine during the postabsorptive phase.

Example 6

OGTT in the dog: Effect of a dose lowering of AVE0010 with different proportions to insulin glargine in the combined formulation.

The experiment was carried out in accordance with the protocol described in example 1.
  repeated OGTT (2 g/kg p.o.)
  male beagle, n=11/6/6/6
  mean±Sem
  control=Lantus placebo
  AVE+Lan (=premix of 0.15 to 1.0 µg/kg of AVE0010 and 0.3 U/kg of insulin glargine in one formulation). In examples 2 to 5, AVE0010 concentrations of 10 µg/kg were used.

Result: The data are shown in FIG. 6. A reduction in the AVE0010 dose from 10 µg/kg (cf. in particular example 4) to 1 µg/kg (i.e., by a factor of 10), and the resultant increase in the proportion of insulin glargine to AVE0010, has no effect on the synergistic activity of the combination of AVE0010 with insulin glargine (cf. in particular example 4). Only at significantly smaller AVE0010 doses does the effect of the combination approach the effect of insulin glargine alone (ct in particular FIG. 2). The AVE0010 dose may therefore be varied at least within one order of magnitude (i.e., by a factor of at least 10) without loss of the synergistic effect.

Example 7

Model: Diabetic, insulin-resistant db/db mouse: Comparison of the insulin glargine/AVE0010 combination with the two individual active compounds.
  Animals
  Female db/db mouse
  Age: 10-11 weeks
  Number per group: n=10
Study Design
  Individual subcutaneous injection of placebo or test formulation
  Taking of blood samples to determine blood glucose
Group Division
  Placebo (=Lantus placebo formulation without API)
  AVE0010 (10 µg/kg s.c.)
  Insulin glargine (5 IU/s.c.)
  AVE0010/insulin glargine combination (premix of 10 µg/kg of AVE0010 plus 5 IU/kg of insulin glargine s.c.)

Example 8

Effect of an AVE0010/insulin glargine combination on blood glucose in the diabetic db/db mouse The experiment was carried out in accordance with the protocol described in example 7.
  Female db/db mouse, 10 weeks
  n=10, mean±Sem
  Vehicle=Lantus placebo
  AVE0010 (10 µg/kg sc)
  Lantus (5 U/kg sc)
  AVE0010/insulin glargine (=premix of AVE0010 10 µg/kg and insulin glargine 5 U/kg in one formulation)

Result: The data are shown in FIG. 7. In diabetic db/db mice, the AVE0010/insulin glargine combination produced a more rapid and more pronounced decrease in the blood glucose concentration as compared with the two individual active compounds. Consequently the combination takes diabetic db/db mice closer to normoglycemia than either of the two active compounds alone.

Example 9

Effect of an AVE0010/insulin glargine combination in the oral glucose tolerance test in the diabetic db/db mouse The experiment was carried out in accordance with the protocol described in example 7. Additionally an OGTT (2 g/kg p.o. @ 30 min) was carried out.
  Female db/db mouse, 11 weeks
  n=10, mean±Sem
  Control=Lantus placebo
  AVE0010 (10 µg/kg sc)
  Insulin glargine (5 U/kg sc)
  AVE0010/insulin glargine (=premix of AVE0010 10 µg/kg and insulin glargine 5 U/kg in one formulation)

Result The data are shown in FIG. 8. The AVE0010/insulin glargine combination leads to significantly improved glucose tolerance and lower postabsorptive glucose levels.

Example 10

Effect of the AVEOO 10/insulin glargine combination on cytokine- and lipotoxicity-induced β-cell apoptosis in vitro.
  Insulinoma cell line INS-1, rat
  Incubation with the test compound for 5 h
  Further incubation with a cytokine mix for 22 h (1 ng/mL IFN-γ+4 ng/mL IL-1β) or
  Further incubation with 0.5 mM FFA for 18 h (palmitates: BSA 3:1)

The measures used for the apoptosis are the caspase-3 activity and the fragmentation of the cell nuclei, which correlate with apoptosis.

Result: The data are shown in FIG. 9A and FIG. 9B. AVE0010 or insulin glargine (glargine, Glar) alone prevent the apoptosis by ~40-50%. The AVE0010 and insulin glargine combination prevents apoptosis significantly better. On the basis of this synergistic effect, the combination brings about increased protection against cytokine- and lipotoxicity-induced apoptosis.

Example 11

The "3 pens cover all" system (FIG. 10)
3 premix pens with 3 different predetermined proportions:
Mix A: 100 U of insulin glargine+66.66 μg of AVE0010 per mL
Mix B: 100 U of insulin glargine+40 μg of AVE0010 per mL
Mix C: 100 U of insulin glargine+25 μg of AVE0010 per mL.

Use of the 3 premix pens: The table in FIG. 10, representing an example, starts from a therapeutic range of 15 to 80 U per dose of insulin glargine and 10 to 20 μg of AVE0010. For a particular patient, a dose of insulin glargine to be administered is specified or predetermined. The predetermined dose is looked up in the left-hand column. Where the columns MIX A-MIX C specify a corresponding AVE0010 dose in the range between 10 and 20 μg, the corresponding MIX is selected, dosed, and administered. The ranges are overlapping: for example, in the case of a requirement of 26 to 30 U of insulin glargine, it will be possible to choose MIX A or MIX B (with a higher dose of AVE0010). The same applies to MIX B and C. If, for example, a dose of 50 U of insulin is intended, then 0.5 ml of MIX B or MIX C can be dosed. This dose contains 20 μg (MIX B) or 12.5 μg (MIX C) of AVE0010.

Conclusion: On the assumption that a probable AVE0010 effect is obtained at between 10 and 15 μg, and a therapeutic effect between 15 and 22 μg, almost all patients who take insulin glargine doses of 15-80 U can also obtain therapeutic doses of AVE0010 of between 10 and 20 μg if they use one of the three premix pens which contain three different insulin glargine:AVE0010 ratios (Mix A, B or C). On the basis of the broad range of possible proportions of insulin glargine to AVE0010 (cf. example 6) with a synergistic effect, the proportions in the pens can be tailored such that for each dose of insulin glargine there is a synergistic dose of AVE0010 in at least one pen.

Example 12

This example shows how a combination of two or more active compounds can be formulated in such a way that, when two or more compositions are combined, both active compounds can be administered in any desired amounts and in any desired proportions to one another. It is taken into account here that at least one of the active compounds must not be diluted as a result of the combining (e.g., through mixing directly prior to administration).

In this example, the designations "active A" and "active B" stand for any desired active compounds. In particular, active A is an insulin and active B is a GLP-1 agonist. Active A can also be a GLP-1 agonist, and active B can also be an insulin.

1. Comparative Example

For a combination therapy with an active A (e.g., an insulin) and an active B (e.g., a GLP-1 agonist), a container 1 with a composition with active A at a concentration of a mg/ml, and a container 2 with a composition with active B at a concentration of b mg/ml, are provided.

For the administration of a combination of the two actives, a volume $V_1$ ml from container 1 and a volume $V_2$ ml from container 2 are mixed.

For the dosing of the two actives, at given concentrations a and b, the volumes $V_1$ and $V_2$ to be administered are selected in dependence on the amount of the actives A and B to be administered. The volumes $V_1$ and $V_2$ of the two actives are determined on the basis of the amount of active, as follows:

| | |
|---|---|
| $V_1 \cdot a$ mg | Amount of active A: |
| $V_2 \cdot b$ mg | Amount of active B: |

The concentrations of the actives A and B in the mixture of the two compositions are determined as follows.

| | |
|---|---|
| $x$ mg/mL$= V_1 \cdot a/(V_1+V_2)$ | Active A: |
| $y$ mg/mL$= V_2 \cdot b/(V_1+V_2)$ | Active B: |

$V_1+V_2$ is the total administered volume. This means that the two actives dilute one another. With this system, therefore, it is not possible to keep, for example, the concentration of the active A (e.g., of the insulin) at a predetermined level in the case of varying amounts of active B.

2. Inventive Example

In this example, for a combination therapy with an active A (e.g., an insulin) and an active B (e.g., a GLP-1 agonist), a container 1 with a composition with active A at a concentration of a mg/ml, and a container 2 with a composition with active A at a concentration of a mg/ml and with active B at a concentration of b mg/ml, are provided. The concentration of the active A is therefore the same in both compositions.

For the administration of a combination of the two actives, a volume $V_3$ ml from container 1 and a volume $V_2$ ml from container 2 are mixed.

For the dosing of the two actives, at given concentrations a and b, the volumes $V_3$ and $V_2$ to be administered are selected in dependence on the amount of the actives A and B to be administered. The volumes $V_3$ and $V_2$ of the two actives are determined on the basis of the amount of active, as follows:

| | |
|---|---|
| $(V_3 \cdot a + V_2) \cdot a$(mg)) | Amount of active A: |
| $V_2 \cdot b$ mg | Amount of active B: |

The concentrations of the actives A and B are determined as follows.

| | |
|---|---|
| $a$ mg/mL$=(V_3 \cdot a+V_2 \cdot a)/(V_3+V_2)$ | Active A: |
| $z$ mg/mL$=V_2 \cdot b/(V_3+V_2)$ | Active B: |

$V_3+V_2$ is the total administered volume. From the above calculation it is evident that the concentration of the active A is always a mg/ml, i.e., is constant, irrespective of what volume ratio $V_3/V_2$ is being dosed.

Comparing the comparative example (see section 1) with the present inventive example, it is apparent that, for an equal dosing quantity of actives A and B, the total volume required in the inventive example is lower.

For a given dose (amount of active compound) of the active A, the figure in the comparative example is:

$V_1 \cdot a$ mg

In the inventive example it is:

$(V_3 \cdot a + V_2 \cdot a)$ mg

Since the amount of active compound is to be the same in both cases, $$(V_3 \cdot a + V_2 \cdot a) = V_1 \cdot a$$

$$(V_3 + V_2) \cdot a = V_1 \cdot a$$

and $V_3 + V_2 = V_1$ or $V_3 = V_1 - V_2$

Here, the volume $V_2$ in which the active B is administered is the same in both case The total volume in the comparative example is $V_1 + V_2$
The total volume in the inventive example is $V_3 + V_2$
According to the above equation, for the inventive example it is the case that:

$$V_3 + V_2 = V_1 - V_2 + V_2 = V_1$$

This volume $V_1$ is smaller than the volume $V_1 + V_2$ of the comparative example.

As a result of the mixing of the composition with actives A and B with the composition with active A, active B is diluted. This dilution is less than the dilution of the active B in the comparative example (i.e., the concentration b>concentration z>concentration $b > z$ $b > V_2 \cdot b / (V_3 + V_2)$ $b > b\ V_2/(V_3+V_2)$, where $V_2/(V_3+V_2)$ is <1, and $z > y$ $V_2 \cdot b / (V_3 + V_2) > V_2 \cdot b / (V_1 + V_2)$ $1/(V_3 + V_2) > 1/(V_1 + V_2)$ $1/(V_1 - V_2 + V_2) > 1/(V_1 + V_2)$ $1/V_1 > 1/(V_1 + V_2)$ Hence the dosing system of the invention for administering variable doses of the actives A (e.g., an insulin) and B (e.g., a GLP-1 agonist) has three advantages over the comparative system:

The concentration of active A (e.g., an insulin) can be kept constant at a predetermined level Where the doses of actives A and B to be administered are the same, the total volume to be administered is smaller.

The dilution of active B (e.g., the GLP-1 agonist) is less than in the comparative experiment. Accordingly the concentration of active B can be held more easily within a predetermined range.

The present example can be readily extended to medicaments with three or more active compounds, the first active compound being present in all of the compositions (preferably in equal weight fractions) and there being at least one further active compound in each further composition. The first composition can be mixed with each further composition in the same proportion without the concentration of the active compound in the first composition becoming diluted.

The invention claimed is:

1. A prefilled syringe comprising a pharmaceutical formulation, wherein the pharmaceutical formulation comprises a combination of:
   (a) insulin glargine or a pharmaceutically acceptable salt thereof, and
   (b) desPro$^{36}$exendin-4(1-39)-Lys$_6$-NH$_2$ (AVE0010) or a pharmaceutically acceptable salt thereof;
   wherein the pharmaceutical formulation has a concentration of insulin glargine that is about 100 units/mL and a concentration of AVE0010 that is about 33 μg/mL; and
   wherein the prefilled syringe is configured to administer the pharmaceutical formulation at a dosage of insulin glargine between about 15 units and about 80 units and a dosage of AVE0010 between about 5 μg and about 2 mg.

2. The prefilled syringe of claim 1,
   wherein the prefilled syringe is configured to administer the pharmaceutical formulation at a dosage of insulin glargine between about 15 units and about 60 units and a dosage of AVE0010 between about 5 μg and about 20 μg.

3. The prefilled syringe of claim 1,
   wherein the prefilled syringe is configured to administer the pharmaceutical formulation at a dosage of insulin glargine between about 15 units and about 80 units and a dosage of AVE0010 between about 5 μg and about 20 μg.

4. A prefilled syringe comprising a pharmaceutical formulation, wherein the pharmaceutical formulation comprises a combination of:
   (a) insulin glargine or a pharmaceutically acceptable salt thereof, and
   (b) desPro$^{36}$exendin-4(1-39)-Lys$_6$-NH$_2$ (AVE0010) or a pharmaceutically acceptable salt thereof;
   wherein the pharmaceutical formulation has a concentration of insulin glargine that is about 100 units/mL and a concentration of AVE0010 that is about 20 m/ml to about 150 μg/ml.

5. The prefilled syringe of claim 4,
   wherein the pharmaceutical formulation has a concentration of insulin glargine that is about 100 units/mL and a concentration of AVE0010 that is about 25, 33, 40, 66, or 75m/mL.

6. The prefilled syringe of claim 4,
   wherein the pharmaceutical formulation has a concentration of insulin glargine that is about 100 units/mL and a concentration of AVE0010 that is about 33 μg/mL.

7. A prefilled syringe comprising a pharmaceutical formulation, wherein the pharmaceutical formulation comprises a combination of:
   (a) insulin glargine or a pharmaceutically acceptable salt thereof, and
   (b) desPro$^{36}$exendin-4(1-39)-Lys$_6$-NH$_2$ (AVE0010) or a pharmaceutically acceptable salt thereof;
   wherein the pharmaceutical formulation has a concentration of insulin glargine that is about 100 units/mL, and
   wherein the ratio of insulin glargine and AVE0010 in the pharmaceutical formulation is about 1.5 units to about 4 units of insulin glargine to 1 μg of AVE0010.

8. The prefilled syringe of claim 7,
   wherein the ratio of insulin glargine and AVE0010 in the pharmaceutical formulation is about 3 units of insulin glargine to 1 μg of AVE0010.

* * * * *